US012263208B2

(12) United States Patent
Shock et al.

(10) Patent No.: US 12,263,208 B2
(45) Date of Patent: Apr. 1, 2025

(54) RECOMBINANT CELL WALL HYDROLASES

(71) Applicant: Topaz Biosciences, Inc., Emeryville, CA (US)

(72) Inventors: Teresa Shock, San Francisco, CA (US); Oliver Liu, San Francisco, CA (US); Maritza Miller, Oakland, CA (US); Jennifer Shock, San Francisco, CA (US)

(73) Assignee: Topaz Biosciences, Inc., Emeryville, CA (US)

( * ) Notice: Subject to any disclaimer, the term of this patent is extended or adjusted under 35 U.S.C. 154(b) by 0 days.

(21) Appl. No.: 18/882,318

(22) Filed: Sep. 11, 2024

(65) Prior Publication Data

US 2025/0000956 A1  Jan. 2, 2025

Related U.S. Application Data

(63) Continuation of application No. PCT/US2024/034521, filed on Jun. 18, 2024.

(60) Provisional application No. 63/639,416, filed on Apr. 26, 2024, provisional application No. 63/509,160, filed on Jun. 20, 2023.

(51) Int. Cl.
  *A61K 38/48* (2006.01)
  *A61K 9/06* (2006.01)
  *A61P 17/00* (2006.01)
  *C12N 9/50* (2006.01)

(52) U.S. Cl.
  CPC .............. *A61K 38/482* (2013.01); *A61K 9/06* (2013.01); *A61P 17/00* (2018.01); *C12N 9/50* (2013.01)

(58) Field of Classification Search
  CPC .................................................. A61K 38/482
  See application file for complete search history.

(56) References Cited

U.S. PATENT DOCUMENTS

| | | | |
|---|---|---|---|
| 5,093,348 A | 3/1992 | Silvestrini | |
| 8,012,730 B1 | 9/2011 | Donovan | |
| 8,058,225 B2 | 11/2011 | Forchheim et al. | |
| 8,202,516 B2 | 6/2012 | Padmanabhan et al. | |
| 8,361,772 B2 | 1/2013 | Donovan | |
| 8,481,289 B2 | 7/2013 | Donovan et al. | |
| 8,492,519 B2 | 7/2013 | Grallert et al. | |
| 8,557,519 B2 | 10/2013 | Forchheim et al. | |
| 8,748,150 B2 | 6/2014 | Padmanabhan et al. | |
| 9,018,155 B2 | 4/2015 | Forchheim et al. | |
| 9,394,534 B2 | 7/2016 | Beissinger et al. | |
| 9,622,486 B2 | 4/2017 | Padmanabhan et al. | |
| 10,278,398 B2 | 5/2019 | Padmanabhan et al. | |
| 11,236,315 B2 | 2/2022 | Donovan et al. | |
| 2009/0202512 A1 | 8/2009 | Forchheim et al. | |
| 2009/0324576 A1 | 12/2009 | Padmanabhan et al. | |
| 2010/0158886 A1 | 6/2010 | Donovan et al. | |
| 2011/0318328 A1 | 12/2011 | Donovan | |
| 2012/0164126 A1 | 6/2012 | Forchheim et al. | |
| 2012/0237491 A1 | 9/2012 | Padmanabhan et al. | |
| 2014/0065104 A1 | 3/2014 | Forchheim et al. | |
| 2014/0302004 A1 | 10/2014 | Donovan et al. | |
| 2014/0369986 A1 | 12/2014 | Padmanabhan et al. | |
| 2017/0318817 A1 | 11/2017 | Padmanabhan et al. | |
| 2019/0091148 A1 | 3/2019 | Noe et al. | |
| 2019/0297896 A1 | 10/2019 | Padmanabhan et al. | |
| 2022/0053775 A1 | 2/2022 | Padmanabhan et al. | |
| 2023/0088050 A1 | 3/2023 | O'Neill et al. | |

FOREIGN PATENT DOCUMENTS

| | | |
|---|---|---|
| CA | 2661896 A1 | 9/2008 |
| CA | 2696864 A1 | 2/2009 |
| CA | 2651125 C | 6/2016 |
| EP | 2028271 A1 | 2/2009 |
| EP | 2054531 A2 | 5/2009 |
| EP | 2318531 A2 | 5/2011 |
| EP | 2037946 B1 | 2/2015 |
| EP | 3488860 B1 | 1/2022 |
| JP | 2002531107 A | 9/2002 |
| JP | 2005502326 A | 1/2005 |
| JP | 2009536033 A | 10/2009 |
| JP | 2010512761 A | 4/2010 |
| JP | 2010536354 A | 12/2010 |
| JP | 2014050388 A | 3/2014 |
| JP | 2016112020 A | 6/2016 |
| JP | 2018201525 A | 12/2018 |
| WO | WO-2004020635 A1 | 3/2004 |
| WO | WO-2007130655 A2 | 11/2007 |
| WO | WO-2009024327 A2 | 2/2009 |
| WO | WO-2010011960 A2 | 1/2010 |
| WO | WO-2017212422 A1 | 12/2017 |
| WO | WO-2019105936 A1 | 6/2019 |
| WO | WO-2021018619 A1 | 2/2021 |

OTHER PUBLICATIONS

Bliss, C.I., "The toxicity of poisons applied jointly," Annals of Applied Biology, Aug. 1939 26(3):585-615.
Bonar et al., "Human skin microbiota-friendly lysostaphin" International Journal of Biological Macromolecules. (2021) 183:852-860.
Briers et al., "A standardized approach for accurate quantification of murein hydrolase activity in high-throughput assays" J Biochem Biophys Methods. Apr. 10, 2007; 70(3):531-533.
Chang et al., "Characterization of a novel cell wall binding domain-containing *Staphylococcus aureus* endolysin LysSA97" Applied Microbiology and Biotechnology. (2017) 101:147-158.
Choi et al., "A novel chimeric endolysin with enhanced lytic and binding activity against Clostridium perfringens" LWT. May 1, 2023; 181:114776. 9 pages.

(Continued)

*Primary Examiner* — Suzanne M Noakes
(74) *Attorney, Agent, or Firm* — Cooley LLP

(57) ABSTRACT

The present disclosure relates to novel chimeric cell wall hydrolases with anti-*Staphylococcus* activity. The disclosure also relates to compositions comprising these chimeric cell wall hydrolases and uses thereof in the treatment of conditions associated with *Staphylococcus* sp.

29 Claims, 27 Drawing Sheets
Specification includes a Sequence Listing.

(56) References Cited

OTHER PUBLICATIONS

Duyvejonck et al., "Rapid and high-throughput evaluation of diverse configurations of engineered lysins using the VersaTile technique" Antibiotics. (2021) 10(3):293. 12 pages.

Eichenseher et al., "Linker-Improved Chimeric Endolysin Selectively Kills *Staphylococcus aureus* In Vitro, on Reconstituted Human Epidermis, and in a Murine Model of Skin Infection" Antimicrobial Agents and Chemotherapy. (2022) 66(5):e02273-21. 18 pages.

Fuxench et al., "Atopic Dermatitis in America Study: A Cross-Sectional Study Examining the Prevalence and Disease Burden of Atopic Dermatitis in the US Adult Population" J Invest Dermatol. Mar. 2019;139(3):583-590.

Genbank accession No. ANT44936.1, May 13, 2017, 1 page.

Genbank accession No. YP_008058813, Jan. 8, 2023, 2 pages.

Gutierrez et al., "Are Phage Lytic Proteins the Secret Weapon To Kill *Staphylococcus aureus*?" mBio. Jan. 2018; 9(1):e01923-17. 17 pages.

Gutierrez et al., "Design and selection of engineered lytic proteins with *Staphylococcus aureus* decolonizing activity" Frontiers in Microbiology. (2021) 12:723834. 16 pages.

Gutierrez et al., "Phage lytic protein LysRODI prevents staphylococcal mastitis in mice" Frontiers in Microbiology. (2020) 11:7. 13 pages.

Huang et al., "Molecular dissection of phage lysin PlySs2: integrity of the catalytic and cell wall binding domains is essential for its broad lytic activity" Virol. Sin. (2015) 30:45-51.

Ianevski et al., "SynergyFinder: a web application for analyzing drug combination dose-response matrix data," Bioinformatics, 33(15):2413-2415, 2017.

International Search Report and Written Opinion for PCT Application No. PCT/US2024/034521 mailed Oct. 23, 2024, 22 pages.

Invitation to pay additional fees for International Application No. PCT/US2024/034521, mailed Aug. 27, 2024, 2 pages.

Jun et al., "Comparison of the Antibacterial Properties of Phage Endolysins SAL-1 and LysK" Antimicrob Agents Chemother. Apr. 2011; 55(4):1764-1767.

Kost et al., "Association of *Staphylococcus aureus* Colonization With Severity of Acute Radiation Dermatitis in Patients With Breast or Head and Neck Cancer" JAMA Oncology. Jul. 1, 2023; 9(7):962-965.

Kost et al., "Bacterial Decolonization for Prevention of Radiation Dermatitis: A Randomized Clinical Trial" JAMA Oncology. Jul. 1, 2023; 9(7):940-945.

Lee et al., "Development of advanced chimeric endolysin to control multidrug-resistant *Staphylococcus aureus* through domain shuffling" ACS Infectious Diseases. (2021) 7(8):2081-2092.

Lu et al., "CDD/SPARCLE: the conserved domain database in 2020" Nucleic Acids Res. Jan. 8, 2020; 48(D1): D265-D268.

Lu et al., "Cell Wall-targeting Domain of Glycylglycine Endopeptidase Distinguishes among Peptidoglycan Cross-bridges" JBC (2006) 281:549-558.

Madhaiyan et al., "Phylogenomic analyses of the Staphylococcaceae family suggest the reclassification of five species within the genus *Staphylococcus* as heterotypic synonyms, the promotion of five subspecies to novel species, the taxonomic reassignment of five *Staphylococcus* species to *Mammaliicoccus* gen. nov., and the formal assignment of Nosocomiicoccus to the family Staphylococcaceae" Int. J. Syst. Evol. Microbiol (2020) 70:5926-5936.

Matsuzaki et al., "Bacteriophage therapy: a revitalized therapy against bacterial infectious diseases" Journal of Infection and Chemotherapy. (2005) 11:211-219.

Nakonieczna et al., "New bacteriophage-derived lysins, LysJ and LysF, with the potential to control Bacillus anthracis" Applied Microbiology and Biotechnology (2024) 108:76. 14 pages.

Obeso et al., "Lytic activity of the recombinant staphylococcal bacteriophage ΦH5 endolysin active against *Staphylococcus aureus* in milk" International Journal of Food Microbiology. (2008) 128(2):212-218.

O'Flaherty et al., "The Recombinant Phage Lysin LysK Has a Broad Spectrum of Lytic Activity against Clinically Relevant *Staphylococci*, Including Methicillin-Resistant *Staphylococcus aureus*" J Bacteriol. Oct. 2005; 187(20):7161-7164.

Oliveira et al., "Molecular aspects and comparative genomics of bacteriophage endolysins" J Virol. Apr. 2013; 87(8):4558-4570.

Sabala et al., "Anti-staphylococcal activities of lysostaphin and LytM catalytic domain" BMC Microbiol. (2012) 12: 97. 11 pages.

Schmelcher et al., "Evolutionarily distinct bacteriophage endolysins featuring conserved peptidoglycan cleavage sites protect mice from MRSA infection" J Antimicrob Chemother. May 2015; 70(5): 1453-1465.

Silverberg et al., "What are the best endpoints for Eczema Area and Severity Index and Scoring Atopic Dermatitis in clinical practice? A prospective observational study" Br J Dermatol. May 2021; 184(5):888-895.

Son et al., "Development of a novel chimeric endolysin, Lys109 with enhanced lytic activity against *Staphylococcus aureus*" Frontiers in Microbiology. (2021) 11:615887. 12 pages.

Vazquez et al., "Sequence-Function Relationships in Phage-Encoded Bacterial Cell Wall Lytic Enzymes and Their Implications for Phage-Derived Product Design" J Virol. Jun. 2021; 95(14):e00321-21. 23 pages.

Vermassen et al., "Cell wall hydrolases in bacteria: insight on the diversity of cell wall amidases, glycosidases and peptidases toward peptidoglycan" Frontiers in Microbiology. (2019) 10:331. 27 pages.

Wang et al., "Protein domain identification methods and online resources," Comput Struct Biotechnol J (2021)19:1145-1153.

Yadav et al., "Searching for Drug Synergy in Complex Dose-Response Landscapes Using an Interaction Potency Model" Computational and Structural Biotechnology Journal (2015) vol. 13, pp. 504-513.

Yu et al., "Characterization of staphylococcal endolysin LysSAP33 possessing untypical domain composition" J Microbiol. (2021) 59:840-847.

FIG. 3

| MIC (*S. aureus*) | EAD | CBD | | | | | |
|---|---|---|---|---|---|---|---|
| | | LysPALS1 | LysA72 | LysH5 | PlySs2 | ALE1 | LysSA97 |
| | Twort | | 4 | | 0.5 | 32 | |
| | LysCSA5 | | 4 | | 0.5 | 32 | |
| | LysCSA13 | | 16 | | 32 | 32 | |
| | LysSA12 | 32 | 5 | 50 | 2 | 1 | 32 |

| Selectivity (*S. aureus* vs. *S. epidermidis*) | EAD | CBD | | | | | |
|---|---|---|---|---|---|---|---|
| | | LysPALS1 | LysA72 | LysH5 | PlySs2 | ALE1 | LysSA97 |
| | Twort | | 1x | | 2x | 2x | |
| | LysCSA5 | | 4x | | 4x | 4x | |
| | LysCSA13 | | 1x | | 1x | 1x | |
| | LysSA12 | 1x | 32x | 4x | 64x | 128x | 1x |

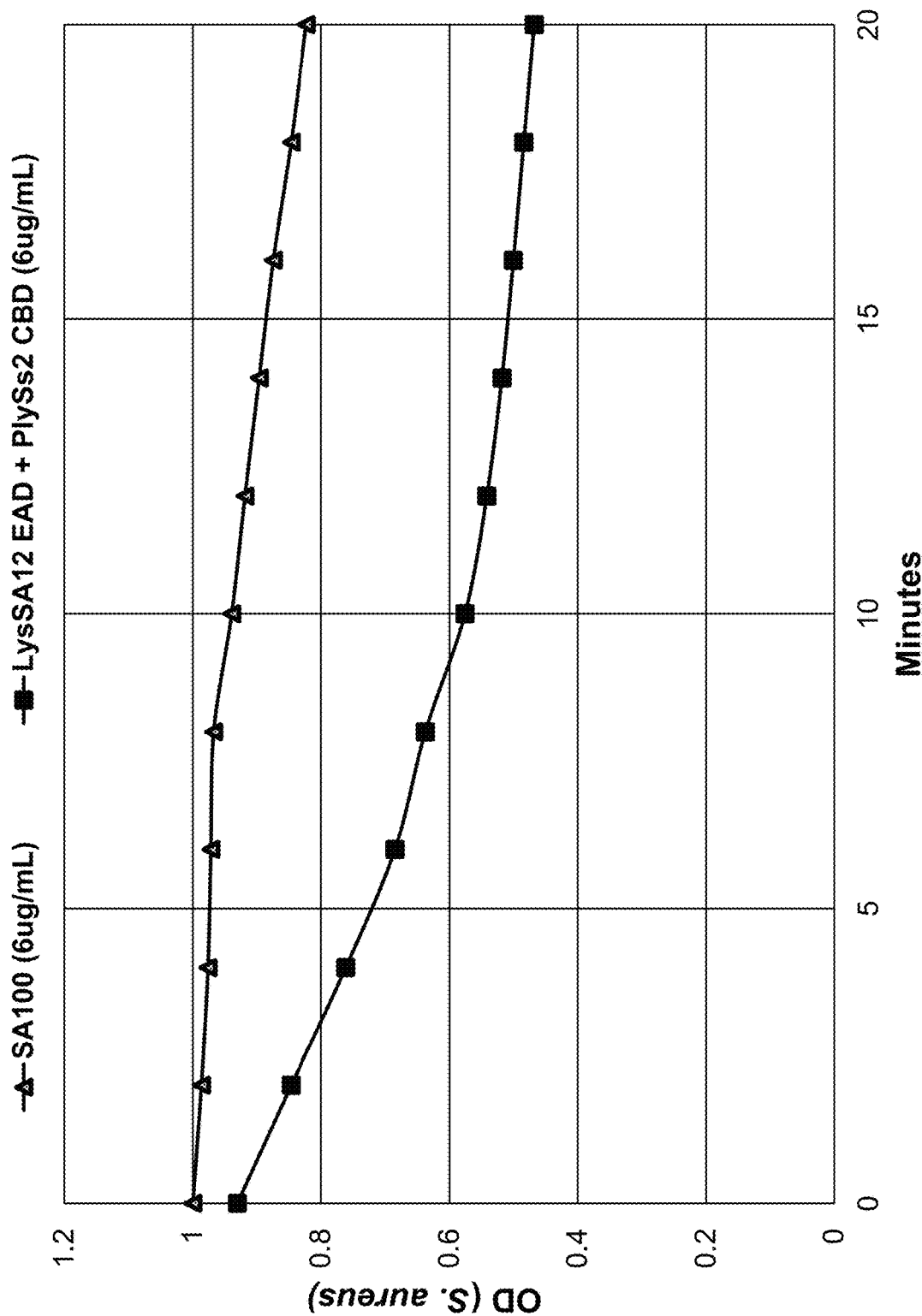

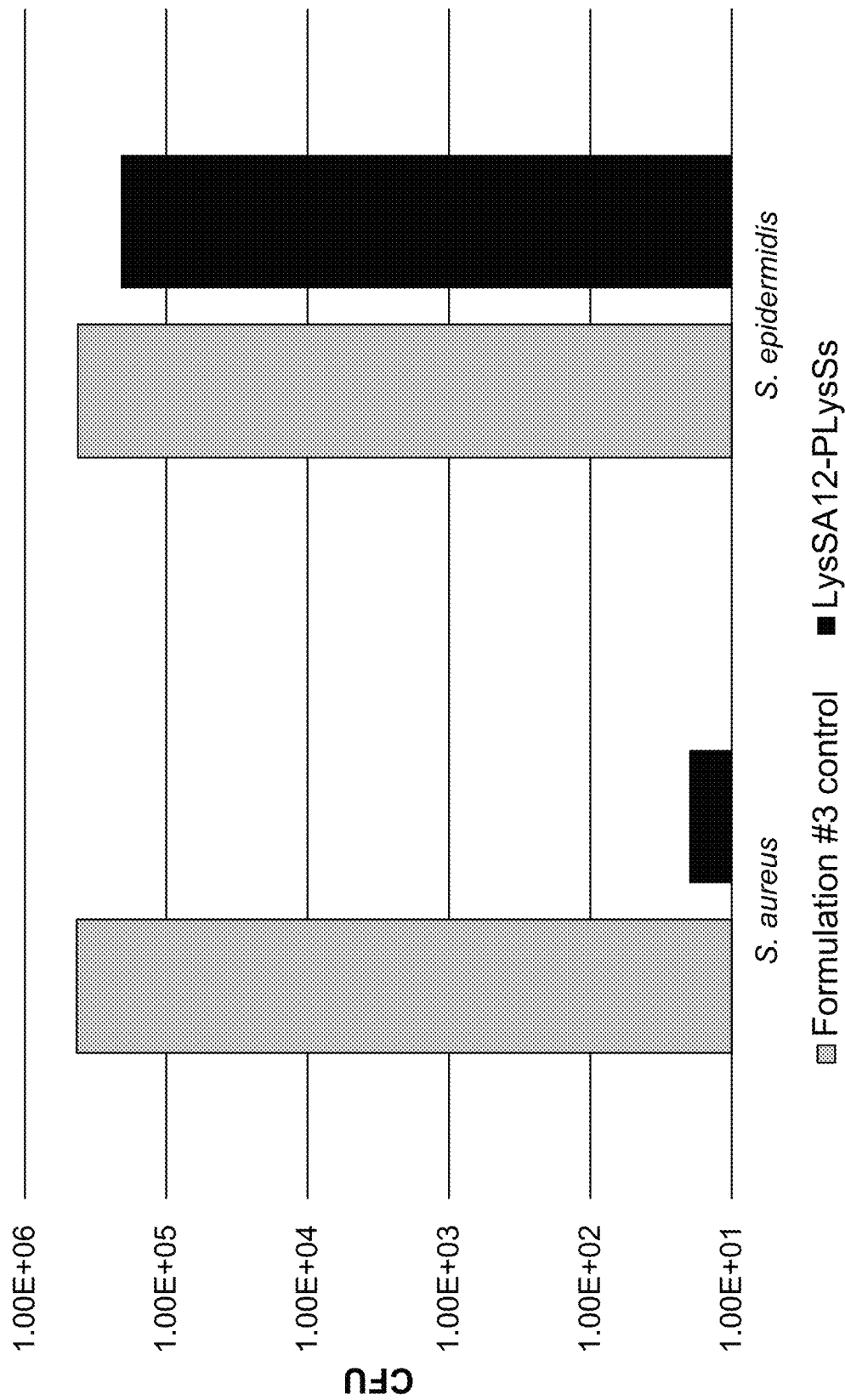

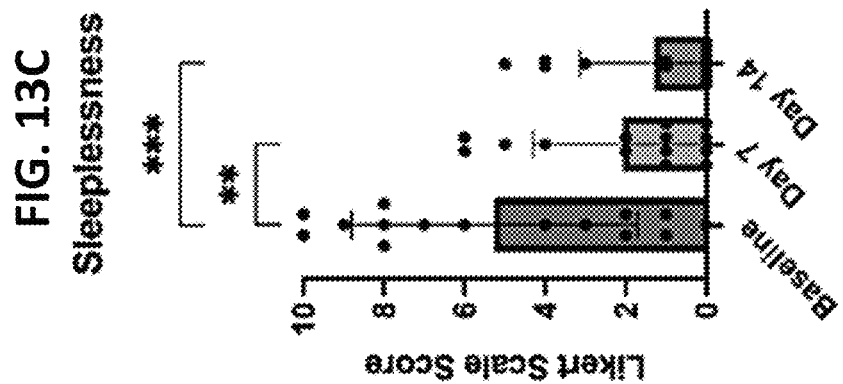
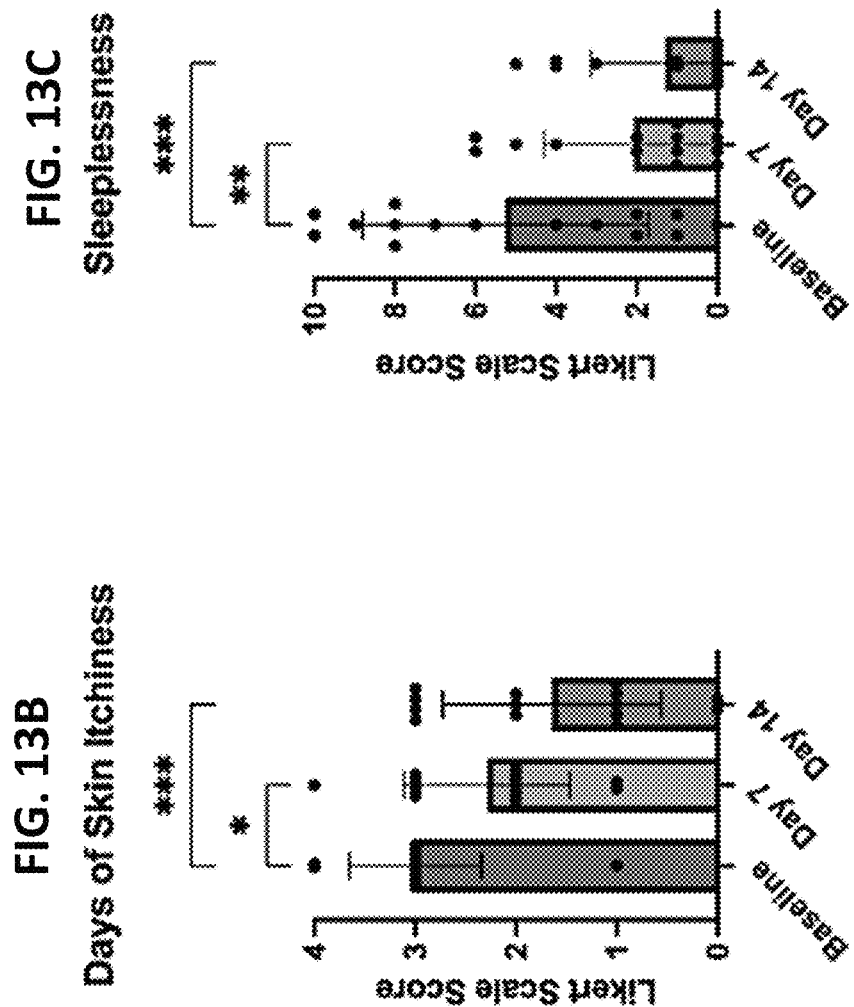
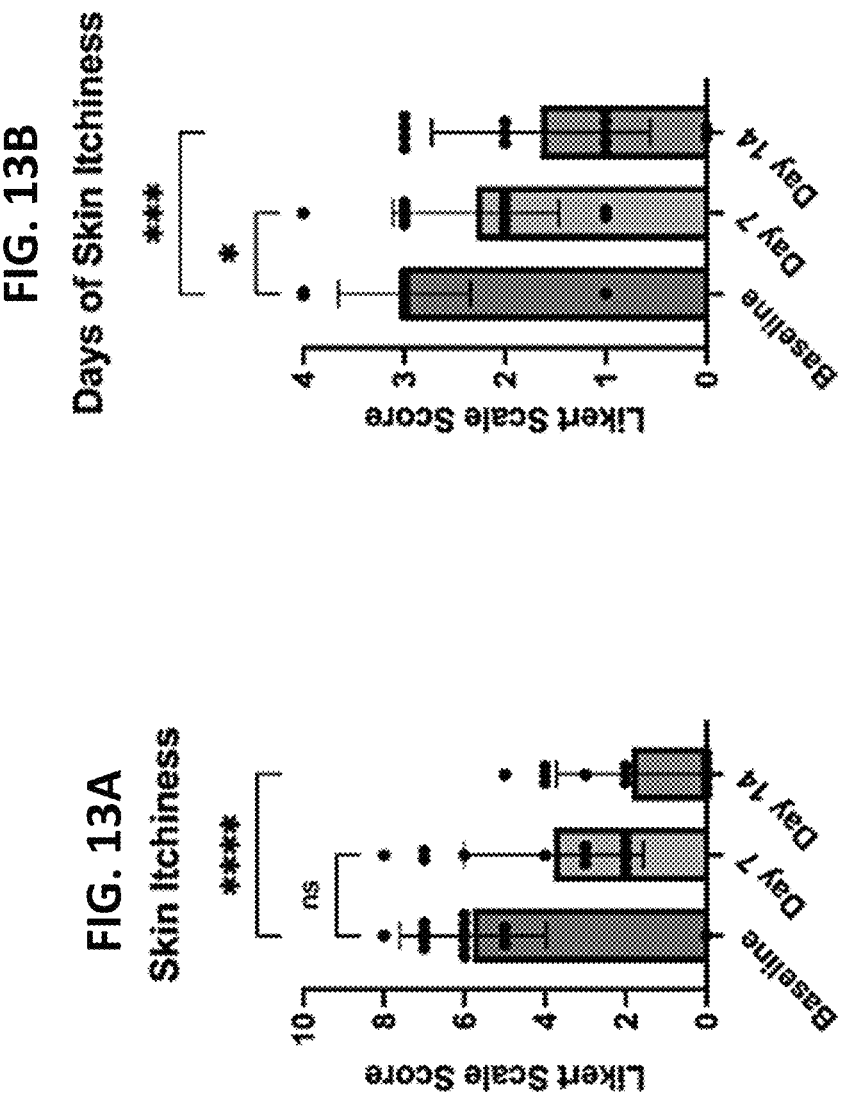
FIG. 13A Skin Itchiness
FIG. 13B Days of Skin Itchiness
FIG. 13C Sleeplessness

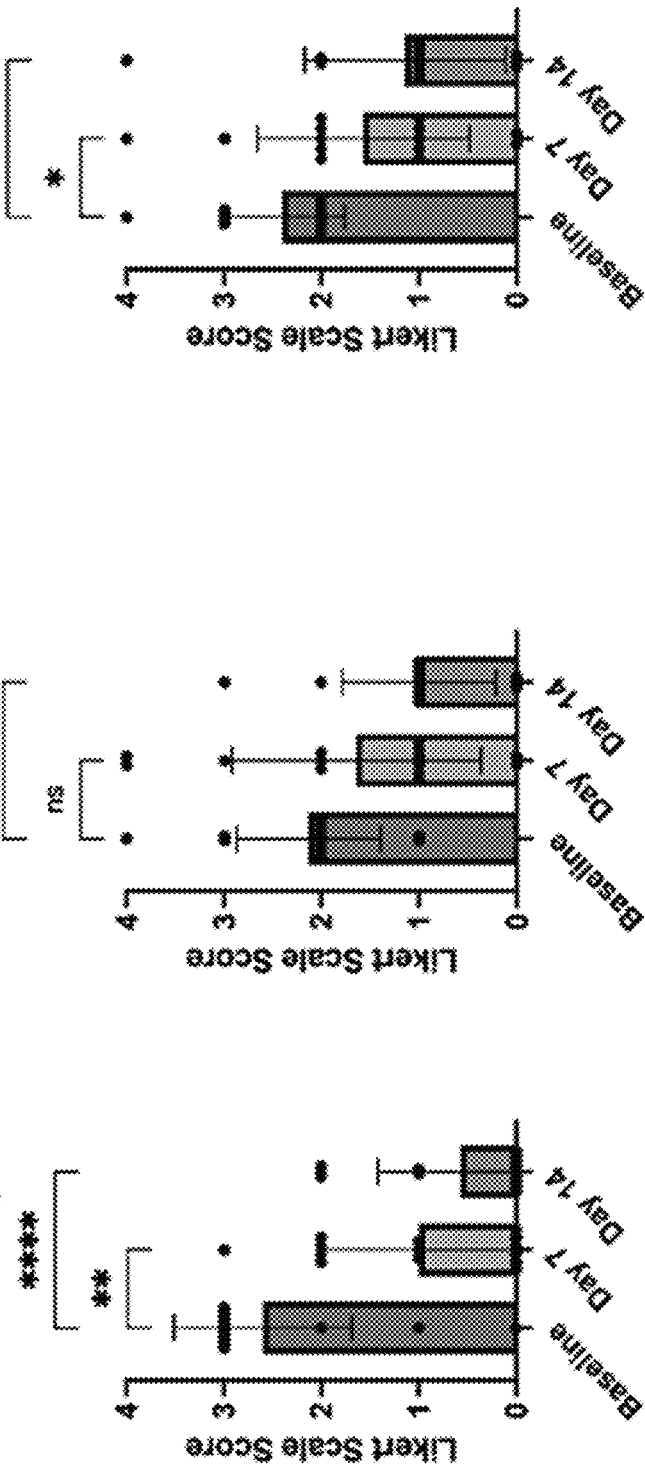
FIG. 13D Frequency of Sleep Disturbed by Skin
FIG. 13E Skin Redness
FIG. 13F Skin Dryness

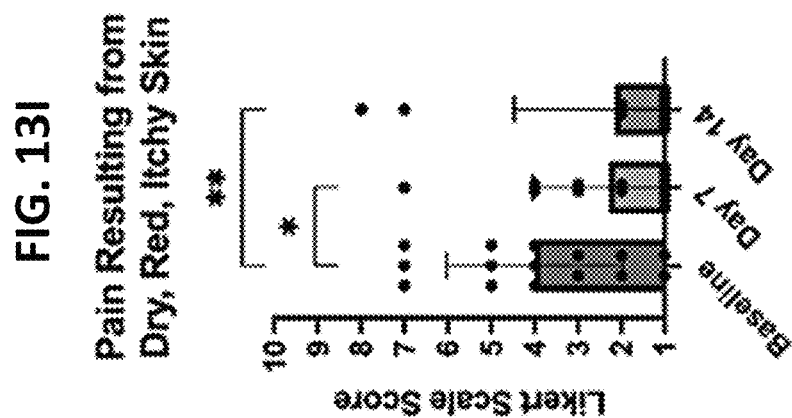
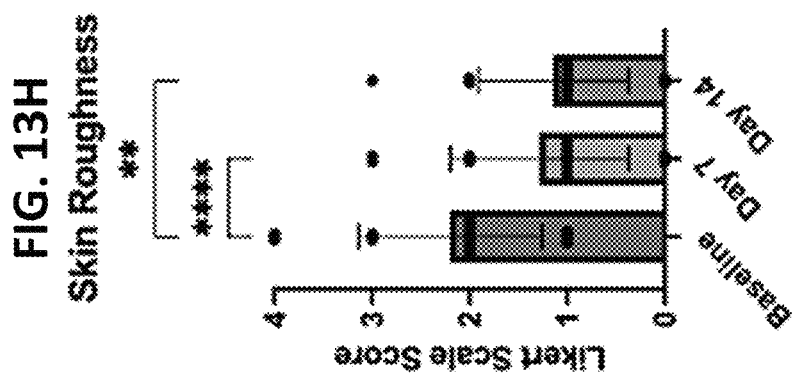
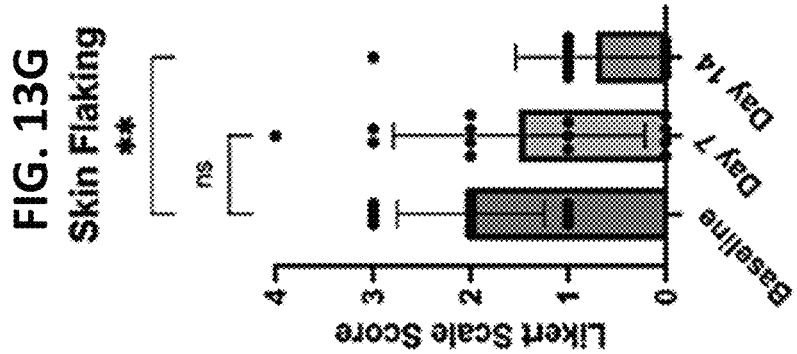

FIG. 14B

FIG. 14C

RECOMBINANT CELL WALL HYDROLASES

CROSS-REFERENCE TO RELATED APPLICATIONS

This application is a continuation of International Application No. PCT/US2024/034521, filed Jun. 18, 2024, which claims the benefit of and priority to U.S. Provisional Patent Application No. 63/639,416, filed Apr. 26, 2024, and U.S. Provisional Patent Application No. 63/509,160, filed Jun. 20, 2023, the contents of each of which are incorporated by reference herein in their entireties.

INCORPORATION OF THE SEQUENCE LISTING

The contents of the text file submitted electronically herewith are incorporated herein by reference in their entirety: A computer readable format copy of the Sequence Listing (Filename: TOPB_002_02WO_SeqList_ST26.xml; Size: 43,050 bytes; and Date of Creation: Jun. 17, 2024).

FIELD OF THE DISCLOSURE

The present disclosure relates to novel recombinant cell wall hydrolases. The disclosure also relates to compositions comprising these cell wall hydrolases.

BACKGROUND

*Staphylococcus* is a genus of gram-positive bacteria in the family Staphylococcaceae from the order Bacillales. This genus includes at least 43 species, many of which do not cause disease and reside on the skin and mucous membranes of humans and other animals. However, some species of *Staphylococcus*, including *Staphylococcus aureus*, are pathogenic and can cause infections that are particularly dangerous to immunocompromised subjects. *Staphylococcus aureus* is a leading agent of sepsis. Within the skin microbiome, overgrowth of *Staphylococcus aureus* is strongly associated with moderate to severe cases of atopic dermatitis as well as acute radiation dermatitis.

While antibiotics may be used to treat bacterial infection, many *Staphylococcus* strains are antibiotic resistant, making them very difficult to manage. In addition, antibiotics or chemicals like benzoyl peroxide can negatively affect commensal bacterial populations, as well as pathogenic ones.

There is an ongoing an unmet need for new therapeutics active against *Staphylococcus* sp.

BRIEF SUMMARY

The present disclosure teaches chimeric cell wall hydrolases (CWH) with desirable properties. In some embodiments, the CWHs of the present disclosure are capable of selectively treating *S. aureus* infections.

In one aspect, the present disclosure provides a chimeric cell wall hydrolase (CWH) comprising: a) an enzymatically active domain (EAD) having at least 80, 81, 82, 83, 84, 85, 86, 87, 88, 89, 90, 91, 92, 93, 94, 95, 96, 97, 98, 99, or 100% identity with SEQ ID NO: 11; and b) a cell wall binding domain (CBD) having at least 80, 81, 82, 83, 84, 85, 86, 87, 88, 89, 90, 91, 92, 93, 94, 95, 96, 97, 98, 99, or 100% identity with the sequence of: i) SEQ ID NO: 16; ii) SEQ ID NO: 17; or iii) SEQ ID NO: 18.

In one aspect, the present disclosure provides a chimeric cell wall hydrolase (CWH) comprising a sequence having at least 80, 81, 82, 83, 84, 85, 86, 87, 88, 89, 90, 91, 92, 93, 94, 95, 96, 97, 98, 99, or 100% identity with SEQ ID NO: 22.

In one aspect, the present disclosure provides a chimeric cell wall hydrolase (CWH) comprising a sequence having at least 80, 81, 82, 83, 84, 85, 86, 87, 88, 89, 90, 91, 92, 93, 94, 95, 96, 97, 98, 99, or 100% identity with SEQ ID NO: 24.

In one aspect, the present disclosure provides a topical formulation comprising a chimeric CWH of the disclosure.

In one aspect, the present disclosure provides a topical formulation comprising a chimeric cell wall hydrolase (CWH) comprising a sequence having at least 80, 81, 82, 83, 84, 85, 86, 87, 88, 89, 90, 91, 92, 93, 94, 95, 96, 97, 98, 99, or 100% identity with SEQ ID NO: 21.

In one aspect, the present disclosure provides a method of treating a condition associated with *Staphylococcus*, the method comprising the step of: administering a composition comprising a chimeric CWH of the disclosure.

BRIEF DESCRIPTION OF THE SEVERAL VIEWS OF THE DRAWINGS

The accompanying figures, which are incorporated herein and form a part of the specification, illustrate some, but not the only or exclusive, example embodiments and/or features. It is intended that the embodiments and figures disclosed herein are to be considered illustrative rather than limiting.

FIG. 3 contains two tables summarizing the MIC and selectivity results of FIG. 1 and FIG. 2.

FIG. 7A-7B show turbidity reduction assay results for SA.100 vs. the LysSA12 EAD+PlySs2 CBD chimera against *S. aureus*. FIG. 7A shows the turbidity reduction assay results, while FIG. 7B shows relative activity as calculated from the turbidity reduction assay.

FIG. 11A-11C show the activity against *S. aureus* and *S. epidermidis* of the LysSA12 EAD+PlySs2 CBD chimera in several topical formulations: formulation #1 comprising hyaluronic acid (FIG. 11A), formulation #2 comprising hydroxymethylcellulose (FIG. 11B), and formulation #3, a cream-based formula (FIG. 11C). Control formulations are identical to the test formulation, but do not contain LysSA12 EAD+PlySs2 CBD protein.

FIG. 13A-13I show the results of LysSA12 EAD+PlySs2 CBD chimera application to dry, red, itchy skin in terms of: skin itchiness (FIG. 13A), days of skin itchiness (FIG. 13B), sleeplessness (FIG. 13C), frequency of sleep disturbed by skin (FIG. 13D), skin redness (FIG. 13E), skin dryness (FIG. 13F), skin flaking (FIG. 13G), skin roughness (FIG. 13H), and pain resulting from dry, red, itchy skin (FIG. 13I). The charts show the group mean with standard deviation; individual data points are also plotted. "ns" indicates $p>0.05$; * indicates $p<0.05$;  indicates $p<0.01$; * indicates $p<0.001$; and **** indicates $p<0.0001$.

FIG. 14A-14C show representative face (FIG. 14A), palm (FIG. 14B), and elbow (FIG. 14C) images before and after 14-day treatment with a LysSA12 EAD+PlySs2 CBD chimera composition.

DETAILED DESCRIPTION

Figure 1:
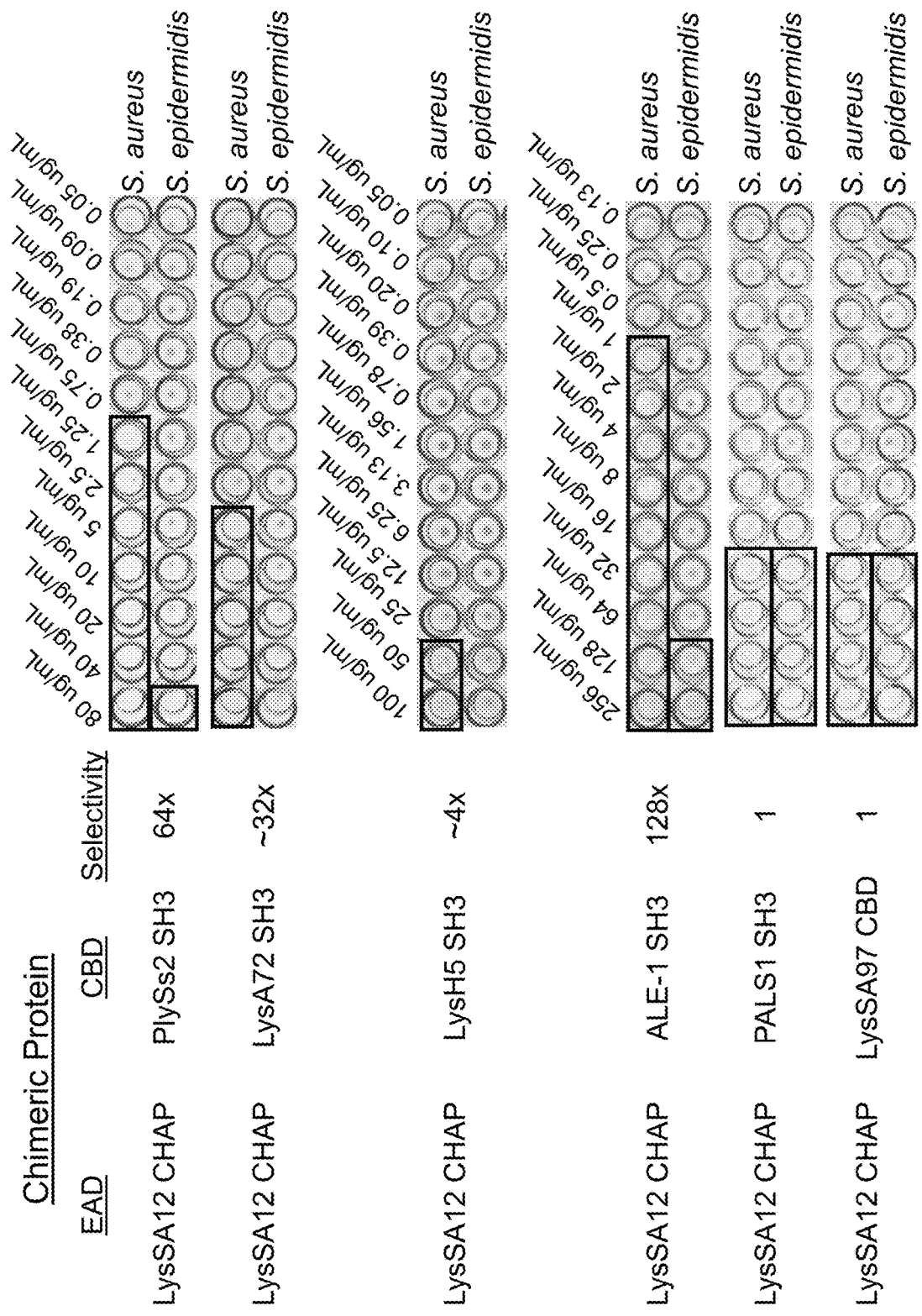
FIG. 1 shows Minimum Inhibitory Concentration (MIC) assay results against *Staphylococcus aureus* and *Staphylococcus epidermidis* for chimeric cell wall hydrolases comprising the LysSA12 CHAP domain fused to 6 different CBDs. Boxes indicate growth inhibition.

All publications, patents and patent applications, including any drawings and appendices, are herein incorporated by reference to the same extent as if each individual publication or patent application was specifically and individually indicated to be incorporated by reference.

The following description includes information that may be useful in understanding the present disclosure. It is not an admission that any of the information provided herein is prior art, or that any publication specifically or implicitly referenced is prior art.

Definitions

The term "a" or "an" refers to one or more of that entity, i.e. can refer to plural referents. As such, the terms "a," "an," "one or more," and "at least one" are used interchangeably herein. In addition, reference to "an element" by the indefinite article "a" or "an" does not exclude the possibility that more than one of the elements is present, unless the context clearly requires that there is one and only one of the elements.

Throughout this application, the term "about" is used to indicate that a value includes the inherent variation of error for the device or the method being employed to determine the value, or the variation that exists among the samples being measured. Unless otherwise stated or otherwise evident from the context, the term "about" means within 10% above or below the reported numerical value (except where such number would exceed 100% of a possible value or go below 0%). When used in conjunction with a range or series of values, the term "about" applies to the endpoints of the range or each of the values enumerated in the series, unless otherwise indicated. As used in this application, the terms "about" and "approximately" are used as equivalents.

As used herein, the term "cell wall hydrolase" or "CWH" refers to bacterial cell wall hydrolases, which are enzymes that degrade peptidoglycan in bacterial cell walls by cleaving bonds in the peptidoglycan chain and side-chain branches. These terms also encompass any recombinant enzymes of the disclosure having the activity of a cell wall hydrolase. Cell wall hydrolases may have different domain architectures. CWHs comprise an "enzymatically active domain" or "EAD," which is a domain responsible for degrading peptidoglycan. In some embodiments, the EAD has glycosidase, amidase, and/or peptidase enzymatic activity. In some embodiments, CWHs comprise a "cell wall binding domain" or "CBD", which is a domain that binds to a bacterial cell wall.

A "native" protein is used to indicate a protein that occurs in nature and has not been artificially modified or recombined.

The term "recombinant" is used herein to describe nucleic acids, proteins, vectors, and host cells which do not occur in nature or, in the context of nucleic acids, are in an arrangement not found in nature. A "recombinant protein" therefore refers to a protein which does not occur in nature. In some embodiments, recombinant protein, as used herein, refers to a chimeric protein. In some embodiments, recombinant protein refers to the expression product of any of the presently disclosed EAD or CBD sequences alone, or within a protein that does not occur in nature. For example, the present disclosure envisions recombinant EAD or CBD sequences of the disclosure fused to any protein tags, such as 6×His.

As used herein, "heterologous" refers to any genetic material that is artificially introduced into a non-native context. E.g., a heterologous domain refers to a domain, such as an EAD or CBD, that is artificially introduced into a recombinant protein sequence, wherein the resulting recombinant protein sequence is non-native.

As used herein, a "chimeric protein" is any recombinant protein comprising two or more heterologous domains, e.g., EADs and/or CBDs.

As used herein, a "domain" of a protein is a functional and/or structural subunit in a protein. In some embodiments, they are responsible for a particular function or interaction, contributing to the overall role of a protein. Protein domains are fundamental units of protein structure, folding, function, evolution and design. See, e.g., Wang et al., "Protein domain identification methods and online resources," *Comput Struct Biotechnol J* 2021; 19:1145-1153, incorporated by reference herein.

As used herein, a "chimeric cell wall hydrolase" or "chimeric CWH" is a chimeric protein that acts as a cell wall hydrolase and comprises at least one heterologous domain, e.g., a heterologous EAD or CBD, compared to a native CWH sequence. A chimeric CWH also refers herein to a recombinant protein comprising two heterologous CWH domains, e.g., an EAD and a CBD.

As used herein, "activity" refers to the ability of a protein (e.g., a chimeric CWH protein) to inhibit the growth of and/or lyse a cell from a *Staphylococcus* species. The term "active against", as used herein with reference to a target species of *Staphylococcus*, refers to a protein (e.g., a chimeric CWH protein of the disclosure) that is able to inhibit the growth of and/or lyse cells belonging to that target species of *Staphylococcus*. Activity can be calculated in different ways, depending on the assay performed. In some embodiments, level of activity is indicated based on minimum inhibitory concentration ("MIC"), e.g., the minimum concentration of the protein required to prevent growth of the target *Staphylococcus* species in an MIC assay. In some embodiments, level of activity is indicated based on turbidity reduction, e.g., with activity calculated as $-\Delta OD_{600}$/min/(mg of enzyme). In some embodiments, activity is indicated based on the decrease in viable bacterial cells in a culture after a period of incubation (e.g., 2 hours) with a protein.

In the context of anti-*Staphylococcus* activity, the terms "selective" and "selectivity" as used herein refer to the property of showing higher activity toward one target species of *Staphylococcus* in comparison to a second species of *Staphylococcus*. Selectivity can be calculated by comparing the inverse of the MIC of a chimeric protein toward a first species to the MIC of the protein toward a second species. In some embodiments, selectivity is determined based on relative activity in a turbidity reduction assay.

As used herein the term "sequence identity" refers to the extent to which two optimally aligned polynucleotides or polypeptide sequences are invariant throughout a window of alignment of residues, e.g. nucleotides or amino acids. An "identity fraction" for aligned segments of a test sequence and a reference sequence is the number of identical residues which are shared by the two aligned sequences divided by the total number of residues in the reference sequence segment, i.e. the entire reference sequence or a smaller defined part of the reference sequence. "Percent identity" is the identity fraction times 100. Comparison of sequences to determine percent identity can be accomplished by a number of well-known methods, including for example by using mathematical algorithms, such as, for example, those in the BLAST suite of sequence analysis programs. Unless noted otherwise, the term "sequence identity" in the claims refers to sequence identity as calculated by MUSCLE (www.ebi.ac.uk/Tools/msa/muscle/) using default parameters.

As used herein, the term "w/v" refers to the concentration of an ingredient within a composition as measured by the weight or mass of the ingredient compared to the volume of the composition. The weight of the solute is often provided in grams while the volume is often provided in milliliters, with the resulting value provided as a percentage.

Overview

The present disclosure provides novel chimeric cell wall hydrolases (CWHs). Also provided herein are compositions comprising the chimeric CWHs, and uses thereof in targeting *Staphylococcus* sp. and treating conditions associated with *Staphylococcus* sp.

The present disclosure is related, in part, to the growing appreciation for the critical role that the skin microbiome plays in skin health and skin function. Among other benefits, a healthy microbiome helps to prevent colonization by pathogenic microbes, train the immune system and prevent inflammation, reinforce the skin barrier, and promote wound healing. Dysbiosis of the skin microbiome can cause and/or exacerbate skin diseases like atopic dermatitis and acne vulgaris. For example, overgrowth of *Staphylococcus aureus* is strongly associated with moderate to severe cases of atopic dermatitis as well as acute radiation dermatitis.

Current therapeutic tools do not allow for precision treatment of skin diseases. Common approaches like topical/oral antibiotics or chemicals like benzoyl peroxide are used to target causal bacteria but also negatively affect the global skin microbiome. In other cases, long term steroid use can lead to unwanted and severe side effects.

The present disclosure provides compositions and treatments for *Staphylococcus* infection based on the identification of novel chimeric cell wall hydrolases (CWHs). CWHs are enzymes that degrade bacterial peptidoglycan by cleaving bonds in the peptidoglycan chain and side-chain branches. Degradation of peptidoglycan cell walls by CWHs can result in rapid lysis of a bacterial cell due to an inability to resist internal turgor pressure.

As demonstrated in the Examples herein, the present disclosure provides novel and highly effective chimeric CWHs. These chimeric CWHs have high lytic activity and/or *Staphylococcus* species-specificity. In some embodiments, the chimeric CWH is composed of domains from parent proteins and has properties that are superior to any of the parent proteins. In some embodiments, CWHs herein bind very specific epitopes in target cell walls. In some embodiments, CWHs herein have lytic activity down to a single species or group of related species. Because of these properties, in some embodiments, the CWHs herein act as high-specificity skin microbiome modulators. For example, in the case of atopic dermatitis or acute radiation dermatitis, in some embodiments, CWHs herein are able to specifically kill *Staphylococcus aureus*, while exhibiting significantly less activity against healthy, commensal bacteria.

Chimeric Cell Wall Hydrolases of the Disclosure

The present disclosure is based on the inventors' development of novel and highly active chimeric CWHs. As disclosed in the Examples herein, illustrative CWHs of the disclosure are surprising in that they have highly effective anti-*Staphylococcus* properties that arise from the unique combination of CBD and EAD comprised by the CWH.

In some embodiments, the present disclosure provides a recombinant protein comprising the sequence of an EAD and/or CBD according to any one of the embodiments disclosed herein. In some embodiments, the recombinant protein is a chimeric protein. In some embodiments, the chimeric protein is a chimeric cell wall hydrolase (CWH).

A chimeric CWH herein comprises at least one heterologous domain, e.g., a heterologous EAD or CBD, compared to a native CWH sequence. In some embodiments, a chimeric CWH herein is a chimeric protein comprising an EAD and a CBD from different proteins.

Enzymatically Active Domains (EADs)

In some embodiments, a chimeric protein of the disclosure comprises an EAD. In some embodiments, the EAD is derived from *Staphylococcus* phage SA12, phiPLA35, Twort, CSA13, CSA5, phiH5, or SA97. In some embodiments, the EAD is derived from Prophage in *Streptococcus suis* strain 89/1591. In some embodiments, the EAD is derived from *Staphylococcus capitis*. In some embodiments, the EAD is derived from LysSA12, LysA72, PlySs2, Twort, LysCSA13, LysCSA5, LysH5, ALE-1, LysSA97, or LysPALS1. In some embodiments, the EAD is derived from LysSA12, Twort, LysCSA13, or LysCSA5. In some embodiments, the EAD is derived from LysSA12. The term "derived" in the context of describing the source of an EAD or CBD indicates that the domain is contained within the referenced protein. Thus, an EAD that is derived from LysSA12 is contained within the native LysSA12 endolysin protein.

In some embodiments, the EAD consists of SEQ ID NO: 11, 12, 13, or 14. In some embodiments, the EAD comprises the sequence of SEQ ID NO: 11, 12, 13, or 14. In some embodiments, the EAD has at least 80, 81, 82, 83, 84, 85, 86, 87, 88, 89, 90, 91, 92, 93, 94, 95, 96, 97, 98, 99, or 100% identity with SEQ ID NO: 11, 12, 13, or 14. In some embodiments, the EAD differs from the sequence of SEQ ID NO: 11, 12, 13, or 14 by 1, 2, 3, 4, 5, 6, 7, 8, 9, 10, 11, 12, 13, 14, or 15 amino acids.

In some embodiments, the EAD consists of SEQ ID NO: 11. In some embodiments, the EAD comprises the sequence of SEQ ID NO: 11. In some embodiments, the EAD has at least 80, 81, 82, 83, 84, 85, 86, 87, 88, 89, 90, 91, 92, 93, 94, 95, 96, 97, 98, 99, or 100% identity with SEQ ID NO: 11. In some embodiments, the EAD differs from the sequence of SEQ ID NO: 11 by 1, 2, 3, 4, 5, 6, 7, 8, 9, 10, 11, 12, 13, 14, or 15 amino acids.

```
The sequence of SEQ ID NO: 11 is as follows:
MQAKLTKKEFIEWLKTSEGKQYNADGWYGFQCFDYANAGWQVLFGYNLK

GVGAKDIPSANDFNGLATVYQNTPDFLAQPGDMVVFGSNYGAGYGHVAW

VIEATLDYIIVYEQNWLGGGWTDGVQQPGSGWEKVTRRQHAYDFPMWFI

RPNFKSETAPRSVQSPTQASKKET.
```

In some embodiments, the EAD consists of a sequence contained in Table 1. In some embodiments, the EAD comprises a sequence contained in Table 1. In some embodiments, the EAD has at least 80, 81, 82, 83, 84, 85, 86, 87, 88, 89, 90, 91, 92, 93, 94, 95, 96, 97, 98, 99, or 100% identity with a sequence contained in Table 1. In some embodiments, the EAD differs by 1, 2, 3, 4, 5, 6, 7, 8, 9, 10, 11, 12, 13, 14, or 15 amino acids from a sequence contained in Table 1.

TABLE 1

Illustrative EAD Sequences of the Disclosure.

| Sequence Description | SEQ ID NO | Amino Acid Sequence |
|---|---|---|
| LysSA12 EAD | 11 | MQAKLTKKEFIEWLKTSEGKQYNADGWYGFQCFDYAN AGWQVLFGYNLKGVGAKDIPSANDFNGLATVYQNTPD FLAQPGDMVVFGSNYGAGYGHVAWVIEATLDYIIVYEQ NWLGGGWTDGVQQPGSGWEKVTRRQHAYDFPMWFIR PNFKSETAPRSVQSPTQASKKET |
| Twort EAD | 12 | MKTLKQAESYIKSKVNTGTDFDGLYGYQCMDLAVDYIY HVTDGKIRMWGNAKDAINNSFGGTATVYKNYPAFRPK YGDVVVWTTGNFATYGHIAIVTNPDPYGDLQYVTVLEQ NWNGNGIYKTELATIRTHDYTGITHFIRPNFATESSVKKK DTKKKPKPSNRDG |
| LysCSA13 EAD | 13 | MKSQKQAKQWIDVNTGKGVDFDGAYGFQCMDLAVAY VYYITDGKVRMWGNAKDAINNDFKGLATVYENTPRFK PQLGDVAVYTNSQYGHIQVVISGNLDYYTCLEQNWLNG GYDGWEKATIRTHYYDGVTHFIRPKFSDSNSQV |
| LysCSA5 EAD | 14 | MAKTQAEINKRLDAYAKGTVDSPYRIKKATSYDPSFGV MEAGAIDADGYYHAQCQDLITDYVLWLTDNKVRTWGN AKDQIKQSYGTGFKIHENKPSTVPKKGWIAVFTSGSYQQ WGHIGIVYDGGNTSTFTILEQNWNGYANKKPTKRVDNY YGLTHFIEIPVKAGTTVKKETAKKSA |

In some embodiments, the CWH comprises an EAD derived from a lysin. In some embodiments, the lysin is an endolysin, a tail lysin, an exolysin, a bacteriocin, or an autolysin. In some embodiments, the EAD is derived from any one of the endolysins listed herein. In some embodiments, the EAD is a glycosidase. In some embodiments, the EAD is an amidase. In some embodiments, the EAD is a peptidase. In some embodiments, the EAD is a CHAP domain. In some embodiments, the EAD is an M23 domain.

In some embodiments, the chimeric CWH comprises an EAD according to any one of the foregoing embodiments.

In some embodiments, the chimeric CWH comprises 1 EAD. In some embodiments, the CWH comprises more than one EAD. In some embodiments, the chimeric CWH comprises 2 EADs. In some embodiments, the chimeric CWH comprises 3, 4, 5, 6, 7, 8, 9, or 10 EADs.

Cell Wall Binding Domains (CBDs)

In some embodiments, the chimeric CWH comprises a cell wall binding domain (CBD). In some embodiments, the CBD is derived from a *Staphylococcus* phage protein. In some embodiments, the CBD is derived from a *Staphylococcus* phage CWH. In some embodiments, the CBD is derived from a *Staphylococcus* phage lysin. In some embodiments, the lysin is an endolysin, a tail lysin, an exolysin, a bacteriocin, or an autolysin. In some embodiments, the CBD is an SH3b domain.

In some embodiments, the CBD is derived from *Staphylococcus* phage SA12, phiPLA35, Twort, CSA13, CSA5, phiH5, or SA97. In some embodiments, the CBD is derived from Prophage in *Streptococcus suis* strain 89/1591. In some embodiments, the CBD is derived from *Staphylococcus capitis*. In some embodiments, the CBD is derived from LysSA12, LysA72, PlySs2, Twort, LysCSA13, LysCSA5, LysH5, ALE-1, LysSA97, or LysPALS1. In some embodiments, the CBD is derived from LysH5, LysA72, PlySs2, ALE-1, LysSA97, or LysPALS1. In some embodiments, the CBD is derived from PlySs2, LysA72, or ALE-1.

In some embodiments, the CBD consists of SEQ ID NO: 15, 16, 17, 18, 19, or 20. In some embodiments, the CBD comprises the sequence of SEQ ID NO: 15, 16, 17, 18, 19, or 20. In some embodiments, the CBD has at least 80, 81, 82, 83, 84, 85, 86, 87, 88, 89, 90, 91, 92, 93, 94, 95, 96, 97, 98, 99, or 100% identity with SEQ ID NO: 15, 16, 17, 18, 19, or 20. In some embodiments, the CBD differs from the sequence of SEQ ID NO: 15, 16, 17, 18, 19, or 20 by 1, 2, 3, 4, 5, 6, 7, 8, 9, 10, 11, 12, 13, 14, or 15 amino acids.

In some embodiments, the CBD consists of SEQ ID NO: 16, 17, or 18. In some embodiments, the CBD comprises the sequence of SEQ ID NO: 16, 17, or 18. In some embodiments, the CBD has at least 80, 81, 82, 83, 84, 85, 86, 87, 88, 89, 90, 91, 92, 93, 94, 95, 96, 97, 98, 99, or 100% identity with SEQ ID NO: 16, 17, or 18. In some embodiments, the CBD differs from the sequence of SEQ ID NO: 16, 17, or 18 by 1, 2, 3, 4, 5, 6, 7, 8, 9, 10, 11, 12, 13, 14, or 15 amino acids.

```
The sequence of SEQ ID NO: 16 (LysA72 CBD) is
as follows:
KNPPVPAGYTLDKNNVPYKKEAGNYTVANVKGNNVRDGYSTNSRITGV

LPNNATIKYDGAYCINGYRWITYIANSGQRRYIATGEVDKAGNRISSF

GKFSTI.

The sequence of SEQ ID NO: 17 (PlySs2 CBD) is
as follows:
SRSYRETGTMTVTVDALNVRRAPNTSGEIVAVYKRGESFDYDTVIIDV

NGYVWVSYIGGSGKRNYVATGATKDGKRFGNAWGTFK

The sequence of SEQ ID NO: 18 (ALE-1 CBD) is
as follows:
MPFLKSAGYGSNSTSSSNNNGYKTNKYGTLYKSESASFTANTDIITRL

TGPFRSMPQSGVLRKGLTIKYDEVMKQDGHVWVGYNTNSGKRVYLPVR

TWNESTGELGPLWGTIK.
```

In some embodiments, the CBD consists of a sequence contained in Table 2. In some embodiments, the CBD comprises a sequence contained in Table 2. In some embodiments, the CBD has at least 80, 81, 82, 83, 84, 85, 86, 87, 88, 89, 90, 91, 92, 93, 94, 95, 96, 97, 98, 99, or 100% identity with a sequence contained in Table 2. In some embodiments, the CBD differs by 1, 2, 3, 4, 5, 6, 7, 8, 9, 10, 11, 12, 13, 14, or 15 amino acids from a sequence contained in Table 2.

TABLE 2

Illustrative CBD sequences of the disclosure.

| CBD Description | SEQ ID NO | Sequence |
|---|---|---|
| LysH5 CBD | 15 | SNDSSASSNTVKPVASAWKRNKYGTYYMEESARFT NGNQPITVRKVGPFLSCPVGYQFQPGGYCDYTEVM LQDGHVWVGYTWEGQRYYLPIRTWNGSAPPNQILG DLWGEIS |
| LysA72 CBD | 16 | KNPPVPAGYTLDKNNVPYKKEAGNYTVANVKGNNV RDGYSTNSRITGVLPNNATIKYDGAYCINGYRWIT YIANSGQRRYIATGEVDKAGNRISSFGKFSTI |
| PlySs2 CBD | 17 | SRSYRETGTMTVTVDALNVRRAPNTSGEIVAVYKR GESFDYDTVIIDVNGYVWVSYIGGSGKRNYVATGA TKDGKRFGNAWGTFK |
| ALE-1 CBD | 18 | MPFLKSAGYGSNSTSSSNNNGYKTNKYGTLYKSES ASFTANTDIITRLTGPFRSMPQSGVLRKGLTIKYD EVMKQDGHVWVGYNTNSGKRVYLPVRTWNESTGEL GPLWGTIK |
| LysSA97 CBD | 19 | PSSKPSADKITWNWKGVFYPNPEKAIRVRKTAGLT GTVVEEDSWLYTKDDWVKFDQVIKKDGYWWIRFKY QREGSSTNNFYCAVCRITDKEQKIKNEKYWGTIEW A |
| LysPALS1 CBD | 20 | SASTPATRPVTGSWKKNQYGTWYKPESATFVNGNQ PIVTRIGSPFLNAPVGGNLPAGATIVYDEVCIQAG HIWIGYNAYNGNRVYCPVRTCQGVPPSHVPGVAWG TFK |

In some embodiments, the chimeric CWH comprises a CBD according to any one of the foregoing embodiments.

In some embodiments, the chimeric CWH comprises 1 CBD. In some embodiments, the CWH comprises more than one CBD. In some embodiments, the chimeric CWH comprises 2 CBDs. In some embodiments, the chimeric CWH comprises 3, 4, 5, 6, 7, 8, 9, or 10 CBDs.

Linkers

In some embodiments, a chimeric protein herein comprises more than one domain, and the domains are joined by a linker. In some embodiments, the linker is a flexible linker. In some embodiments, the linker is an amino acid sequence between 1-100 amino acids in length, including all values and subranges therebetween. In some embodiments, the linker comprises one or more glycines and/or serines.

Protein Tags

In some embodiments, a recombinant protein of the disclosure comprises a protein tag. A protein tag is typically a short sequence of amino acids, or a protein domain, that is fused to a recombinant protein in order to facilitate purification and/or visualization. In some embodiments, a protein tag improves protein solubility. In some embodiments, the tag is a His tag, a GST tag, an MBP tag, a Strep tag, a FLAG tag, a GFP tag, an HA tag, a V5 tag, an Avi tag, a CBP tag, a ZZ tag, a SUMO tag, an Fc tag, a Thioredoxin tag, a Protein kinase A (PKA) tag, a Myc tag, or an S tag, or any combination thereof. In some embodiments, the tag is a His tag and comprises 6 histidine residues.

Nucleic Acids, Vectors, and Host Cells of the Disclosure

The present disclosure also provides nucleic acids encoding the chimeric proteins, e.g., CWHs, of the disclosure. The present disclosure also provides vectors and host cells for expression of the chimeric proteins of the disclosure. In some embodiments, the vector is a plasmid, a cosmid, a bacteriophage, or a virus comprising a nucleic acid of the disclosure. In some embodiments, the host cell comprises a nucleic acid of the disclosure or a vector of the disclosure. In some embodiments, the host cell is a bacterial cell, a yeast cell, an insect cell, a mammalian cell, or a plant cell.

Formulations of the Disclosure

The present disclosure provides compositions comprising the novel chimeric proteins (e.g., CWHs), nucleic acids, vectors, or host cells disclosed herein. In some embodiments, these compositions are formulated for delivery to a subject for the treatment of a condition associated with *Staphylococcus* sp.

Topical, Parenteral, and Enteral Formulations

In some embodiments, compositions of the disclosure are formulated for topical, parenteral, or enteral administration.

In some embodiments, a composition herein is formulated for topical administration. Formulations for topical administration include lotions, hydrogels, creams, ointments, gels, drops, transdermal patches, colloidal patches, powders, suppositories, sprays, liquids, semi-solids, monophasic compositions, multiphasic compositions (e.g., oil-in-water, water-in-oil), foams, microsponges, liposomes, nanoemulsions, aerosol foams, polymers, fullerenes, and powders. In some embodiments, carriers, bases, thickeners, penetration enhancers, buffers, diluents, emulsifiers, humectants, dispersing aids, binders, and/or excipients are added to the formulation. In some embodiments, the composition is formulated as a hydrogel. In some embodiments, the composition is formulated as a lotion. In some embodiments, the composition is formulated as a cream. In some embodiments, the composition is formulated as a freeze dried powder, e.g., which can be reconstituted with liquid prior to use. In some embodiments, the composition is a colloidal patch.

In some embodiments, the compositions of the disclosure are formulated for parenteral administration. As used herein, "parenteral administration" of a composition includes any route of administration characterized by physical breaching of a tissue of a subject and administration of the composition through the breach in the tissue, thus generally resulting in the direct administration into the blood stream, into muscle, or into an internal organ. Parenteral administration thus includes, but is not limited to, administration of a composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal, intravenous, intraarterial, intrathecal, intraventricular, intraurethral, intracranial, intratumoral, intrasynovial injection or infusions; and kidney dialytic infusion techniques.

In some embodiments, a composition herein is prepared for oral administration. The terms "oral", "enteral", "enterally", "orally", "non-parenteral", "non-parenterally", and the like, refer to administration of a compound or composition to an individual by a route or mode along the alimentary canal. Examples of "oral" routes of administration of a composition include, without limitation, swallowing liquid or solid forms of a composition from the mouth, administration of a composition through a nasojejunal or gastrostomy tube, intraduodenal administration of a composition, and rectal administration, e.g., using suppositories for the lower intestinal tract of the alimentary canal. The compositions of the present disclosure may be formulated into any of many possible dosage forms such as, but not limited to, tablets, capsules, liquid syrups, soft gels, suppositories, aerosols, and enemas. The compositions of the present disclosure may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

Formulation Ingredients

In some embodiments, the composition comprises an emulsifier. In some embodiments, the composition comprises a mixture of emulsifiers.

In some embodiments, the composition comprises about 0.5% to about 5% w/v of an emulsifier or a mixture of emulsifiers.

Examples of emulsifiers suitable for use in some embodiments of the disclosure include xanthan gum, polysorbate 80, oleoyl polyoxyl-6 glycerides, polyoxyl 35 hydrogenated castor oil, sucrose distearate, saponin, sodium alginate, guar gum, tocopherol polyethylene glycol 1000 succinate, lauroyl polyoxyl-32 glycerides, sorbitan monooleate, glyceryl stearate, cetearyl alcohol, sodium stearoyl lactylate, salts thereof, derivatives thereof, and mixtures thereof. In some embodiments, the emulsifier is xanthan gum.

In some embodiments, emulsifier components are selected from poly-glycolized glycerides and polyoxyethylene glycerides of medium to long chain mono-, di-, and triglycerides, such as: almond oil PEG-6 esters, almond oil PEG-60 esters, apricot kernel oil PEG-6 esters (Labrafil® M1944CS), caprylic/capric triglycerides PEG-4 esters (Labrafac® Hydro WL 1219), caprylic/capric triglycerides PEG-4 complex (Labrafac® Hydrophile), caprylic/capric glycerides PEG-6 esters (Softigen® 767), caprylic/capric glycerides PEG-8 esters (Labrasol®), castor oil PEG-50 esters, hydrogenated castor oil PEG-5 esters, hydrogenated castor oil PEG-7 esters, 9 hydrogenated castor oil PEG-9 esters, corn oil PEG-6 esters (Labrafil® M 2125 CS), corn oil PEG-8 esters (Labrafil® WL 2609 BS), corn glycerides PEG-60 esters, olive oil PEG-6 esters (Labrafil® M1980 CS), hydrogenated palm/palm kernel oil PEG-6 esters (Labrafil® M 2130 BS), hydrogenated palm/palm kernel oil PEG-6 esters with palm kernel oil, PEG-6, palm oil (Labrafil® M 2130 CS), palm kernel oil PEG-40 esters, peanut oil PEG-6 esters (Labrafil® M 1969 CS), glycerol esters of saturated C8-C18 fatty acids (Gelucire® 33/01), glyceryl esters of saturated C12-C18 fatty acids (Gelucire® 39/01 and 43/01), glyceryl laurate/PEG-32 laurate (Gelucire® 44/14), glyceryl laurate glyceryl/PEG 20 laurate, glyceryl laurate glyceryl/PEG 32 laurate, glyceryl, laurate glyceryl/PEG 40 laurate, glyceryl oleate/PEG-20 glyceryl, glyceryl oleate/PEG-30 oleate, glyceryl palmitostearate/PEG-32 palmitostearate (Gelucire® 50/13), glyceryl stearate/PEG stearate, glyceryl stearate/PEG-32 stearate (Gelucire® 53/10), saturated polyglycolized glycerides (Gelucire® 37/02 and Gelucire® 50/02), triisostearin PEG-6 esters (i.e. Labrafil® Isostearique), triolein PEG-6 esters, trioleate PEG-25 esters, polyoxyl 35 castor oil (Cremophor® EL or Kolliphor® EL), polyoxyl 40 hydrogenated castor oil (Cremophor® RH 40 or Kolliphor® RH40), polyoxyl 60 hydrogenated castor oil (Cremophor® RH60), lecithin, phospholipids and mixtures thereof.

In some embodiments, the emulsifier is polyglycolized derivatives and polyoxyethylene esters or ethers derivatives of medium to long chain fatty acids, commercially named Brij and Myrj variety surfactants, and propylene glycol esters of medium to long chain fatty acids, which can be used including caprylate/caprate diglycerides, glyceryl monooleate, glyceryl ricinoleate, glyceryl laurate, glyceryl dilaurate, glyceryl dioleate, glyceryl mono/dioleate, glyceryl caprylate/caprate, medium chain (C8/C10) mono- and diglycerides (Capmul® MCM, Capmul® MCM (L)), mono- and diacetylated monoglycerides, polyglyceryl oleate, polyglyceryl-2 dioleate, polyglyceryl-10 trioleate, polyglyceryl-10 laurate, polyglyceryl-10 oleate, and polyglyceryl-10 mono dioleate, propylene glycol caprylate/caprate (Labrafac® PC), propylene glycol dicaprylate/dicaprate (Miglyol® 840), propylene glycol monolaurate, propylene glycol ricinoleate, propylene glycol monooleate, propylene glycol dicaprylate/dicaprate, propylene glycol dioctanoate, and mixtures thereof.

In some embodiments, the composition comprises a humectant. In some embodiments, the composition is a topical formulation and comprises a humectant, which can be referred to as a soothing, smoothing, moisturizing, or protective agent. Humectants of the present disclosure function to stabilize the moisture content of the tissue to which it is applied in the presence of fluctuating humidity.

In some embodiments, the humectant is selected from: polyglycols (as hereinafter defined), propylene glycol, sorbitol, lactic acid, sodium lactate, glycerol, glycerine, ethoxylated castor oil, calamine, dodecylsulphate, sodium lauryl sulphate (SLS); a polyoxyethylene ester of polysorbitan, such as monooleate, monolaurate, monopalmitate, monostearate esters; esters of sorbitan, the polyoxyethylenes ethers, sodium dioctylsulphosuccinate (DOSS), lecithin, sodium docusate, hexylene glycol, butylene glycol, aloe vera gel, aloe vera powder, hyaluronic acid, alpha hydroxy acids such as lactic acid, egg yolk, egg white, glyceryl triacetate, honey, molasses, polymeric polyols such as polydextrose, quillaia, sodium hexametaphosphate e452i; sugar alcohols (sugar polyols) such as glycerol, sorbitol, xylitol, maltitol; urea, and castor oil.

In some embodiments, the composition comprises a humectant selected from the list consisting of: aloe vera, betaine, butylene glycol, caprylyl glycol, dimethicone, fructose, glucomannan, glucose, glycerin, glyceryl glucoside, honey, hyaluronic acid, lactic acid, panthenol, polyethylene glycol, propylene glycol, propanediol, sodium hyaluronate, sodium lactate, sodium pyrrolidone carboxylic acid, sorbitol, and urea. In some embodiments, the composition comprises 0.1-50% w/v humectant, including all values and subranges therebetween. In some embodiments, the composition comprises 0.5-10% w/v humectant.

In some embodiments, the composition comprises hyaluronic acid. In some embodiments, the composition is a hyaluronic-based hydrogel for topical application. In some embodiments, the composition comprises 0.1-10% w/v hyaluronic acid. In some embodiments, the composition comprises 0.5-5.0% w/v hyaluronic acid. In some embodiments, the composition comprises 1-2% w/v hyaluronic acid. In some embodiments, the composition comprises a hydrogel. In some embodiments, the hydrogel comprises a cellulose polymer. In some embodiments the hydrogel comprises hydroxypropyl methylcellulose.

In some embodiments, the composition comprises a cellulose polymer. In some embodiments, the cellulose polymer is hydroxyethyl cellulose, methylcellulose, hydroxy methylcellulose, carboxymethyl cellulose, microcrystalline cellulose, ethyl cellulose, sodium carboxymethyl cellulose, hydroxypropyl cellulose, or cellulose acetate. In some embodiments, the composition comprises 0.1-20% w/v cellulose polymer, including all values and subranges therebetween. In some embodiments, the composition comprises 0.5-10% w/v of a cellulose polymer. In some embodiments, the composition comprises 1-5% w/v of a cellulose polymer.

In some embodiments, the composition comprises a thickening agent, a gelling agent, and/or a polymer. In some embodiments, the composition comprises an acrylate. In some embodiments, the composition comprises a carbomer.

In some embodiments, the composition comprises a salt. In some embodiments, the composition comprises a salt selected from the list consisting of: calcium chloride, Dead Sea salt, Epsom salt, Himalayan pink salt, magnesium chloride, sea salt, and sodium chloride. In some embodiments, the composition comprises 10-500 mM of a salt, including all values and subranges therebetween. In some embodiments, the composition comprises 50-250 mM of a salt.

In some embodiments, the composition comprises a buffer. In some embodiments, the buffer is 4-(2-hydroxyethyl)-1-piperazineethanesulfonic acid, acetic acid, ammonium acetate, boric acid, citric acid, glycine, phosphoric acid, potassium hydroxide, potassium phosphate, sodium acetate, sodium bicarbonate, sodium borate, sodium carbonate, sodium citrate, sodium dihydrogen phosphate, sodium hydrogen phosphate, sodium hydroxide, sodium phosphate, sodium tetraborate, tris(hydroxymethyl)aminomethane, or trisodium phosphate. In some embodiments, the composition comprises 1-250 mM of a buffer, including all values and subranges therebetween. In some embodiments, the composition comprises 5-50 mM of a buffer.

In some embodiments, the composition comprises a surfactant. In some embodiments, the composition comprises a surfactant selected from the list consisting of: ceteareth-20, cocamidopropyl betaine, coco-glucoside, decyl glucoside, decyl polyglucose, disodium laureth sulfosuccinate, glycereth-26, lauryl glucoside, lauryl polyglucose, sodium cocoyl glutamate, sodium cocoyl isethionate, sodium laureth sulfate, and sodium lauryl sulfate. In some embodiments, the composition comprises 0.1-20% w/v of a surfactant, including all values and subranges therebetween. In some embodiments, the composition comprises 1-10% w/v of a surfactant.

In some embodiments, the composition comprises an oil. In some embodiments, the composition comprises an oil selected from the list consisting of: argan oil, avocado oil, baobab oil, camellia oil, carrot seed oil, coconut oil, evening primrose oil, grapeseed oil, hemp seed oil, jojoba oil, macadamia nut oil, marula oil, mineral oil, olive oil, pomegranate seed oil, raspberry seed oil, rosehip seed oil, squalane oil, sunflower seed oil, sweet almond oil, and tamanu oil. In some embodiments, the composition comprises 0.1-20% w/v of an oil, including all values and subranges therebetween.

In some embodiments, the composition comprises an alcohol. In some embodiments, the composition comprises an alcohol selected from the list consisting of: cetyl alcohol, ethyl alcohol, isopropyl alcohol, and stearyl alcohol. In some embodiments, the composition comprises 0.1-20% w/v of an alcohol, including all values and subranges therebetween. In some embodiments, the composition comprises 1-10% w/v of an alcohol.

In some embodiments, the composition comprises a free amino acid. In some embodiments, the composition comprises alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, or valine. In some embodiments, the composition comprises an amino acid selected from the list consisting of: alanine, arginine, cysteine, glutamine, glycine, histidine, lysine, methionine, proline, serine, and threonine. In some embodiments, the composition comprises 10-250 mM of an amino acid, including all values and subranges therebetween. In some embodiments, the composition comprises 25-150 mM of an amino acid.

In some embodiments, the composition comprises glycerol. In some embodiments, the composition comprises 0.5-50% w/v glycerol, including all values and subranges therebetween. In some embodiments, the composition comprises 1-30% w/v glycerol. In some embodiments, the composition comprises 1-5% w/v glycerol.

In some embodiments, the composition comprises petrolatum. In some embodiments, the composition comprises 0.1-20% w/v petrolatum, including all values and subranges therebetween.

The compositions of the present disclosure can comprise an additional agent or agents, whether active or passive. Examples of such an agent include a sweetening agent, a flavoring agent, a coloring agent, a filling agent, a binding agent, a lubricating agent, an excipient, a preservative, an emollient, a hydrating agent, a smoothing agent, or a manufacturing agent. Additional excipients or additives can be added to the composition. For example, if desired, any generally accepted soluble or insoluble inert filler (diluent) material can be included in the final product (e.g., a solid dosage form). Such inert filler can comprise a monosaccharide, a disaccharide, a polyhydric alcohol, inorganic phosphates, sulfates or carbonates, and combinations thereof. Examples of suitable inert fillers include sucrose, dextrose, lactose, xylitol, fructose, sorbitol, calcium phosphate, calcium sulfate, calcium carbonate, microcrystalline cellulose, and combinations thereof. An effective amount of any generally accepted lubricant, such as calcium or magnesium soaps, can be added.

Depending on the dosage form, optional additives and modifiers further comprise one or more of acids, bases, acidity regulators, alcohol, anticaking agents, antifoaming agents, antioxidants, bulking agents, coagulation agents, colour retention agents, emulsifiers, flavor enhancers, flour treatment agents, gelling agents, glazing agents, humectants, leavening agents, tracer gases, preservatives, stabilizers, sweeteners, tenderizers, and thickeners.

The compositions of the present disclosure may additionally contain other conventional adjunct components. Thus, for example, the compositions may contain additional, compatible, active materials such as, for example, antipruritics, astringents, local anesthetics or anti-inflammatory agents, or may contain additional materials useful in physically formulating various dosage forms of the compositions of the present disclosure, such as dyes, flavoring agents, preservatives, antioxidants, opacifiers, thickening agents and stabilizers. However, such materials, when added, should not unduly interfere with the biological activities of the components of the compositions of the present disclosure. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

In some embodiments, the composition comprises a skin protectant. In some embodiments, the composition comprises an ingredient that is FDA-approved for the treatment of atopic dermatitis. In some embodiments, the composition comprises an FDA-approved skin protectant. In some embodiments, the composition comprises colloidal oatmeal. In some embodiments, the composition comprises a skin protectant selected from the list consisting of: allantoin, aluminum hydroxide gel, calamine, cocoa butter, cod liver oil, colloidal oatmeal, dimethicone, glycerin, hard fat, kaolin, lanolin, mineral oil, petrolatum, sodium bicarbonate, topical starch, white petrolatum, zinc acetate, zinc carbonate, and zinc oxide. In some embodiments, the composition comprises any one of the following skin protectants in the following ranges: allantoin, 0.5 to 2%; aluminum hydroxide gel, 0.15 to 5%; calamine, 1 to 25%; cocoa butter, 50 to 100%; cod liver oil, 5 to 13.56%; colloidal oatmeal, 0.007% minimum, or 0.003% minimum in combination with mineral oil; dimethicone, 1 to 30%; glycerin, 20 to 45%; hard fat, 50 to 100%; kaolin, 4 to 20%; lanolin, 12.5 to 50%; mineral oil, 50 to 100%, or 30 to 35% in combination with colloidal oatmeal; petrolatum, 30 to 100%; sodium bicarbonate; topical starch, 10 to 98%; white petrolatum, 30 to 100%; zinc acetate, 0.1 to 2%; zinc carbonate, 0.2 to 2%; zinc oxide, 1 to 25%. See, e.g., Sec. 347.10 of CFR Title 21, Volume 5, "Skin protectant active ingredients," incorporated by reference herein in its entirety.

In some embodiments, other ingredients are also present in the composition, such as antibiotics; antiseptics; antifungals; corticosteroids; soothing agents; anti-aging agents; smoothing agents; moisturizing agents; and protective agents.

Characteristics of Compositions of the Disclosure

The present disclosure provides chimeric proteins, as well as compositions comprising these chimeric proteins. These compositions have beneficial characteristics for therapeutic use against target *Staphylococcus* sp.

In addition to issues with selectivity, prior CWHs and endolysins known in the art have properties that are not well-suited for therapeutic indications, e.g., topical application. For example, many previously characterized CWHs suffer from weak activity, low thermostability, and/or narrow or unsuitable pH range.

The present disclosure provides chimeric proteins with beneficial characteristics, such as, but not limited to, high anti-*Staphylococcus* activity, *Staphylococcus* species specificity, thermostability, and broader or more suitable pH range. For example, an illustrative LysSA12 EAD+PlySs2 CBD chimera of the disclosure exhibits very high activity, selectivity, and thermostability, which attributes are well-suited for applications when there is a need to selectively remove *S. aureus* from a community of microorganisms that also includes other *Staphylococcus* sp. (e.g *S. epidermidis*). The skin microbiome is one example of such a community, where *S. epidermidis* is a commensal organism and key component of a healthy microbiome, while *S. aureus* is typically pathogenic and associated with skin conditions such as atopic dermatitis.

Anti-*Staphylococcus* Activity

The compositions of the present disclosure are active against *Staphylococcus* species, e.g., a target *Staphylococcus* species.

In some embodiments, a composition of the disclosure has activity against a target *Staphylococcus* species and the degree of that activity is determined based on its Minimum Inhibitory Concentration (MIC) against that target species. In some embodiments, the MIC is less than 100, 90, 80, 70, 60, 50, 40, 30, 20, or 10 µg/mL. In some embodiments, the MIC is less than 20, 19, 18, 17, 16, 15, 14, 13, 12, 11, 10, 9, 8, 7, 6, 5, 4, 3, 2, or 1 µg/mL. In some embodiments, the MIC is less than 5.0, 4.5, 4.0, 3.5, 3.0, 2.5, 2.0, 1.5, 1.0, or 0.5 µg/mL. In some embodiments, the MIC is less than 1.0, 0.9, 0.8, 0.7, 0.6, 0.5, 0.4, 0.3, 0.2, or 0.1 µg/mL.

The genus *Staphylococcus* is composed of Gram-positive and facultative anaerobic bacteria present in cutaneous and mucous membrane microbiota of mammals and birds. *Staphylococcus* is a genus comprised of nonspore-forming cocci belonging to the family Micrococcaceae. *Staphylococcus* sp. are often found as normal human microbiota of the skin and nasal cavity. The genus includes clinically relevant opportunistic pathogens in both human and veterinary medicine. The species belonging to this genus can be grouped and differentiated according to the production of the enzyme coagulase, which is an enzyme capable of converting fibrinogen into fibrin, a characteristic that is easily detectable in the laboratory and allows for a practical classification.

In general, coagulase-positive staphylococci (CoPS), such as *S. aureus, S. intermedius* and *S. pseudointermedius*, among others, are usually pathogenic, even though in some cases they can cause asymptomatic colonization in healthy individuals. In some embodiments, a composition of the disclosure is active against a coagulase-positive staphylococci (CoPS) species. In some embodiments, the species is *S. aureus*. In some embodiments, the compositions of the present disclosure are active against the species *S. intermedius*. In some embodiments, the compositions of the present disclosure are active against the species *S. pseudointermedius*.

Coagulase-negative staphylococci (CoNS), represented by a larger group of species, have been associated with opportunistic infections. CoNS species, such as *S. epidermidis, S. haemolyticus* and *S. lugdunensis* have been associated with opportunistic infections in humans. *S. epidermidis* and some subspecies of *S. schleiferi* can cause skin and ear infections in dogs. *S. felis* can cause lower urinary tract disease, eye infections, and otitis in cats. In some embodiments, a composition of the disclosure is active against a coagulase-negative staphylococci (CoNS) species.

In some embodiments, a composition of the disclosure is selective for one or more CoPS species in comparison to one or more CoNS species.

In some embodiments, the compositions of the present disclosure are active against *S. aureus*. *S. aureus* is considered the most important pathogen of the genus. In people, it can be found in community settings and hospital premises, constituting an important source of infections associated with healthcare. The bacterium can produce infections in humans associated with skin and soft tissue, pneumonia, septicemia and osteomyelitis. These conditions have also been reported in animals. S. aureus is able to cause many superficial pyogenic (pus-forming) infections of the dermis and underlying tissues as well as serious systemic infections. It can produce a range of toxins including enterotoxins (food poisoning), cytotoxins (general systemic toxins), and toxic shock superantigens.

In some embodiments, the compositions of the present disclosure are active against S. pseudointermedius. S. pseudointermedius is a common cause of skin and soft tissue infections in humans, as well as in dogs and cats.

In some embodiments, the compositions of the present disclosure are active against S. epidermidis. S. epidermidis is a common cause of infections associated with medical devices such as catheters, pacemakers, and prosthetic joints. It is also a leading cause of bloodstream infections in hospitalized patients.

In some embodiments, the compositions of the present disclosure are active against S. saprophyticus. S. saprophyticus is a common cause of urinary tract infections in young, sexually active women.

In some embodiments, the compositions of the present disclosure are active against S. haemolyticus. S. haemolyticus is a leading cause of infections associated with central venous catheters and other medical devices, particularly in immunocompromised patients.

In some embodiments, the compositions of the present disclosure are active against S. lugdunensis. S. lugdunensis is increasingly recognized as a significant pathogen, particularly in skin and soft tissue infections, endocarditis, and bone and joint infections.

In some embodiments, a composition of the disclosure is active against a species of Staphylococcus. In some embodiments, a composition of the disclosure is active against a Staphylococcus species selected from: S. agnetis, S. argensis, S. argenteus, S. arlettae, S. aureus, S. auricularis, S. capitis, S. caprae, S. carnosus, S. chromogenes, S. cohnii, S. condimenti, S. cornubiensis, S. delphini, S. devriesei, S. edaphicus, S. epidermidis, S. equi, S. equorum, S. felis, S. fleurettii, S. gallinarum, S. haemolyticus, S. hominis, S. hyicus, S. intermedius, S. kloosii, S. lentus, S. lugdunensis, S. lutrae, S. massiliensis, S. microti, S. muscae, S. nepalensis, S. pasteuri, S. petrasii, S. pettenkoferi, S. piscifermentans, S. pseudintermedius, S. pseudoxylosus, S. rostri, S. saccharolyticus, S. saprophyticus, S. schleiferi, S. schweitzeri, S. sciuri, S. simiae, S. simulans, S. stepanovicii, S. succinus, S. vitulinus, S. warneri, and S. xylosus.

In some embodiments, a composition of the disclosure is active against a Staphylococcus species in the same phylogenetic grouping as S. aureus. In some embodiments, a composition of the disclosure is active against S. argenteus, S. aureus, S. schweitzeri, or S. simiae. See, e.g., Madhaiyan et al., Int. J Syst. Evol. Microbiol 2020; 70:5926-5936, incorporated by reference herein, which provides a phylogenetic analysis of Staphylococcus species.

In some embodiments, a composition of the disclosure is active against a Staphylococcus species in the same phylogenetic grouping as S. epidermidis. In some embodiments, a composition of the disclosure is active against S. capitis, S. caprae, S. epidermidis, or S. saccharolyticus.

Selectivity

The present inventors discovered that illustrative novel chimeras disclosed herein, e.g., LysSA12 EAD+PlySs2 CBD, LysSA12 EAD+LysA72 CBD, and LysSA12 EAD+ALE-1 CBD, exhibited remarkable selective activity for S. aureus over S. epidermidis. Surprisingly, it was discovered that the CBDs and EADs comprised by these chimeras did not exhibit the same selectivity in other chimeric combinations. As known in the art, the vast majority of CWHs having lytic activity towards S. aureus also have similar lytic activity towards S. epidermidis, meaning that while they can kill unwanted S. aureus overgrowth, they would also kill beneficial S. epidermidis populations, which is highly undesirable for a topical skin microbiome application. By contrast, illustrative chimeric CWHs of the present disclosure are able to distinguish between Staphylococcus aureus and Staphylococcus epidermis by comprising specific combinations of CBDs and EADs.

In some embodiments, a chimeric protein herein has Staphylococcus species-specific activity. In some embodiments, a chimeric protein herein has selectivity for one species of Staphylococcus over another species of Staphylococcus. Selectivity in this context refers to a chimeric protein of the disclosure that has higher activity against one species of Staphylococcus than another species of Staphylococcus. In some embodiments, a chimeric protein herein is selective for one group of Staphylococcus species over another group of Staphylococcus species. For example, in some embodiments, a chimeric protein of the disclosure is selective for the phylogenetic grouping that includes Staphylococcus aureus over the phylogenetic grouping that includes Staphylococcus epidermidis. In some embodiments, a chimeric protein of the disclosure is selective for a coagulase-positive staphylococci (CoPS) species (e.g., Staphylococcus aureus) over a coagulase-negative staphylococci (CoNS) species (e.g., Staphylococcus epidermidis).

In some embodiments, a chimeric protein herein is selective for S. aureus over another species of Staphylococcus. In some embodiments, a chimeric protein herein is selective for S. aureus over a CoNS species. In some embodiments, a chimeric protein of the disclosure is selective for S. aureus over S. epidermidis. In some embodiments, a chimeric protein of the disclosure is selective for S. aureus over S. hominis.

The degree of selectivity exhibited by a given chimeric protein against one species in comparison to another species, e.g. species A and species B, is generally defined based on a comparison of that chimeric protein's activity against species A versus its activity against species B. When activity is defined by minimum inhibitory concentration (MIC), e.g., via an MIC assay, the selectivity toward species A over species B is calculated by the inverse ratio of the MIC of the chimeric protein against each species, i.e.:

$$\text{Fold selectivity} = \frac{MIC_{species\,B}}{MIC_{species\,A}}.$$

In some embodiments, a chimeric protein of the disclosure has at least 2, 3, 4, 5, 6, 7, 8, 9, or 10-fold selectivity. In some embodiments, a chimeric protein of the disclosure has at least 5, 10, 15, 20, 25, 30, 35, 40, 45, 50, 55, 60, 65, 70, 75, 80, 85, 90, 95, or 100-fold selectivity. In some embodiments, a chimeric protein of the disclosure has virtually no activity (or no detectable activity) against one species, while having measurable activity against another species.

In some embodiments, a composition of the disclosure has broad range anti-*Staphylococcus* activity. In some embodiments, the composition has high activity against multiple species of *Staphylococcus*. In some embodiments, the composition has high activity against a group of related *Staphylococcus* species. In some embodiments, the composition has high activity against a diverse group of *Staphylococcus* species. In some embodiments, the composition is suitable for use as a broad-range therapeutic.

Thermostability

The inventors of the present disclosure also surprisingly discovered that some of the novel chimeric CWHs of the disclosure, e.g., SEQ ID NO: 21, exhibited higher thermostability in chimeric CWHs of the disclosure than a control CWH comprising the Twort EAD (SEQ ID NO: 27).

In some embodiments, a composition of the disclosure exhibits thermostability at temperatures up to 37, 38, 39, 40, 41, 42, 43, 44, 45, 46, 47, 48, 49, 50, 51, 52, 53, 54, 55, 56, 57, 58, 59, or 60° C., including all values and ranges therebetween. In some embodiments, a composition of the disclosure exhibits thermostability at temperatures of at least 37, 38, 39, 40, 41, 42, 43, 44, 45, 46, 47, 48, 49, 50, 51, 52, 53, 54, 55, 56, 57, 58, 59, or 60° C., including all values and ranges therebetween.

As used herein, thermostability at a given temperature refers to the ability to maintain activity levels at that temperature, or after the protein is exposed to that temperature. In some embodiments, thermostability at a given temperature is measured after exposure to that temperature for a period of time. In some embodiments, thermostability is determined based on experiments testing activity at a temperature or after exposure to a given temperature for a period of time (e.g., showing measurable target bacterial density reductions at that temperature or after exposure to that temperature). Thus, in some embodiments, an EAD, CBD, or chimeric protein is considered thermostable at a temperature if it still exhibits measurable activity at that temperature or after exposure to that temperature. In some embodiments, an EAD, CBD, or recombinant chimeric protein is considered thermostable at a critical temperature, if it still exhibits measurable activity at its intended use temperature after being exposed to that critical temperature (e.g., activity tested after the protein is exposed to the critical temperature for 30 mins). In some embodiments, thermostability after exposure to a given temperature is determined based on assays conducted at room temperature. In some embodiments, thermostability is determined after exposure to a given temperature based on an assay that measures activity. In some embodiments, the assay is a turbidity reduction assay.

In the context of comparing two proteins (e.g., two EADs, two CBDs, or two chimeric CWHs), one protein may be considered more thermostable at a given temperature than the other if it exhibits higher absolute activity at that temperature or after exposure to that temperature (e.g., if it results in greater microbial density reductions in the measured time). In other embodiments, one protein may be considered more thermostable than the other at a given temperature if it exhibits higher relative activity at that temperature or after exposure to that temperature (e.g., if the protein exhibits a lesser reduction in activity after exposure to a given temperature compared to the relative reduction of activity of a second protein after exposure to that same temperature).

In some embodiments, thermostability at a given temperature is determined based on ability to maintain activity after exposure to that temperature for 10, 20, 30, 40, 50, or 60 minutes, including all values and ranges therebetween. In some embodiments, thermostability at a given temperature is determined after exposure to that temperature for 1, 2, 3, 4, 5, 6, 7, 8, 9, 10, 11, 12, 13, 14, 15, 16, 17, 18, 19, 20, 21, 22, 23, or 24 hours, including all values and ranges therebetween. In some embodiments, thermostability at a given temperature is determined after exposure to that temperature for 1, 2, 3, 4, 5, 6, or 7 days, including all values and ranges therebetween. In some embodiments, thermostability at a given temperature is determined after exposure to that temperature for 1, 2, 3, or 4 weeks, including all values and ranges therebetween. In some embodiments, thermostability at a given temperature is determined after exposure to that temperature for 1, 2, 3, 4, 5, or 6 months, including all values and ranges therebetween.

In some embodiments, thermostability is measured based on testing activity after maintaining a composition at a given temperature for a period of time, e.g., weeks or months. In some embodiments, thermostability is determined based on activity retained after 2 months at a given temperature.

In some embodiments, a composition herein is thermostable at 45° C. for at least four weeks. In some embodiments, a composition herein is thermostable at 45° C. for at least two months. In some embodiments, a composition herein is thermostable at 50° C. for at least two months.

In some embodiments, a composition herein is considered thermostable or shelf stable if it retains at least 10, 20, 30, 40, 50, 60, 70, 80, or 90% of its original activity, including all values and ranges therebetween, at room temperature after exposure to a temperature of 45° C. for four weeks.

pH Range

In some embodiments, a composition herein is stable at a range of pH values. A composition, e.g., a chimeric protein, is considered stable at a given pH level if it exhibits activity at that pH level. In some embodiments, pH stability at different pH values is determined based on activity assays conducted at different pH values. E.g., in some embodiments, pH stability is determined by incubating a composition of the disclosure (e.g., a chimeric protein) with target bacterial cells at different pH values (e.g., in a turbidity reduction assay). The results of the assay provide activity levels for the composition at different pH values, including a maximum activity level. In some embodiments, a composition is stable at a pH level if it has the same activity at that pH as its maximum activity level. In some embodiments, a composition is stable at a pH level if it exhibits at least 50, 60, 70, 80, 90, 95, 96, 97, 98, or 99% of its maximum activity at that pH. In some embodiments, a composition is stable at a pH level if it exhibits about 50, 60, 70, 80, 90, 95, 96, 97, 98, or 99% of its maximum activity at that pH.

In some embodiments, pH stability is determined based on an activity assay. In some embodiments, the assay is a turbidity reduction assay.

In some embodiments, a composition herein is stable at a pH of 3, 4, 5, 6, 7, 8, 9, or 10, or within any ranges therebetween. In some embodiments, a composition herein is stable in the pH range of 6-8. In some embodiments, a composition herein is stable in the pH range of 5-8. In some embodiments, a composition herein is stable at pH values most relevant for topical skin applications. E.g., in some embodiments, a composition herein is stable at a pH of 4, 5, or 6.

Synergy

In some embodiments, the present disclosure provides a combination composition comprising at least two compositions, e.g., chimeric proteins, of the disclosure. In some embodiments, at least two compositions of the disclosure are administered together. In some embodiments, two compositions of the disclosure are administered one after the other or simultaneously. In some embodiments, a combination composition of the disclosure exhibits synergistic results compared to the constituent compositions individually.

In some embodiments, a chimeric protein of the disclosure exhibits a synergistic effect from the combination of a CBD and an EAD comprised therein. In some embodiments, this synergy is measured in comparison to a control protein. In some embodiments, the control protein is the original protein from which the CBD is derived. In some embodiments, the control protein is the original protein from which the EAD is derived. In some embodiments, the control protein is a control chimera comprising the CBD and comprising a control EAD. In some embodiments, the control protein is a control chimera comprising the EAD and comprising a control CBD. In some embodiments, the control CBD is the Twort CBD. In some embodiments, the control EAD is the Twort EAD. The discussion of synergy provided herein applies to combination compositions of the disclosure and to chimeras comprising domains that interact synergistically.

As used herein, the term "synergistic" as it refers to a composition of the disclosure, refers to a composition that exhibits an effect (y) that is in excess of the predicted effect of the composition as calculated by a reference model. In some embodiments, "synergistic" refers to an effect that is greater than a simple additive effect. In some embodiments, a synergistic combination is one for which the MIC of the combination is lower than the MIC for its constituent components. In some embodiments, a synergistic combination is one for which the MIC of the combination is lower than the MIC for its constituent components, as calculated by percent composition. For example, in some embodiments, a synergistic combination of a CBD and an EAD is one in which the MIC of the CBD-EAD chimera is lower than the MIC for a control protein.

In some embodiments, the presence of synergy for a combination composition is determined based on the Fractional Inhibitory Concentration (FIC) index value. To quantify the potency of a combination of agents in comparison to the individual activities of each agent, the Fractional Inhibitory Concentration (FIC) index value for each combination of proteins is calculated using the following equation:

$$\frac{A}{MIC_A} + \frac{B}{MIC_B} = FIC_A + FIC_B = FIC \text{ Index},$$

where A and B are the concentration of each protein in a given well and $MIC_A$ and $MIC_B$ are the MIC's of each protein individually; $FIC_A$ and $FIC_B$ are the fractional inhibitory concentrations for protein A and B, respectively, and their sum gives the overall FIC index for that well. The criteria for a determination of synergistic activity are: i) no detectable growth of a target bacterium when exposed to the combination (e.g., the combination is at a concentration equal to or greater than its MIC), and ii) an FIC index less than or equal to 0.5.

In some embodiments, a synergistic effect is calculated using the Synergyfinder web application. The following reference describes the Synergyfinder web application in detail and is incorporated by reference herein in its entirety: Ianevski, A.; He, L.; Aittokallio, T.; Tang, J. SynergyFinder: A Web Application for Analyzing Drug Combination Dose-Response Matrix Data Bioinformatics 2017, 33 (15), 2413-2415.

In some embodiments, the reference model is a "simple deduction model." The simple deduction model determines that a composition exhibits a synergistic effect if the observed effect is greater than the effect predicted from the sum of the effects of the individual components. The synergistic effect according to the deduction model may be calculated using the following equation: y=Observed effect of composition−(sum of expected effect of individual active ingredient components). If y is greater than zero, the composition exhibits a synergistic effect. The synergy percentage adjusted model may also be calculated. The equation for the synergy percentage adjusted is: observed effect of the composition—additive inhibition value. The additive inhibition value for a composition containing two components (e.g., A and B) may be calculated according to the following equation: (Expected effect of component A)+((1−expected effect of component A)×expected effect of component B)/100.

In some embodiments, the reference model is "Highest Single Agent" (HSA). The HSA model states that the expected combination effect equals to the higher effect of individual drugs: $y_{HSA}=\max(y_1,y_2)$. The following reference describes this model in detail and is incorporated by reference herein in its entirety: Berenbaum, M. C. (1989). What is synergy? Pharmacol. Rev., 41(2):93-141.

In some embodiments, the reference model is the Loewe additivity model. This model defines the expected effect $y_{LOEWE}$ as if a drug was combined with itself the Loewe additivity model considers the dose-response curves of individual drugs. The expected effect $y_{LOEWE}$ must satisfy:

$$\frac{x_1}{x_{LOEWE}^1} + \frac{x_2}{x_{LOEWE}^2} = 1,$$

where $x_1$ and $x_2$ and $x_{LOEWE}^1$ and $x_{LOEWE}^2$ are the doses of component 1 1 and component 2 alone that produce $y_{LOEWE}$. Using 4-parameter log-logistic (4PL) curves to describe dose-response curves the following parametric form of previous equation is derived:

$$\frac{x_1}{m_1\left(\frac{y_{LOEWE}-E_{min}^1}{E_{max}^1-y_{LOEWE}}\right)^{\frac{1}{\lambda^1}}} + \frac{x_2}{m_2\left(\frac{y_{LOEWE}-E_{min}^2}{E_{max}^2-y_{LOEWE}}\right)^{\frac{1}{\lambda^2}}},$$

where $E_{min}, E_{max} \in [0,1]$ are minimal and maximal effects of each component, $m_{1,2}$ are the doses of components that produce the midpoint effect of $E_{min}+E_{max}$, also known as relative $EC_{50}$ or $IC_{50}$, and $\lambda_{1,2}$ ($\lambda$>0) are the shape parameters for indicating the sigmoidicity or slope of dose-response cur es. A numerical nonlinear solver can be then used to determine $y_{LOEWE}$ for $x_1$ and $x_2$. The Loewe additivity model is described in detail in the following reference, which is incorporated by reference herein in its entirety: Loewe, S. (1953). The problem of synergism and antagonism of combined drugs. Arzneinit-telforschung, 3(6):285-290.

In some embodiments, the reference model is the Bliss model. The Bliss model is described in detail in the following reference, which is incorporated by reference herein in its entirety: Bliss, C. I. (1939). The toxicity of poisons applied jointly1. Annals of Applied Biology, 26(3):585-615.

Bliss assumes a stochastic process in which two components exert their effects independently, and the expected combination effect can be calculated based on the probability of independent events as: $y_{BLISS}=y_1+y_2-y_1 \times y_2$.

In some embodiments, the reference model is the Zero Interaction Potency (ZIP) model. The ZIP model is described in detail in the following reference, which is incorporated by reference herein in its entirety: Yadav, B., Wennerberg, K., Aittokallio, T., and Tang, J. (2015). Searching for Drug Synergy in Complex Dose-Response Landscapes Using an Interaction Potency Model. Comput Struct Biotechnol J, 13:504-513. ZIP calculates the expected effect of two components under the assumption that they do not potentiate each other:

$$y_{ZIP} = \frac{\left(\frac{x_1}{m_1}\right)^{\lambda_1}}{\left(1+\frac{x_1}{m_1}\right)^{\lambda_1}} + \frac{\left(\frac{x_2}{m_2}\right)^{\lambda_2}}{\left(1+\frac{x_2}{m_2}\right)^{\lambda_2}} - \frac{\left(\frac{x_1}{m_1}\right)^{\lambda_1}}{\left(1+\frac{x_1}{m_1}\right)^{\lambda_1}} \cdot \frac{\left(\frac{x_2}{m_2}\right)^{\lambda_2}}{\left(1+\frac{x_2}{m_2}\right)^{\lambda_2}}$$

Methods of Treating *Staphylococcus* Conditions

The present disclosure provides methods of treating conditions associated with *Staphylococcus* comprising administering a composition of the disclosure.

A composition as disclosed herein may be used to treat subjects affected by a condition associated with a *Staphylococcus* species as defined herein. In some embodiments, the subject is an animal. In some embodiments, the animal is a mammal. In some embodiments, the subject is a human.

Conditions

In some embodiments, a composition of the disclosure is used in the treatment of a condition associated with *Staphylococcus*. In some embodiments, the condition is a *Staphylococcus* infection.

In some embodiments, the condition is associated with the skin. In some embodiments, the condition is a skin infection. In some embodiments, the condition is impetigo, cellulitis, folliculitis, atopic dermatitis, acute radiation dermatitis, acne, or an abscess. In some embodiments, the condition is atopic dermatitis. In some embodiments, the condition is acute radiation dermatitis. In some embodiments, the condition is dry, itchy, and/or red skin. In some embodiments, the condition is dry skin. In some embodiments, the condition is itchy skin. In some embodiments, the condition is red skin.

In some embodiments, the condition is a wound infection, pneumonia, food poisoning, toxic shock syndrome, a bloodstream infection, pneumonia, a urinary tract infection, a bone or joint infection (e.g., osteomyelitis, septic arthritis), endocarditis, meningitis, septicemia, an ear infection (e.g., otitis externa), an eye infection (e.g., conjunctivitis, keratitis), a sinus infection, gastroenteritis, mastitis, peritonitis, a prosthetic joint infection, a sternal wound infection, a catheter-related infection, or tonsillitis. In some embodiments, the condition is an infection of the skin. In some embodiments, the condition is an infection of the soft tissue. In some embodiments, the condition is an opportunistic infection. In some embodiments, the condition is a wound infection. In some embodiments, the condition is a chronic wound.

In some embodiments, the condition is the presence of *Staphylococcus* species within an environment, e.g., on surfaces within a hospital. In some embodiments, a composition herein is used as a disinfectant to reduce the concentration or presence of *Staphylococcus* species in an environment.

Dosages

In some embodiments, a composition of the disclosure comprises 0.1-100 µg/mL of a recombinant protein, e.g., a chimeric protein, disclosed herein, including all values and subranges therebetween. In some embodiments, the composition comprises 0.5-50 µg/mL of a protein of the disclosure. In some embodiments, the composition comprises 1-25 µg/mL of a protein of the disclosure. In some embodiments, the composition comprises 2-15 µg/mL of a protein of the disclosure. In some embodiments, the composition comprises about 4 µg/mL of a protein of the disclosure.

In some embodiments, a composition of the disclosure comprises about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 µg/mL of a protein of the disclosure.

Administration

For the purposes of administration, the present compositions may be formulated in a variety of forms. The term "dosage form" denotes any form of the formulation that contains an amount of a chimeric protein of the disclosure sufficient to achieve at least a partial therapeutic effect with a single or repeat administration. In some embodiments, the dosage form is a topical dosage form. In some embodiments, the dosage form is a lotion, an oil, a hydrogel, a salve, or a body balm. In some embodiments, the dosage form is a lotion. In some embodiments, the dosage form is a hydrogel.

Compositions can be formulated in forms including but not limited to liquid, gel, semi-solid, and solid. Compositions disclosed herein can further be processed into forms including but not limited to solids, liquids, suspensions, gels, lotions, balms, and other forms discussed in this disclosure.

In some embodiments, an effective amount of a composition is administered to a subject. The term "effective amount" or "therapeutically effective amount" refers to that amount of a composition described herein that is sufficient to effect the intended application including but not limited to a decrease in a *Staphylococcus* population. The therapeutically effective amount may vary depending upon the subject and condition being treated, e.g., the weight and age of the subject, the severity of the disease condition, the manner of administration and the like, which can readily be determined by one of ordinary skill in the art. The term also applies to a dose that will induce a particular response in a target location, e.g., a reduction in inflammation, pain, acne, fever, etc. The specific dose will vary depending on the particular formulation of the composition, the dosing regimen to be followed, whether it is administered in combination with other compounds, timing of administration, the tissue to which it is administered, route of administration and the physical delivery system in which it is carried.

In some embodiments, a composition as disclosed herein is said to be active, functional or therapeutically active or able to treat, prevent and/or delay a condition associated with *Staphylococcus* when it reduces or ameliorates one or more symptoms associated with that condition. In some embodiments, a composition is considered therapeutically active when it decreases a symptom by at least 5, 10, 15, 20, 25, 30, 35, 40, 45, 50, 55, 60, 65, 70, 75, 80, 85, 90, 95, 96, 97, 98, 99, or 100% after treatment compared to the severity of that symptom before treatment. In some embodiments, a composition is considered therapeutically active when it decreases a symptom by at most 5, 10, 15, 20, 25, 30, 35, 40, 45, 50, 55, 60, 65, 70, 75, 80, 85, 90, 95, 96, 97, 98, 99, or 100% after treatment compared to the severity of that symptom before treatment. In some embodiments, a composition is considered therapeutically active when it decreases a symptom by about 5, 10, 15, 20, 25, 30, 35, 40, 45, 50, 55, 60, 65, 70, 75, 80, 85, 90, 95, 96, 97, 98, 99, or 100%, including all values and subranges therebetween, after treatment compared to the severity of that symptom before treatment. In some embodiments, the symptom is pain, fever, swelling, redness, dry skin, lesion number, lesion size, rash, warmness, drainage, discharge, cough, shortness of breath, rapid heart rate, low or high blood pressure, chills, nausea, vomiting, diarrhea, stomach cramps, chest pain, or organ failure.

In some embodiments, a composition herein is therapeutically active when it decreases the amount of a target *Staphylococcus* species present in a subject or in an in vitro system In some embodiments, a composition herein is therapeutically active when about 90%, 80%, 70%, 60%, 50%, 40%, 30%, 20%, 10%, 5% or less of the initial amount of a *Staphylococcus* species, is still detectable after treatment. In some embodiments, a composition herein is therapeutically active when at most 90%, 80%, 70%, 60%, 50%, 40%, 30%, 20%, 10%, 5% of the initial amount of a *Staphylococcus* species is still detectable after treatment. In some embodiments, no *Staphylococcus* species is detectable after treatment. Herein, the expression "amount of *Staphylococcus* species" refers to living *Staphylococcus* species. In some embodiments, *Staphylococcus* species are detected using sequencing techniques, such as 16S sequencing or shotgun sequencing, to quantify the amount of different *Staphylococcus* species present in a sample, as well as evaluating species present in the overall microbiome in question. *Staphylococcus* species may also be detected using standard techniques known by the artisan such as immunohistochemical techniques using *Staphylococcus* specific antibodies, tube coagulase tests that detect staphylocoagulase or "free coagulase", detection of surface proteins such as clumping factor (slide coagulase test) and/or protein A (commercial latex tests). Living *Staphylococcus* species may be detected using standard techniques known by the artisan such as microbiological bacterial culture techniques and/or real-time quantitative reverse transcription polymerase chain reaction to assay for bacterial mRNA. In some embodiments, said decrease is assessed in a tissue or in a cell of an individual or a patient by comparison to the amount present in said individual or patient before treatment with a composition disclosed herein. In some embodiments, the comparison is made with a tissue or cell of said individual or patient which has not yet been treated with the composition as disclosed herein in case the treatment is local.

In some embodiments, application of a composition herein improves the health, appearance, quality, texture, or feel of the skin. In some embodiments, application of a composition herein reduces skin itchiness, redness, dryness, flaking, roughness, or pain. In some embodiments, application of a composition herein decreases the severity or frequency of sleeplessness caused by skin issues. In some embodiments, application of a composition herein to the skin once or twice daily for a period of 7-14 days reduces skin itchiness, redness, dryness, flaking, roughness, or pain in a subject in need thereof. In some embodiments, application of a composition herein to the skin once or twice daily for a period of 7-14 days reduces the severity or frequency of sleeplessness caused by skin issues.

A composition as disclosed herein may be administered to a subject in need thereof or to a cell, tissue or organ or said patient for at least one day, one week, one month, six months, one year or more. In some embodiments, a composition herein is applied for a period of 1-30 days. In some embodiments, a composition herein is applied for a period of 1-4 weeks. In some embodiments, a composition herein is applied for a period of about 1, 2, 3, 4, 5, 6, 7, 8, 9, 10, 11, or 12 months. In some embodiments, a composition herein is applied until a condition has improved. In some embodiments, a composition herein is applied to maintain a condition.

In some embodiments, a composition herein is applied 1-10 times per day. In some embodiments, a composition herein is applied 1-50 times per week. In some embodiments, a composition herein is applied as needed. In some embodiments, a composition herein is applied once or twice daily.

Accordingly, there is provided a composition as disclosed herein, for use by a subject in need thereof. Preferably, the composition is use as a medicament in the prevention, delay or treatment of a condition in a subject, wherein the condition is associated with infection with a *Staphylococcus*, such as a coagulase positive- or coagulase-negative *Staphylococcus*.

Further provided is the composition as disclosed herein for systemic or local administration to the subject.

Local administration may e.g. be used during surgery, locally at the site of infection or site of implant. The medical use disclosed herein may be formulated as a product as disclosed herein for use as a medicament for treatment of the stated conditions but can equally be formulated as a method of treatment of the stated conditions using a product as disclosed herein, a product as disclosed herein for use in the preparation of a medicament to treat the stated conditions and use of a product as disclosed herein for the treatment of the stated conditions. Such medical uses are all envisaged by the present disclosure. The subject in need of treatment, delay and/or prevention of the listed conditions may by any animal subject, preferably a mammal, more preferably cattle, domestic animals like a dog or a cat, or a human subject.

Further provided is the in vitro use of a composition as disclosed herein or a nucleic acid construct as disclosed herein, or an expression construct as disclosed herein, or a host cell as disclosed herein, as an antimicrobial or as a disinfectant.

Further provided is the use of a composition as disclosed herein or a nucleic acid construct as disclosed herein, or an expression construct as disclosed herein, or a host cell as disclosed herein, or a composition as disclosed herein, for detecting a *Staphylococcus*, such as *Staphylococcus aureus* and *Staphylococcus epidermidis*, in an ex vivo diagnostic application.

EXAMPLES

Example 1: Construction of Novel Chimeric Cell Wall Hydrolases

The inventors of the present disclosure combined cell wall hydrolase CBDs and EADs to form novel chimeric cell wall hydrolases.

Sources for EADs and CBDs. Chimeras were constructed using the following protein CHAP enzymatically active domains (EADs): LysSA12 EAD (SEQ ID NO: 11), Twort EAD (SEQ ID NO: 12), LysCSA13 EAD (SEQ ID NO: 13), and LysCSA5 EAD (SEQ ID NO: 14). Chimeras were constructed using the following endolysins/bacteriocins cell wall binding domains (CBDs): LysH5 CBD (SEQ ID NO: 15), LysA72 CBD (SEQ ID NO: 16), PlySs2 CBD (SEQ ID NO: 17), ALE-1 CBD (SEQ ID NO: 18), LysSA97 CBD (SEQ ID NO: 19), and LysPALS1 CBD (SEQ ID NO: 20).

Construction of chimeric cell wall hydrolases. DNA sequences of the EADs and CBDs were codon optimized and synthesized. Individual enzymatic domains including up to 50 aa upstream and downstream were synthesized with NdeI/SpeI sites. Individual cell wall binding domains including up to 25 aa upstream and downstream were synthesized with SpeI/HindIII sites. The chimeric CWHs were constructed by ligating both an EAD and a CBD into the NdeI/HindIII sites of pET24a (+). The vector also appended a C-terminal sequence encoding a 6×His protein tag used for protein purification. Chimeric enzymes consisting of combinations of one EAD and one CBD were constructed, as shown in Table 3 below.

TABLE 3

Description and sequences of illustrative chimeric proteins.

| Chimera Description | SEQ ID NO | Sequence |
|---|---|---|
| LysSA12 EAD + PlySs2 CBD | 21 | MQAKLTKKEFIEWLKTSEGKQYNADGWYGFQCFDYANAGWQ VLFGYNLKGVGAKDIPSANDFNGLATVYQNTPDFLAQPGDMVV FGSNYGAGYGHVAWVIEATLDYIIVYEQNWLGGGWTDGVQQP GSGWEKVTRRQHAYDFPMWFIRPNFKSETAPRSVQSPTQASKKE TTSSRSYRETGTMTVTVDALNVRRAPNTSGEIVAVYKRGESFDY DTVIIDVNGYVWVSYIGGSGKRNYVATGATKDGKRFGNAWGTF KLE |
| LysSA12 EAD + LysA72 CBD | 22 | MQAKLTKKEFIEWLKTSEGKQYNADGWYGFQCFDYANAGWQ VLFGYNLKGVGAKDIPSANDFNGLATVYQNTPDFLAQPGDMVV FGSNYGAGYGHVAWVIEATLDYIIVYEQNWLGGGWTDGVQQP GSGWEKVTRRQHAYDFPMWFIRPNFKSETAPRSVQSPTQASKKE TTSKNPPVPAGYTLDKNNVPYKKEAGNYTVANVKGNNVRDGY STNSRITGVLPNNATIKYDGAYCINGYRWITYIANSGQRRYIATG EVDKAGNRISSFGKFSTIKLAAALE |
| LysSA12 EAD + LysH5 CBD | 23 | MQAKLTKKEFIEWLKTSEGKQYNADGWYGFQCFDYANAGWQ VLFGYNLKGVGAKDIPSANDFNGLATVYQNTPDFLAQPGDMVV FGSNYGAGYGHVAWVIEATLDYIIVYEQNWLGGGWTDGVQQP GSGWEKVTRRQHAYDFPMWFIRPNFKSETAPRSVQSPTQASKKE TTSSNDSSASSNTVKPVASAWKRNKYGTYYMEESARFTNGNQPI TVRKVGPFLSCPVGYQFQPGGYCDYTEVMLQDGHVWVGYTWE GQRYYLPIRTWNGSAPPNQILGDLWGEISKLAAALE |
| LysSA12 EAD + ALE-1 CBD | 24 | MQAKLTKKEFIEWLKTSEGKQYNADGWYGFQCFDYANAGWQ VLFGYNLKGVGAKDIPSANDFNGLATVYQNTPDFLAQPGDMVV FGSNYGAGYGHVAWVIEATLDYIIVYEQNWLGGGWTDGVQQP GSGWEKVTRRQHAYDFPMWFIRPNFKSETAPRSVQSPTQASKKE TTSMPFLKSAGYGSNSTSSSNNNGYKTNKYGTLYKSESASFTAN TDIITRLTGPFFRSMPQSGVLRKGLTIKYDEVMKQDGHVWVGYNT NSGKRVYLPVRTWNESTGELGPLWGTIKKLAAALE |
| LysSA12 EAD + PALSI CBD | 25 | MQAKLTKKEFIEWLKTSEGKQYNADGWYGFQCFDYANAGWQ VLFGYNLKGVGAKDIPSANDFNGLATVYQNTPDFLAQPGDMVV FGSNYGAGYGHVAWVIEATLDYIIVYEQNWLGGGWTDGVQQP GSGWEKVTRRQHAYDFPMWFIRPNFKSETAPRSVQSPTQASKKE TTSSASTPATRPVTGSWKKNQYGTWYKPESATFVNGNQPIVTRI GSPFLNAPVGGNLPAGATIVYDEVCIQAGHIWIGYNAYNGNRVY CPVRTCQGVPPSHVPGVAWGTFKKLAAALE |
| LysSA12 EAD + LysA97 CBD | 26 | MQAKLTKKEFIEWLKTSEGKQYNADGWYGFQCFDYANAGWQ VLFGYNLKGVGAKDIPSANDFNGLATVYQNTPDFLAQPGDMVV FGSNYGAGYGHVAWVIEATLDYIIVYEQNWLGGGWTDGVQQP GSGWEKVTRRQHAYDFPMWFIRPNFKSETAPRSVQSPTQASKKE TTSPSSKPSADKITWNWKGVFYPNPEKAIRVRKTAGLTGTVVEE DSWLYTKDDWVKFDQVIKKDGYWWIRFKYQREGSSTNNFYCA VCRITDKEQKIKNEKYWGTIEWAKLAAALE |
| Twort EAD + LysA72 CBD | 27 | MKTLKQAESYIKSKVNTGTDFDGLYGYQCMDLAVDYIYHVTDG KIRMWGNAKDAINNSFGGTATVYKNYPAFRPKYGDVVVWTTG NFATYGHIAIVTNPDPYGDLQYVTVLEQNWNGNGIYKTELATIR THDYTGITHFIRPNFATESSVKKKDTKKKPKPSNRDGTSKNPPVP AGYTLDKNNVPYKKEAGNYTVANVKGNNVRDGYSTNSRITGV LPNNATIKYDGAYCINGYRWITYIANSGQRRYIATGEVDKAGNRI SSFGKFSTIKLAAALE |
| Twort EAD + PlySs2 CBD | 28 | MKTLKQAESYIKSKVNTGTDFDGLYGYQCMDLAVDYIYHVTDG KIRMWGNAKDAINNSFGGTATVYKNYPAFRPKYGDVVVWTTG NFATYGHIAIVTNPDPYGDLQYVTVLEQNWNGNGIYKTELATIR THDYTGITHFIRPNFATESSVKKKDTKKKPKPSNRDGTSSRSYRE TGTMTVTVDALNVRRAPNTSGEIVAVYKRGESFDYDTVIIDVNG YVWVSYIGGSGKRNYVATGATKDGKRFGNAWGTFKLE |

TABLE 3-continued

Description and sequences of illustrative chimeric proteins.

| Chimera Description | SEQ ID NO | Sequence |
|---|---|---|
| Twort EAD + ALE-1 CBD | 29 | MKTLKQAESYIKSKVNTGTDFDGLYGYQCMDLAVDYIYHVTDG KIRMWGNAKDAINNSFGGTATVYKNYPAFRPKYGDVVVWTTG NFATYGHIAIVTNPDPYGDLQYVTVLEQNWNGNGIYKTELATIR THDYTGITHFIRPNFATESSVKKKDTKKKPKPSNRDGTSMPFLKS AGYGSNSTSSSNNNGYKTNKYGTLYKSESASFTANTDIITRLTGP FRSMPQSGVLRKGLTIKYDEVMKQDGHVWVGYNTNSGKRVYL PVRTWNESTGELGPLWGTIKKLAAALE |
| LysCSA13 EAD + LysA72 CBD | 30 | MKSQKQAKQWIDVNTGKGVDFDGAYGFQCMDLAVAYVYYITD GKVRMWGNAKDAINNDFKGLATVYENTPRFKPQLGDVAVYTN SQYGHIQVVISGNLDYYTCLEQNWLNGGYDGWEKATIRTHYYD GVTHFIRPKFSDSNSQVTSKNPPVPAGYTLDKNNVPYKKEAGNY TVANVKGNNVRDGYSTNSRITGVLPNNATIKYDGAYCINGYRWI TYIANSGQRRYIATGEVDKAGNRISSFGKFSTIKLAAALE |
| LysCSA13 EAD + PlySs2 CBD | 31 | MKSQKQAKQWIDVNTGKGVDFDGAYGFQCMDLAVAYVYYITD GKVRMWGNAKDAINNDFKGLATVYENTPRFKPQLGDVAVYTN SQYGHIQVVISGNLDYYTCLEQNWLNGGYDGWEKATIRTHYYD GVTHFIRPKFSDSNSQVTSSRSYRETGTMTVTVDALNVRRAPNTS GEIVAVYKRGESFDYDTVIIDVNGYVWVSYIGGSGKRNYVATGA TKDGKRFGNAWGTFKLE |
| LysCSA13 EAD + ALE-1 CBD | 32 | MKSQKQAKQWIDVNTGKGVDFDGAYGFQCMDLAVAYVYYITD GKVRMWGNAKDAINNDFKGLATVYENTPRFKPQLGDVAVYTN SQYGHIQVVISGNLDYYTCLEQNWLNGGYDGWEKATIRTHYYD GVTHFIRPKFSDSNSQVTSMPFLKSAGYGSNSTSSSNNNGYKTNK YGTLYKSESASFTANTDIITRLTGPFRSMPQSGVLRKGLTIKYDEV MKQDGHVWVGYNTNSGKRVYLPVRTWNESTGELGPLWGTIKK LAAALE |
| LysCSA5 EAD + LysA72 CBD | 33 | MAKTQAEINKRLDAYAKGTVDSPYRIKKATSYDPSFGVMEAGAI DADGYYHAQCQDLITDYVLWLTDNKVRTWGNAKDQIKQSYGT GFKIHENKPSTVPKKGWIAVFTSGSYQQWGHIGIVYDGGNTSTFT ILEQNWNGYANKKPTKRVDNYYGLTHFIEIPVKAGTTVKKETAK KSATSKNPPVPAGYTLDKNNVPYKKEAGNYTVANVKGNNVRD GYSTNSRITGVLPNNATIKYDGAYCINGYRWITYIANSGQRRYIA TGEVDKAGNRISSFGKFSTIKLAAALE |
| LysCSA5 EAD + PlySs2 CBD | 34 | MAKTQAEINKRLDAYAKGTVDSPYRIKKATSYDPSFGVMEAGAI DADGYYHAQCQDLITDYVLWLTDNKVRTWGNAKDQIKQSYGT GFKIHENKPSTVPKKGWIAVFTSGSYQQWGHIGIVYDGGNTSTFT ILEQNWNGYANKKPTKRVDNYYGLTHFIEIPVKAGTTVKKETAK KSATSSRSYRETGTMTVTVDALNVRRAPNTSGEIVAVYKRGESF DYDTVIIDVNGYVWVSYIGGSGKRNYVATGATKDGKRFGNAW GTFKLE |
| LysCSA5 EAD + ALE-1 CBD | 35 | MAKTQAEINKRLDAYAKGTVDSPYRIKKATSYDPSFGVMEAGAI DADGYYHAQCQDLITDYVLWLTDNKVRTWGNAKDQIKQSYGT GFKIHENKPSTVPKKGWIAVFTSGSYQQWGHIGIVYDGGNTSTFT ILEQNWNGYANKKPTKRVDNYYGLTHFIEIPVKAGTTVKKETAK KSATSMPFLKSAGYGSNSTSSSNNNGYKTNKYGTLYKSESASFT ANTDIITRLTGPFRSMPQSGVLRKGLTIKYDEVMKQDGHVWVG YNTNSGKRVYLPVRTWNESTGELGPLWGTIKKLAAALE |

Bacterial strains and culture conditions. *Escherichia coli* DH10B (Invitrogen™, Carlsbad, CA) was used for cloning and storage. *E. coli* BL21 (DE3) (EMD Biosciences, San Diego, CA) was used for protein expression. All *E. coli* strains were grown at 37° C. with shaking in 2×YT medium (16 g/L tryptone, 10 g/L yeast extract, 5 g/L NaCl) or on plates containing LB (10 g/L tryptone, 10 g/L NaCl, 5 g/L yeast extract) supplemented with 2% (w/v) agar. 50 μg/ml kanamycin was used for proper selection of *E. coli* clones.

Protein production and purification. The expression vectors containing the chimeric cell wall hydrolases were chemically transformed into inducible BL21 *E. coli* expression vectors for downstream protein expression and purification. BL21 cells containing the appropriate expression plasmid were grown in 2×YT media overnight at 37° C. with shaking. The next morning, cells were back diluted 1:1000 in flasks containing 50 mL of ZYM-5052 autoinduction media (Fisher Scientific™ Cat No. NC1093977) and incubated with shaking for 2-3 h at 37° C. Flasks were then transferred to 22° C. and incubated with shaking overnight. Cultures were spun down, supernatant was poured off, and pellets were stored at −80° C. for at least 30 min. Each frozen pellet was resuspended in 5 mL of lysis buffer (NPI-10 (100 μM Tris pH 8, 300 mM NaCl, 10 mM imidazole) with the addition of 5 mg lysozyme and 100 units of DNASeI) and incubated at 30° C. with gentle shaking for 30 mins. Cells were then spun down until a clear lysate was obtained and a solid pellet formed. The clear lysate was transferred to a column containing Nickel-NTA Agarose Resin (Gold Biotechnology®) suspended in NPI-10. Columns were inverted several times to completely resuspend the resin and were then incubated at 4° C. for a minimum of 1 h to allow for protein binding. Once the resin was completely settled, the lysate was allowed to run off the column and the columns were washed with two column volumes of NPI-20 (100 µM Tris pH 8, 300 mM NaCl, 20 mM imidazole). Proteins were then eluted by adding 3 mL of NPI-250 (100 µM Tris pH 8, 300 mM NaCl, 250 mM imidazole) and fractions were collected. Proteins were quantified and purity checked via Bradford assay and SDS-PAGE gel and Coomassie staining. Proteins were then concentrated and buffer exchanged into protein storage buffer (50 mM Tris pH 6.8, 300 mM NaCl) using Amicon® Ultra-15 Filter Units. For long term storage, proteins were stored at −80° C. with 30% glycerol.

Example 2: Experimental Assays to Test Anti-*Staphylococcus* Activity of Illustrative Chimeras The chimeras of Example 1 were tested in various assays to determine activity against different *Staphylococcus* sp., as described in the Examples below, using the following materials and methods.

Bacterial strains and culture conditions. After purification of the proteins in Example 2, the chimeric enzymes were tested for lytic activity against *Staphylococcus* sp., as described in the Examples below. All the staphylococcal strains were grown in tryptic soy broth (TSB; BD Difco™, Franklin Lakes, NJ) at 37° C. with shaking or on TSB plates containing 2% (w/v) agar.

Turbidity Reduction Assays. Lytic activity of chimeric cell wall hydrolases were assayed via turbidity reduction assay as described in the art. Briefly, *Staphylococcus* sp. of interest were grown overnight in TBS at 37° C. with shaking. In the morning, cells were diluted back and allowed to grow to exponential phase (OD600~0.5) in TBS at 37° C. with shaking (~2-3 hours). Approximately $1\times10^6$ cells per reaction were then mixed with 2-fold dilutions of purified protein (e.g., the chimeric enzymes and/or controls at example concentrations of 12 µg/mL to 0.75 µg/mL) in a final volume of 200 µl of PBS in a flat bottom microtiter plate. The OD600 of each well was then measured every two to five minutes using a microplate reader. Lytic activity of the cell wall hydrolases leads to a loss of *Staphylococcus* cell integrity, which leads to a reduction in the OD600 reading. More rapid decreases in optical density are correlated with higher enzymatic activities. Specific activity was calculated as described in Briers et al., "A standardized approach for accurate quantification of murein hydrolase activity in high-throughput assays," *J Biochem Biophys Methods* 2007; 70(3):531-3, incorporated by reference herein.

Thermostability Assays. To test thermostability of proteins, an aliquot of the protein was incubated for 30 min at temperatures ranging from 37° C. to 54° C. Proteins were then immediately tested in room temperature turbidity reductions assays as described above. Activity results from heat-exposed proteins were compared amongst each other to evaluate each enzyme's ability to maintain activity after exposure to a range of temperatures, with results at 37° C. serving as a positive control for enzyme activity.

pH Assays. To test the activity of an enzyme over a range of pH values, cells and enzymes were resuspended in buffers at each pH value and were then tested in turbidity reduction assays as described above. The buffers were as follows: PBS pH 7.4; Tris pH 6.8+120 mM NaCl; Citrate buffer pH 6.5+120 mM NaCl; Citrate buffer pH 6.2+120 mM NaCl; Citrate buffer pH 5.7+120 mM NaCl; Citrate buffer pH 5.3+120 mM NaCl; Citrate buffer pH 4.9+120 mM NaCl; Citrate buffer pH 4.5+120 mM NaCl.

Minimum Inhibitory Concentration (MIC) Assays. The MIC of a protein was determined by a conventional broth microdilution technique in TSB (CLSI. Methods for Dilution Antimicrobial Susceptibility Tests for Bacteria that Grow Aerobically, 11th ed. CLSI standard M07. Clinical and Laboratory Standards Institute; 2018.). Briefly, progressive two-fold dilutions of the protein were added to a microtiter plate, with each well containing $1\times10^6$ cells of the target Staphylococcal sp. The MIC was defined as the lowest protein concentration that inhibited visible bacterial growth after 20-24 h incubation at 37° C.

Quantitative Killing Experiments. The antimicrobial activities of chimeric cell wall hydrolases were assayed via quantitative killing assays as described in the art. Briefly, *Staphylococcus* sp. of interest were grown overnight in TBS at 37° C. with shaking. In the morning, cells were diluted back and allowed to grow to exponential phase (OD600~0.5) in TBS at 37° C. with shaking (~2-3 h). Approximately $1\times10^6$ cells per reaction were then mixed with the desired amount of protein in a final volume of 200 µl of TSB media and incubated at room temperature. At the appropriate time points (e.g., 0 time point and the 2 h time point), 20 µL of the reaction was removed and serial dilutions were plated on TSB agar plates and grown for ~16 hours at 37° C. CFUs were then counted to calculate the number of viable cells.

Checkerboard Assays. Standard checkerboard assays were used to measure potential synergistic activity produced by a combination of chimeric CWHs. This assay measures the minimum inhibitory concentration (MIC) of the combined proteins in double serial dilution. Briefly, in a 96-well microtiter plate, columns 1-11 contained 2-fold serial dilutions of Protein A while rows A-G contained 2-fold serial dilutions of Protein B. Row H contained Protein A alone and column 12 contained Protein B alone, which served as controls for measuring the MIC's of Protein A and B alone. Approximately $1\times10^6$ *S. aureus* cells were added to each well in a final combined volume of 200 µL of TSB. Visible growth of *S. aureus* was assessed after 20-24 hours of incubation at 37° C. To quantify the potency of the combination of antibiotics in comparison to their individual activities, the Fractional Inhibitory Concentration (FIC) index value for each combination of proteins was calculated using the following equation:

$$\frac{A}{MIC_A} + \frac{B}{MIC_B} = FIC_A + FIC_B = FIC \text{ Index,}$$

where A and B are the concentration of each protein in a given well; $MIC_A$ and $MIC_B$ are the MIC's of each protein individually; $FIC_A$ and $FIC_B$ are the fractional inhibitory concentrations for protein A and B, respectively, and their sum gives the overall FIC index for that well. The criteria for a determination of synergistic activity were: i) no detectable growth of *S. aureus* within the well, and ii) an FIC index less than or equal to 0.5.

Example 3: LysSA12-PlySs2, LysSA12-LysA72, and LysSA12-ALE-1 Chimeric CWHs Show High Selectivity for *S. aureus* Over *S. epidermidis* in MIC Assays As described in Example 1, the present inventors created chimeric cell wall hydrolases by combining CWH CBDs and EADs in novel combinations. MIC experiments were performed on chimeric CWHs comprising the LysSA12 EAD fused to a set of 6 CBDs from CWHs with anti-*Staphylococcus aureus* activity (PlySs2, LysA72, LysH5, PALS1, ALE-1, and LysA97). MIC experiments were performed, as described in Example 2, to test the activity of these enzymes against both *S. aureus* and *S. epidermidis*.

Results: The results of the minimum inhibitory concentration (MIC) assays against *S. aureus* and *S. epidermidis* are shown in FIG. 1. All tested chimeric CWHs had activity against *S. aureus*. The MIC values against *S. aureus* ranged from 1 μg/mL to 50 μg/mL. The LysSA12 EAD+PALS1 CBD and LysSA12+LysSA97 chimeric proteins showed no selectivity for *S. aureus* over *S. epidermidis* as they had equal MIC values against both *Staphylococcus* species, while the LysSA12 EAD+LysH5 CBD chimera showed relatively low selectivity for *S. aureus* over *S. epidermidis* (4×). By contrast, surprisingly, the LysSA12 EAD+PlySs2 CBD, LysSA12 EAD+LysA72 CBD, and LysSA12 EAD+ALE-1 CBD chimeric CWHs were strongly selective for *S. aureus* over *S. epidermidis* (32×-128×). These results demonstrate that not all active chimeric proteins containing the LysSA12 EAD were selective for *S. aureus* over *S. epidermidis*, which suggests that the LysSA12 domain does not have inherent selectivity for *S. aureus*, but certain chimeric combinations comprising this domain show remarkable selectivity.

Example 4: Selectivity of Illustrative Chimeric CWHs Arises from Particular Combination of CBD and EAD To investigate whether the selectivity of the LysSA12 EAD+PlySs2 CBD, LysSA12 EAD+LysA72 CBD, and LysSA12 EAD+ALE-1 CBD chimeric CWHs was due to the CBD, the inventors generated a second set of chimeric proteins fusing the same three CBDs (PlySs2, LysA72, and ALE-1 CBDs) to the EADs of three other CWHs with anti-*Staphylococcus* activity: Twort, LysCSA5, and LysCSA13. Similar to the EAD of LysSA12, the Twort, LysCSA5, and LysCSA13 EADs are classified as CHAP domains (cysteine, histidine-dependent aminohydrolases/peptidases).

This second set of chimeric proteins was assayed in MIC experiments against both *S. aureus* and *S. epidermidis*, performed as described in Example 2.

Figure 2:
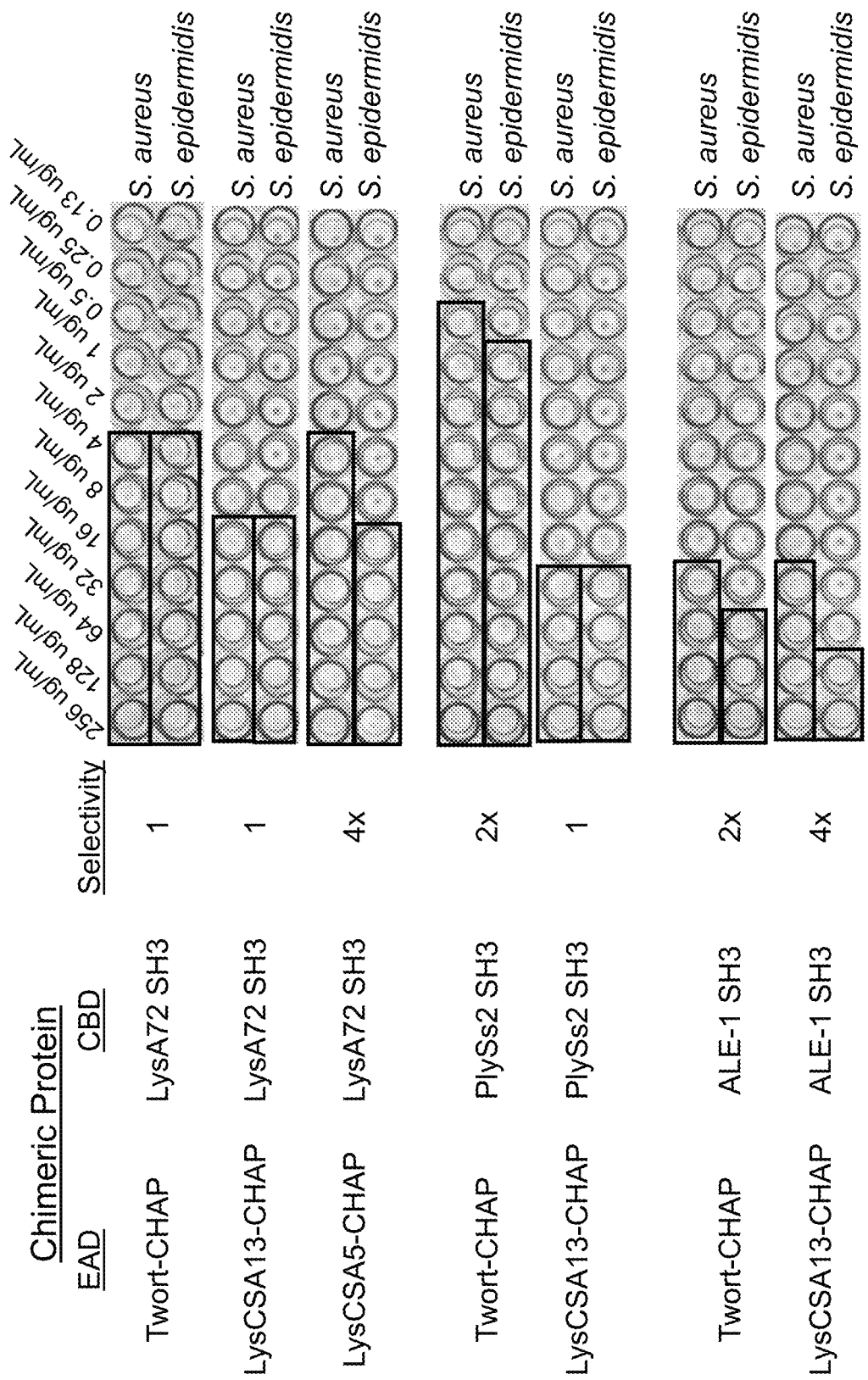
FIG. 2 shows Minimum Inhibitory Concentration (MIC) assay results against *Staphylococcus aureus* and *Staphylococcus epidermidis* for chimeric cell wall hydrolases comprising the Twort, LysCSA13, or LysCSA5 CHAP domains fused to the LysA72, PlySs2, or ALE-1 SH3 domains. Boxes indicate growth inhibition.
Figure 4A:
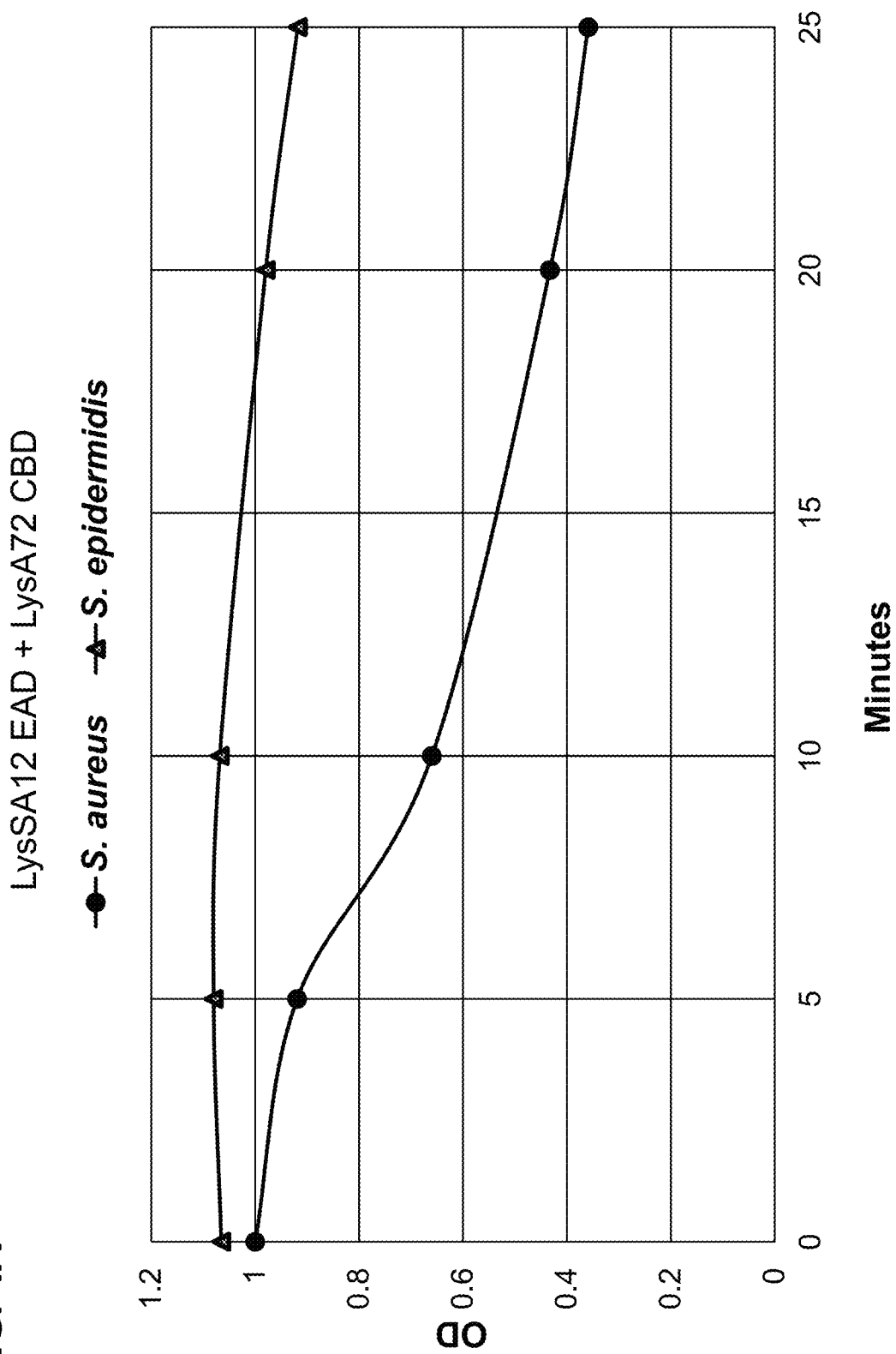
FIG. 4A-4D show turbidity reduction assay results for illustrative chimeric cell wall hydrolases of the disclosure compared to a Twort EAD+PlySs2 CBD chimera. Results are shown for the following chimeras: LysSA12 EAD+LysA72 CBD (FIG. 4A); LysSA12 EAD+PlySs2 CBD (FIG. 4B); LysSA12 EAD+ALE-1 CBD (FIG. 4C); and Twort EAD+PlySs2 CBD (FIG. 4D).
Figure 4B:
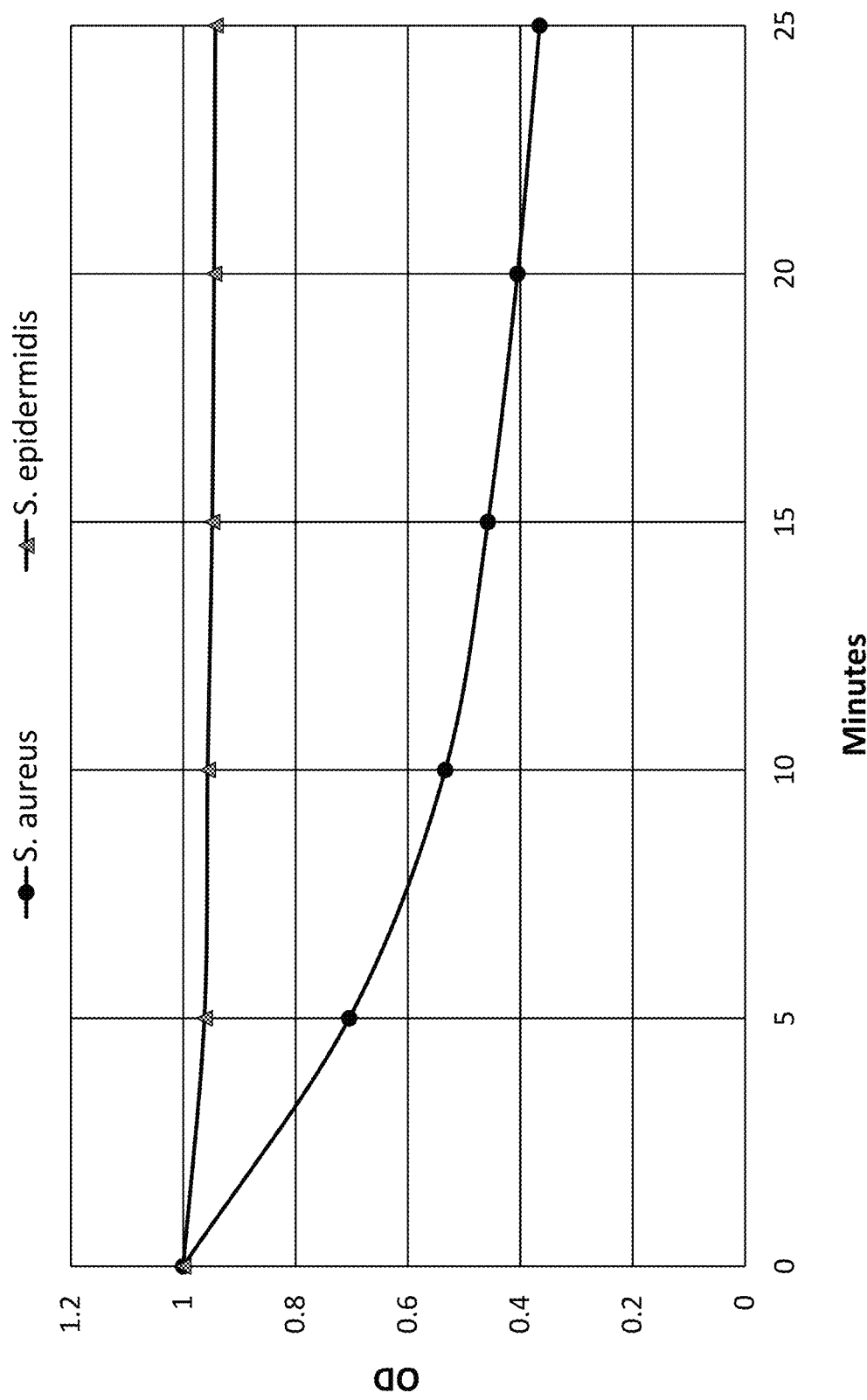
Figure 4C:
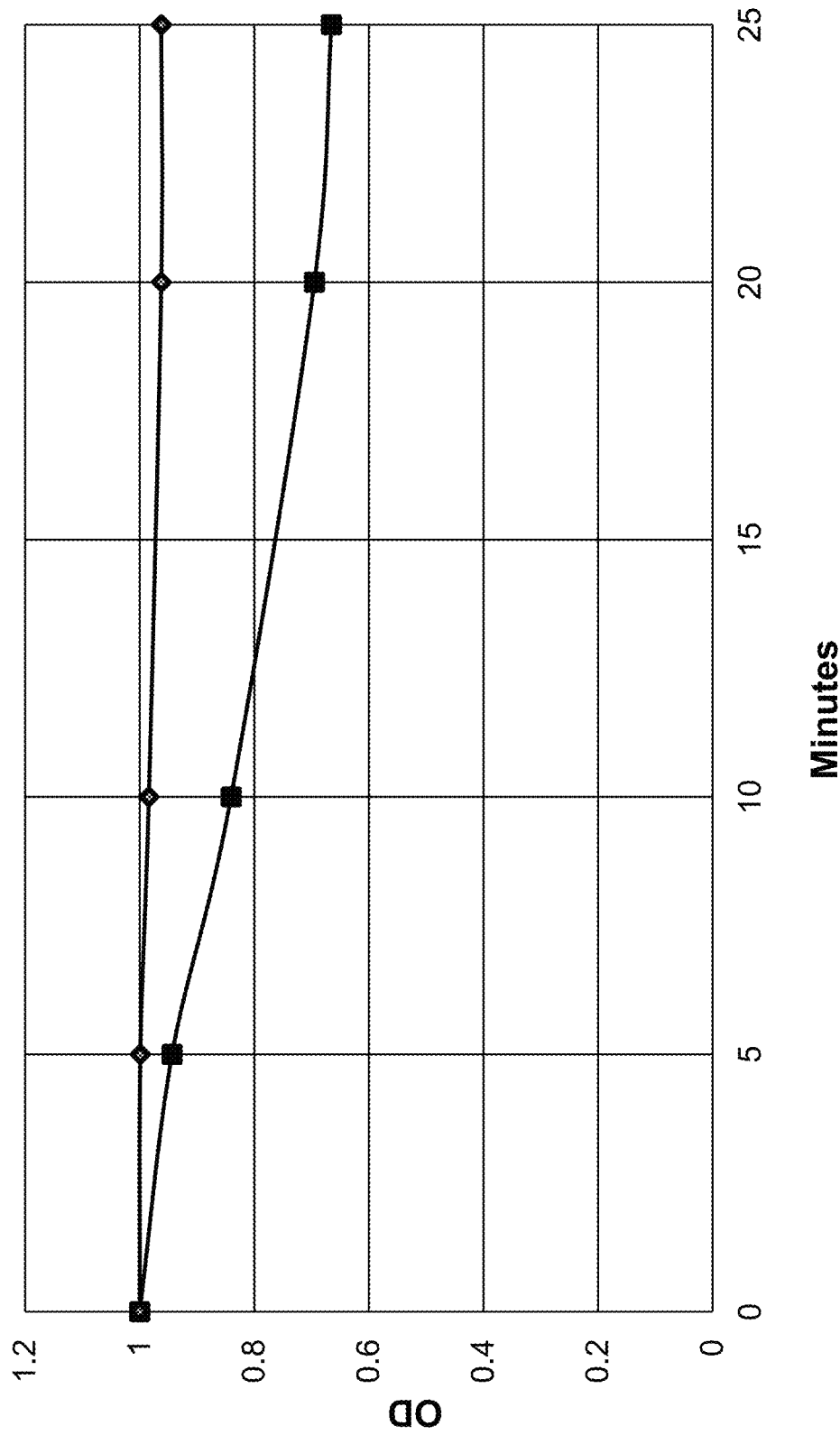
Figure 4D:
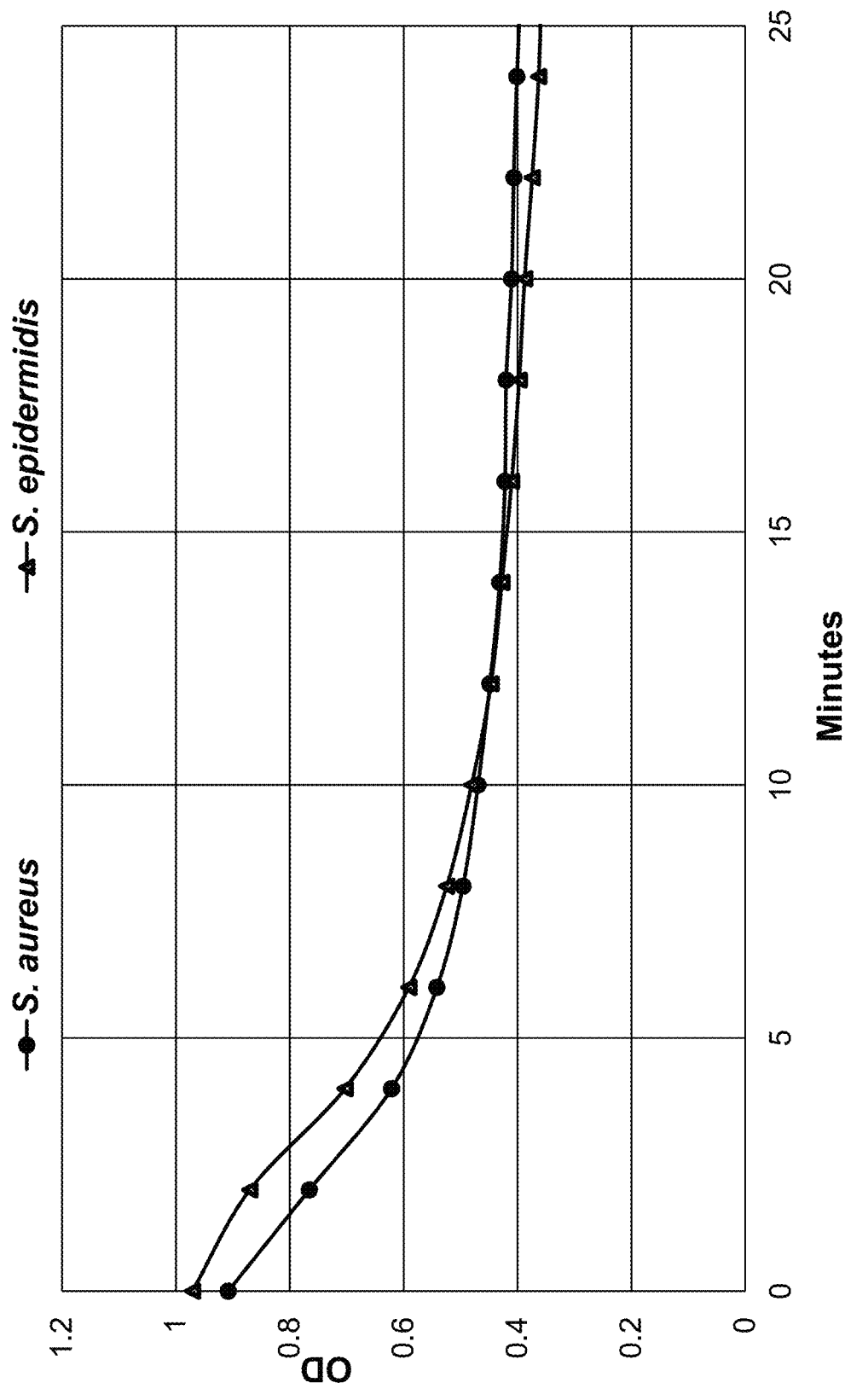
Figure 5A:
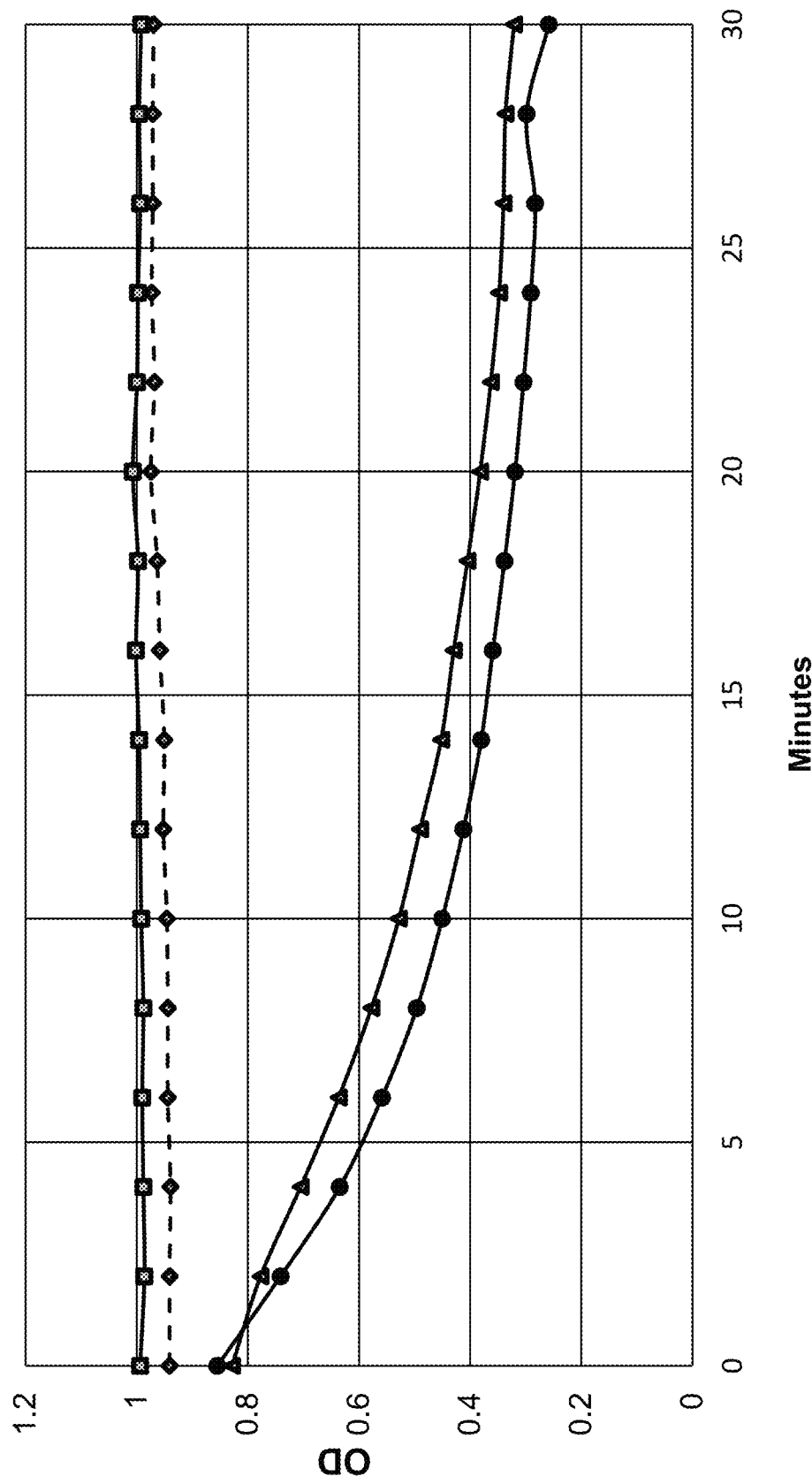
FIG. 5A-5D show thermostability assay results for chimeric cell wall hydrolases of the disclosure, as compared to a Twort EAD+LysA72 CBD chimera. Results are shown for the following chimeras: LysSA12 EAD+LysA72 CBD (FIG. 5A); LysSA12 EAD+PlySs2 CBD (FIG. 5B); LysSA12 EAD+ALE-1 CBD (FIG. 5C); and Twort EAD+LysA72 CBD (FIG. 5D).
Figure 5B:
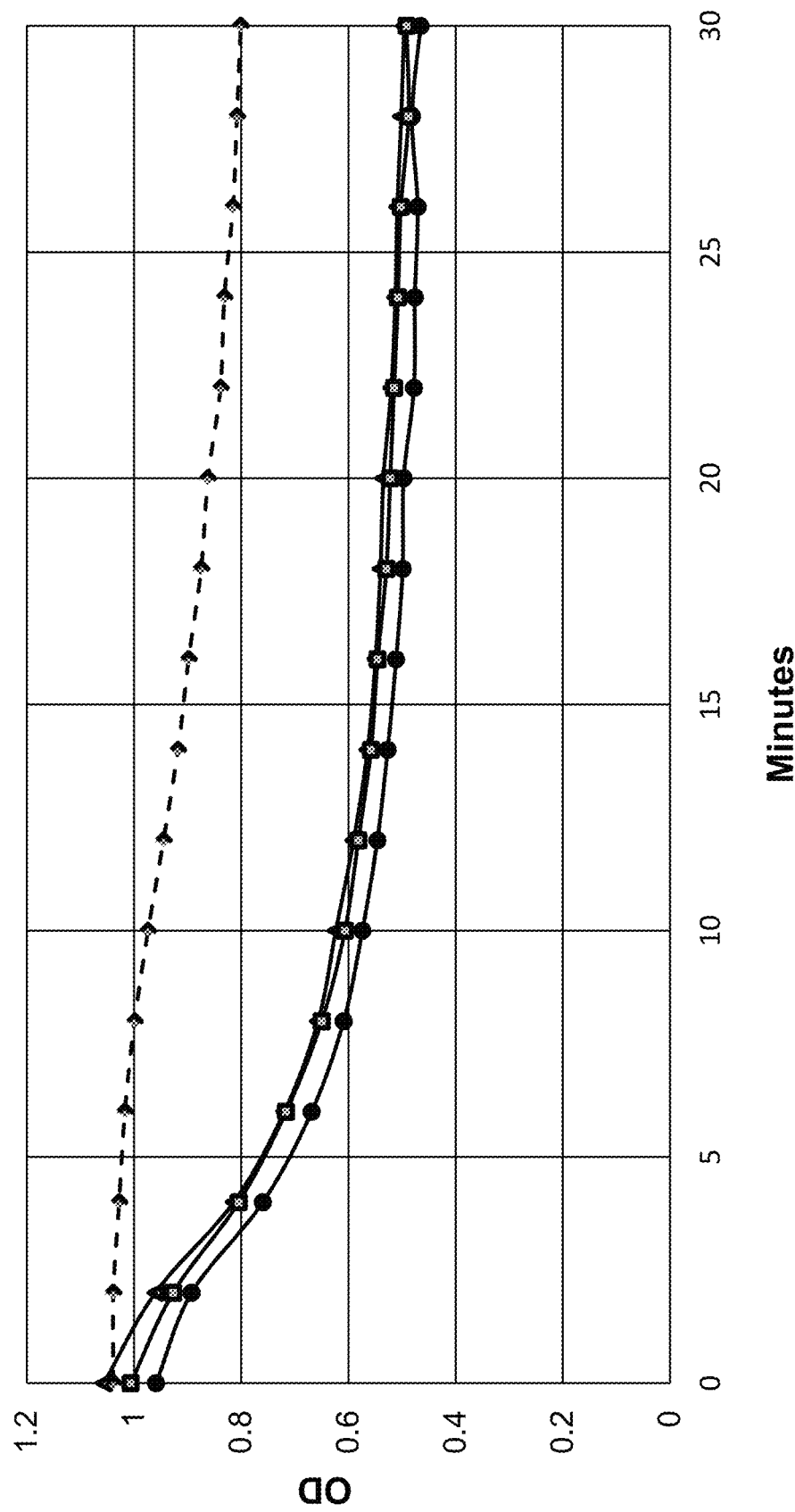
Figure 5C:
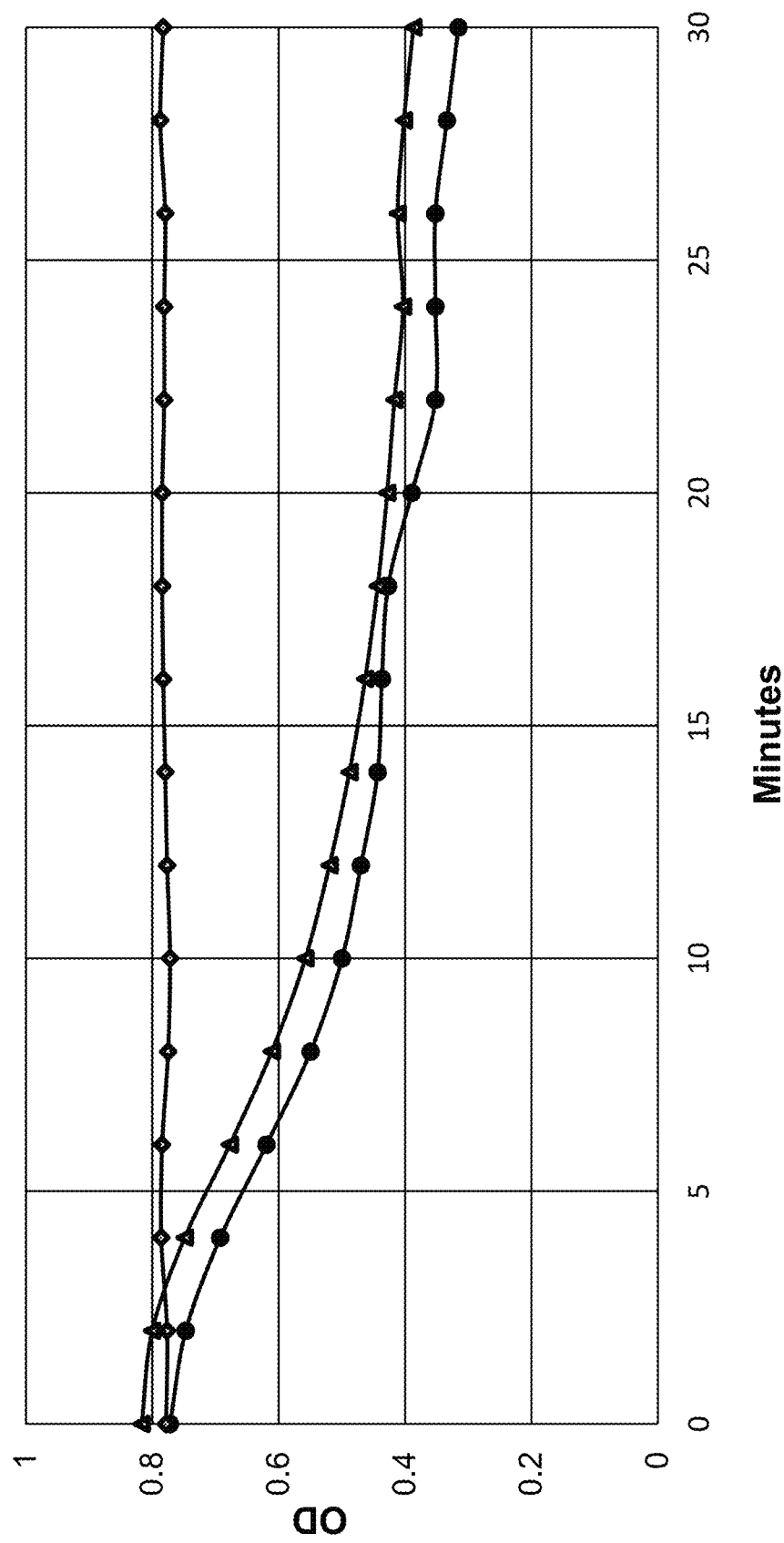
Figure 5D:
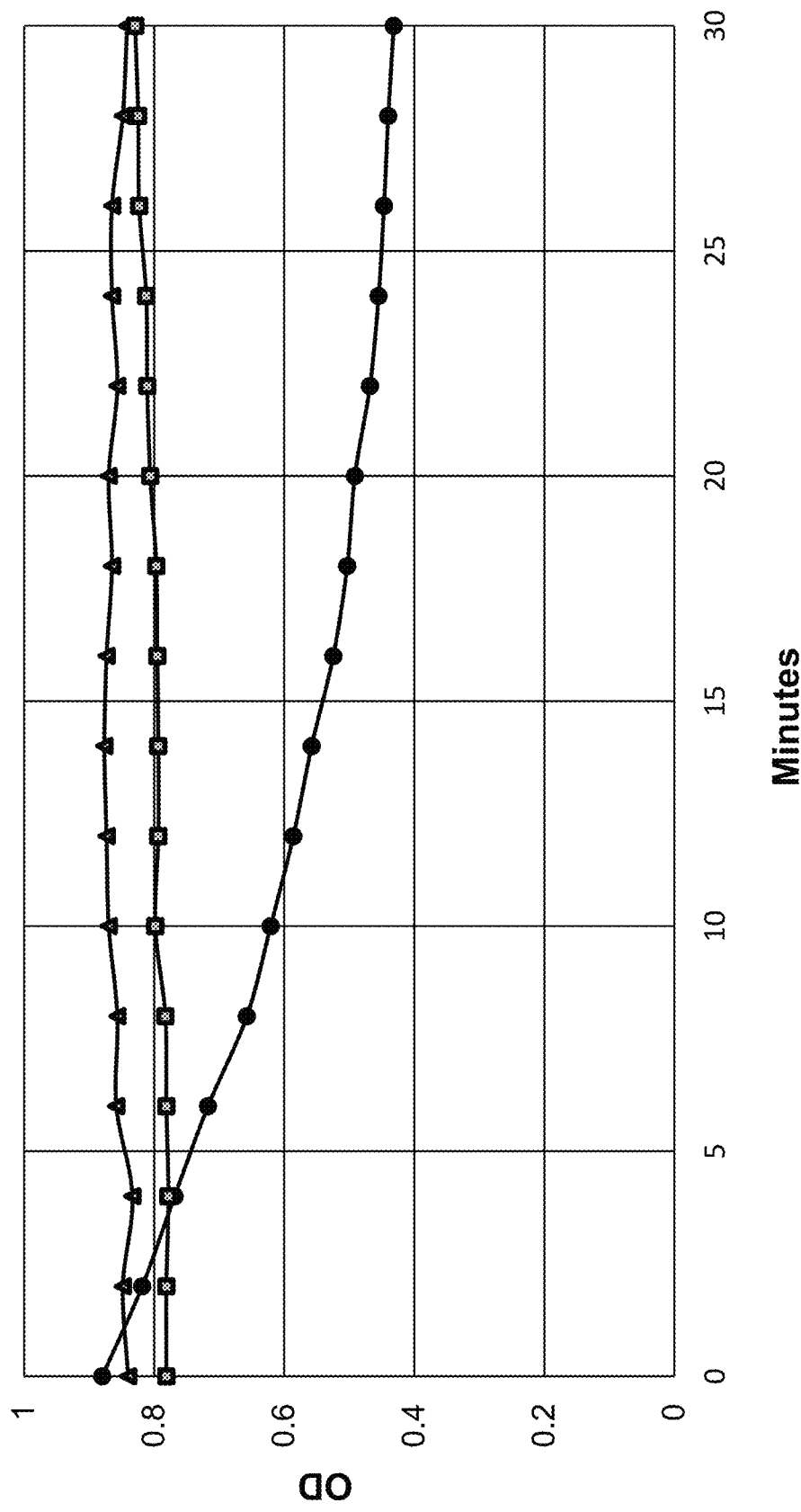

Results: The results of the MIC assays are shown in FIG. 2. All nine chimeric proteins were active against both *S. aureus* and *S. epidermidis* and did not display any significant selectivity for one species over the other, suggesting that the LysSA12 EAD, the PlySs2 CBD, the LysA72 CBD, and ALE-1 CBD are not inherently selective. Instead, selectivity emerged from the unique combinations of LysSA12 EAD+PlySs2 CBD, LysSA12 EAD+LysA72 CBD, and LysSA12 EAD+ALE-1 CBD. The MIC and selectivity data are summarized in FIG. 3, which illustrates that selectivity was not an inherent property of any of the domains tested, but resulted from specific unique combinations.

Example 5: LysSA12-PlySs2, LysSA12-LysA72, and LysSA12-ALE-1 Show High Activity Against and Selectivity for *Staphylococcus aureus* in Turbidity Reduction Assays To further test the selectivity of the LysSA12 EAD+PlySs2 CBD, LysSA12 EAD+LysA72 CBD, and LysSA12 EAD+ALE-1 CBD chimeric CWHs, each chimera was tested in turbidity reduction assays, performed as described in Example 2, for activity against both *S. aureus* and *S. epidermidis*. The Twort EAD+PlySs2 CBD chimera was included as a control, since it showed nearly equivalent activity against both strains in an MIC experiment (Example 4). The Twort EAD+PlySs2 CBD chimera was tested at 12 μg/mL. The LysSA12 EAD+PlySs2 CBD and LysSA12 EAD+ALE-1 CBD were tested at 6 μg/mL. The LysSA12 EAD+LysA72 CBD was tested at 3 μg/mL.

Results: The results of the turbidity reduction assays are shown in FIG. 4A-4D. Consistent with the results from the MIC assays, each of the LysSA12 EAD+PlySs2 CBD, LysSA12 EAD+LysA72 CBD, and LysSA12 EAD+ALE-1 CBD chimeric CWHs were found to have strong lytic activity towards *S. aureus* as demonstrated by a larger and more rapid decrease in the optical density of *S. aureus* in the reaction, but were much less active towards *S. epidermidis*. As a control, the Twort-PlySs2 chimera was found to have equivalent activity against *S. aureus* and *S. epidermidis*.

Example 6: Illustrative Chimeras Show Thermostability Up to 45-51° C.

Thermostability of enzymes is an important factor in potential commercial applications. In the case of enzymes targeting *S. aureus*, many CWHs have very limited thermotolerance. To assess the thermostability of the LysSA12 EAD+PlySs2 CBD, LysSA12 EAD+LysA72 CBD, and LysSA12 EAD+ALE-1 CBD chimeric CWHs, aliquots of each enzyme were tested in thermostability assays, performed as described in Example 2, in which they were incubated for 30 min at temperatures ranging from 37-54° C. and then tested in a standard turbidity reduction assay at room temperature. The Twort EAD+LysA72 CBD was included for comparison.

Results: Results of the thermostability assays are shown in FIG. 5A-5D. The Twort-LysA72 chimera exhibited the least thermostability, as it only showed activity after exposure to 37° C., but was rendered inactive after incubation at 45° C. Both LysSA12-LysA72 and LysSA12-ALE-1 were more stable and retained activity at 45° C. LysSA12-LysA72 was inactive after incubation at 48° C. and LysSA12-ALE-1 was inactive after incubation at 50° C. LysSA12 EAD+PlySs2 CBD demonstrated remarkable thermostability, retaining full activity up to 51° C., and even demonstrating limited activity after incubation at 54° C.

Example 7: LysSA12 EAD+PlySs2 CBD Demonstrates Selectivity for *S. aureus* Over Multiple Other *Staphylococcus* Strains To ensure that the selectivity of LysSA12 EAD+PlySs2 CBD was consistent across a wider panel of *Staphylococcus* sp., LysSA12 EAD+PlySs2 CBD was assayed in turbidity reduction assays against 6 *S. aureus* strains, 4 *S. epidermidis* strains, 1 *S. hominis* strain, and 1 *S. simulans* strain. Turbidity reduction assays were conducted as described in Example 2.

Figure 6:
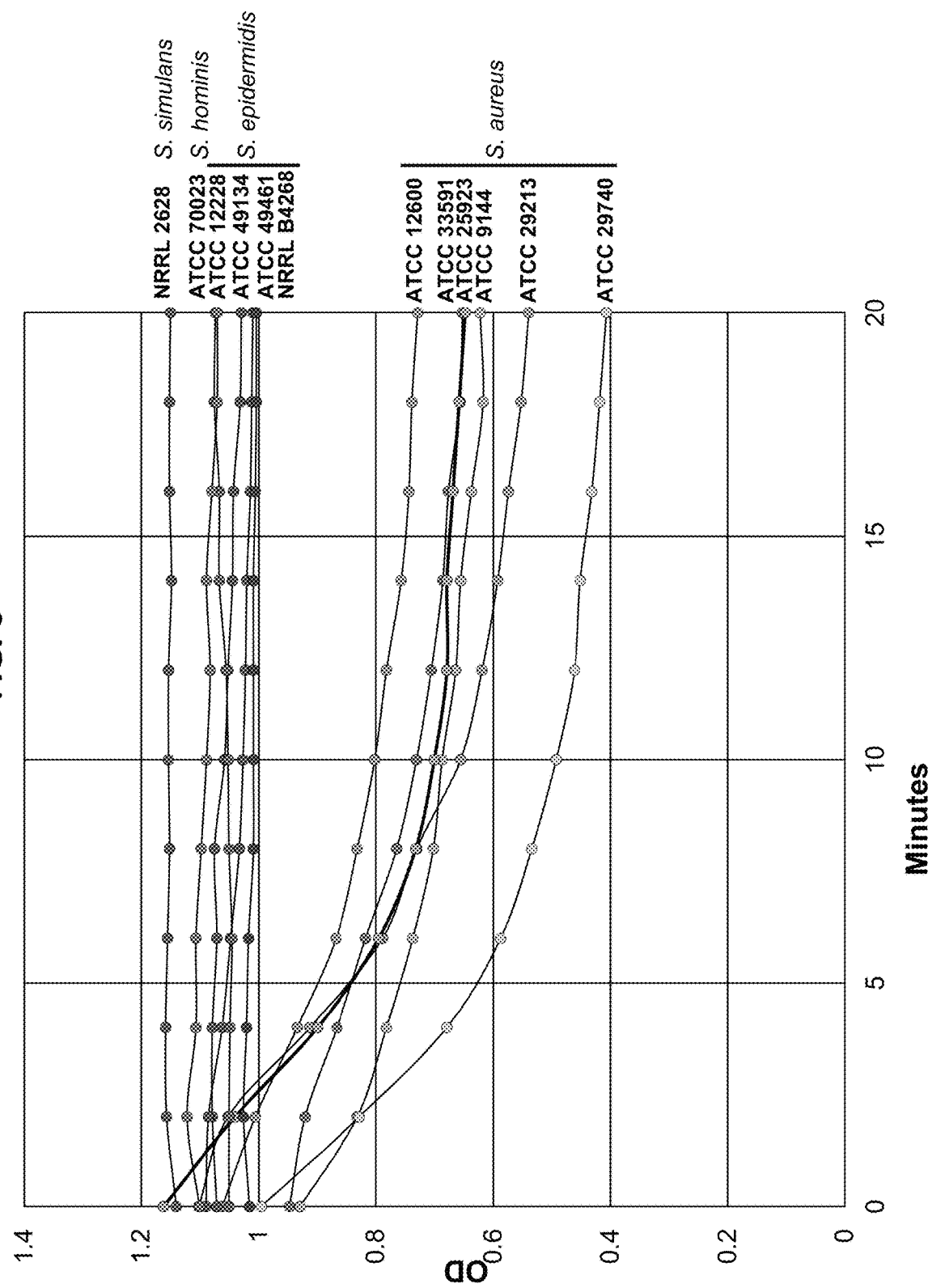
FIG. 6 shows the results of the LysSA12 EAD+PlySs2 CBD chimera in turbidity reduction assays against a variety of *Staphylococcus* sp.

Results: Results of the turbidity reduction assays are shown in FIG. 6. In all cases, *S. aureus* strains were sensitive to lysing by LysSA12 EAD+PlySs2 CBD, while the enzyme demonstrated reduced activity against *S. epidermidis*, *S. hominis*, and *S. simulans* strains.

Example 8: LysSA12 EAD+PlySs2 CBD Chimera Outperforms a Commercially Available Chimeric Endolysin in Terms of Activity and Selectivity SA.100 is a well-known commercialized chimeric endolysin that has been shown to have selectivity for *S. aureus* over *S. epidermidis* (Staphefekt™, see www.staphefekt.com/en/). The activity of LysSA12 EAD+PlySs2 CBD was compared to SA.100 in a turbidity reduction assay against *S. aureus*, performed as described in Example 2. Quantitative killing assays were also performed to compare the effects on cell viability of *S. aureus* and *S. epidermidis* when incubated with SA.100 versus LysSA12 EAD+PlySs2 CBD.

Figure 7B:
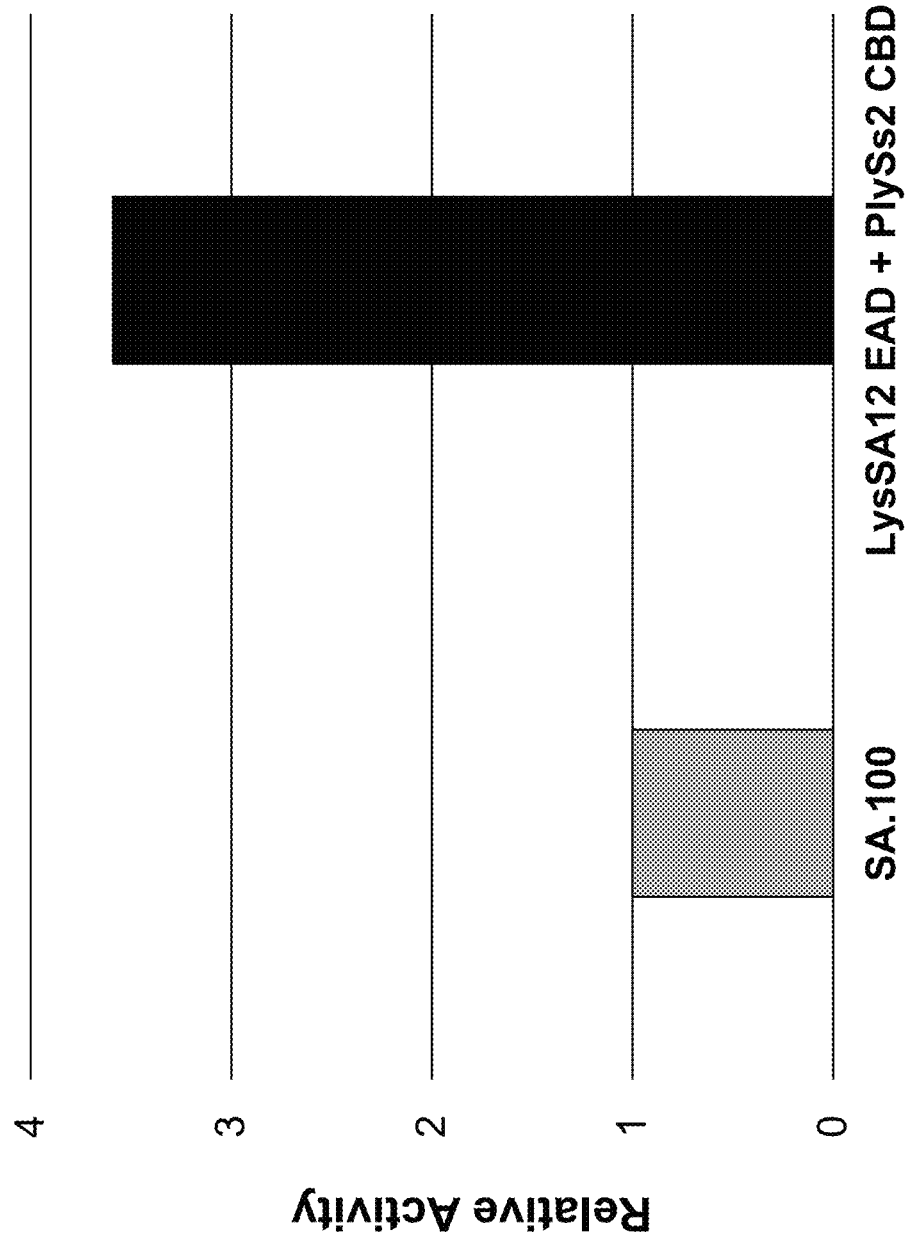

Results: Results of the turbidity reduction assays are shown in FIG. 7A-7B. Relative activity was calculated by normalizing the activity of both enzymes to the SA.100 activity against *S. aureus*. The activity of LysSA12 EAD+PlySs2 CBD was ~3.5 fold higher than that of SA.100 (FIG. 7B), indicating that LysSA12 EAD+PlySs2 CBD is significantly more effective than SA.100 at lysing *S. aureus*.

Figure 8:
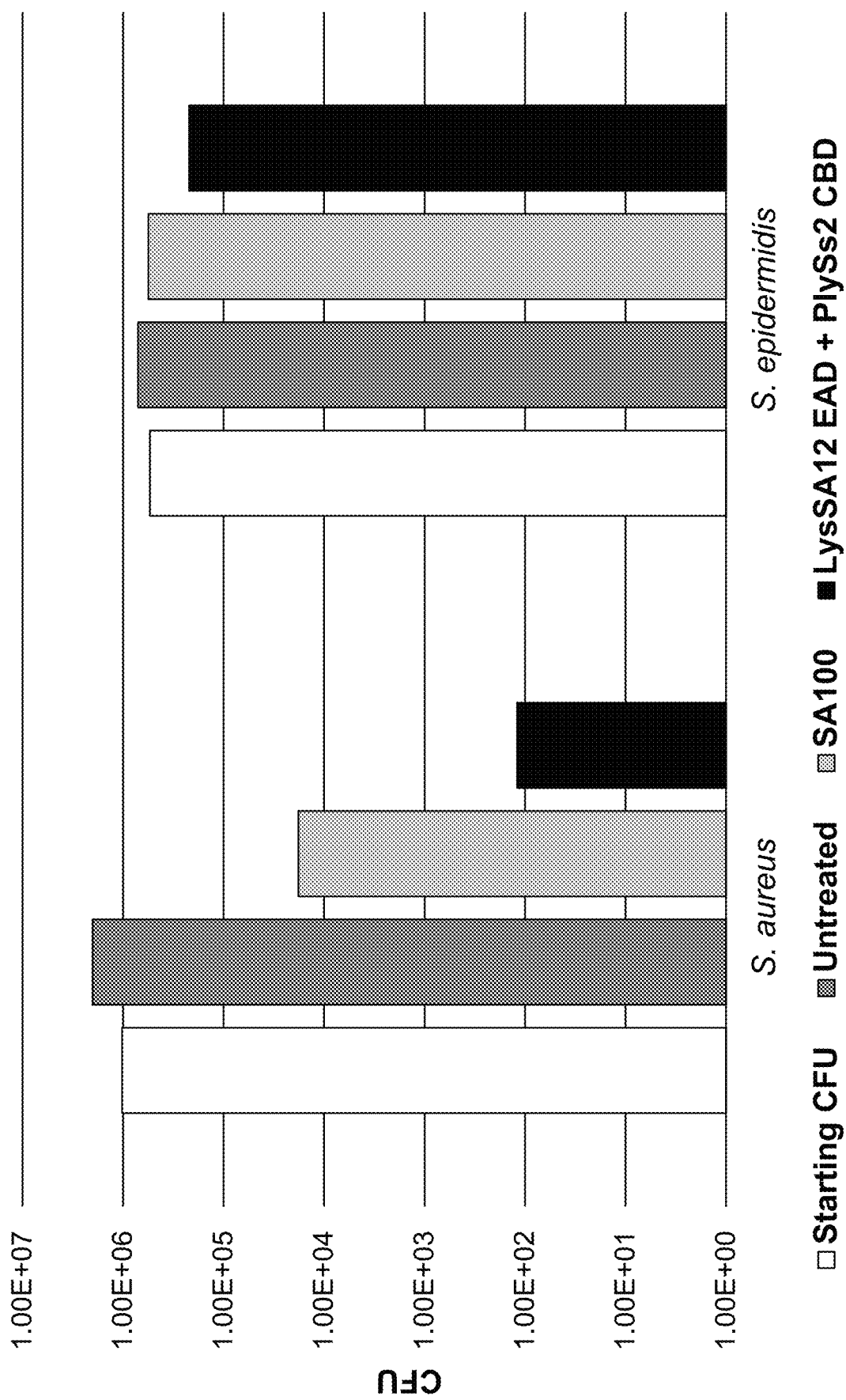
FIG. 8 shows the results of quantitative killing assays for SA.100 vs. the LysSA12 EAD+PlySs2 CBD chimera against both *S. aureus* and *S. epidermidis*.

Results of the quantitative killing assays are shown in FIG. 8. Two hours of incubation with SA.100 resulted in a decrease of 2 orders of magnitude of viable *S. aureus* cells. Remarkably, treatment with LysSA12 EAD+PlySs2 CBD for the same duration resulted in a decrease of 4 orders of magnitude of viable *S. aureus*, again demonstrating that LysSA12 EAD+PlySs2 CBD is significantly more potent than SA.100. Neither SA.100 nor LysSA12 EAD+PlySs2 CBD had significant activity against *S. epidermidis* in these quantitative killing assays, but LysSA12 EAD+PlySs2 CBD had significantly greater fold selectivity for *S. aureus* over *S. epidermidis* than SA.100 did.

Example 9: LysSA12 EAD+PlySs2 CBD Demonstrates pH Tolerance Down to pH 5

To assess the pH tolerance of LysSA12 EAD+PlySs2 CBD in comparison to the commercially available SA.100 enzyme, each enzyme was tested in a pH assay as described in Example 2, testing the enzymes at the following pH values: 7.4, 6.8, 6.5, 6.2, 5.7, 5.3, 4.9, and 4.5.

Figure 9:
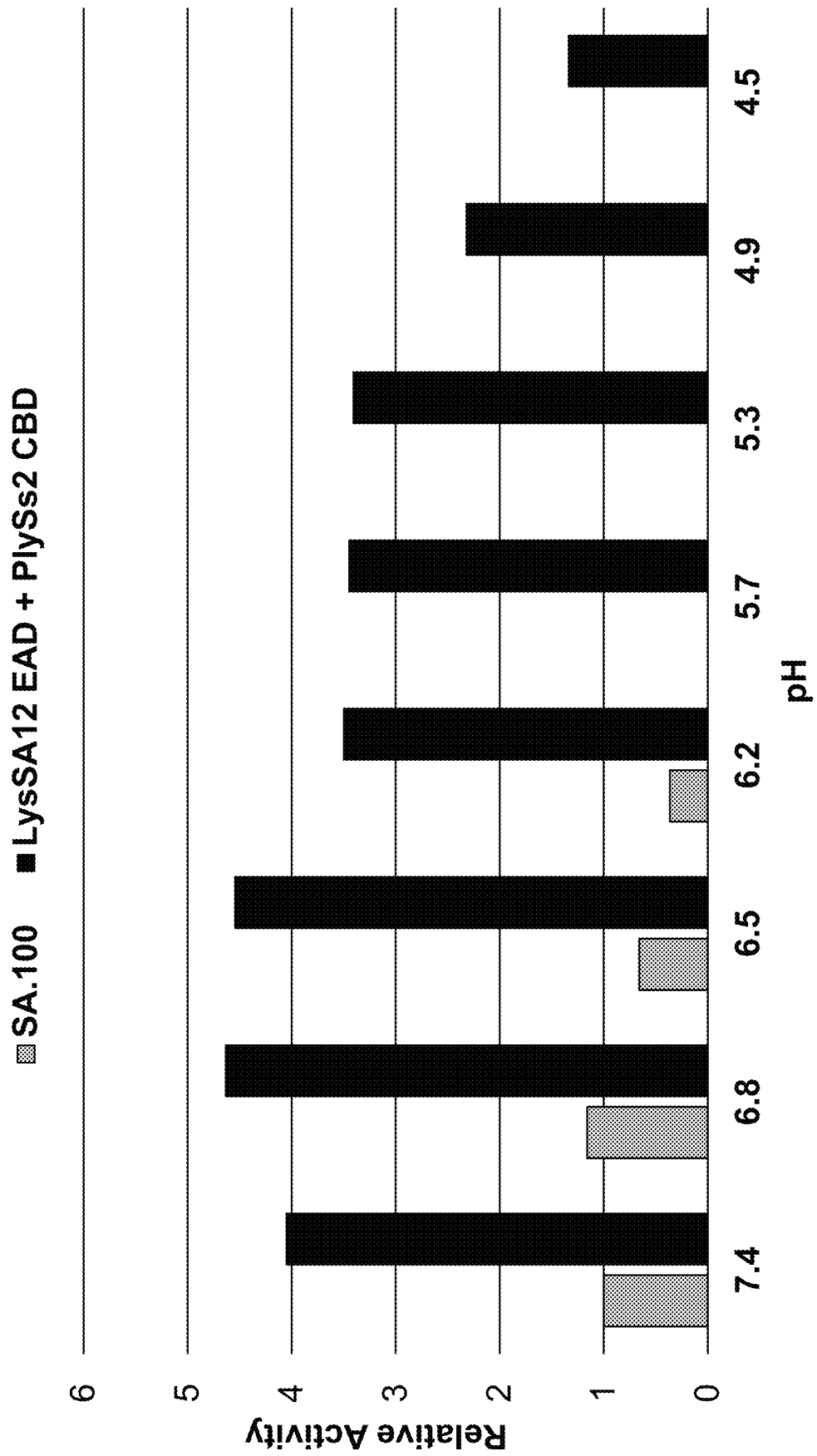
FIG. 9 shows the results of pH assays for SA.100 vs. the LysSA12 EAD+PlySs2 CBD chimera across a range of pH values, from pH 7.4 to pH 4.5.

Results: Results of the pH assays are shown in FIG. 9. Relative activity was calculated by normalizing all activities to the activity of SA.100 at pH 7.4. SA.100 lost all activity below pH 6.2. In contrast, LysSA12 EAD+PlySs2 CBD retained significant activity across all tested pH values, and in fact, demonstrated activity higher than that of SA.100's maximum activity at all pH values. These results demonstrate that LysSA12 EAD+PlySs2 CBD has a much higher pH tolerance than that of the commercially available SA.100 enzyme.

Example 10: *Staphylococcus aureus*-Selective Activity of the LysSA12 EAD+PlySs2 CBD Chimera in a 3D Skin Model of the Skin Microbiome Given the strong, *S. aureus*-selective activity of the LysSA12 EAD+PlySs2 CBD chimeric protein in MIC, turbidity reduction, and quantitative killing assays, the effects of this protein were tested on a 3D skin model of the skin microbiome. In this experiment, reconstituted human epidermis (RHE) was colonized overnight with a mixture of 4 skin bacteria: *Staphylococcus aureus, Staphylococcus epidermidis, Corynebacterium* xerosis, and *Cutibacterium acnes*. The RHE was then treated for 4 hours with solutions of LysSA12 EAD+PlySs2 CBD at 8 µg/mL, SA.100 at 32 µg/mL, or PBS alone. The RHE was washed gently three times and then the remaining adherent bacterial cells were recovered and quantified using quantitative PCR.

Figure 10:
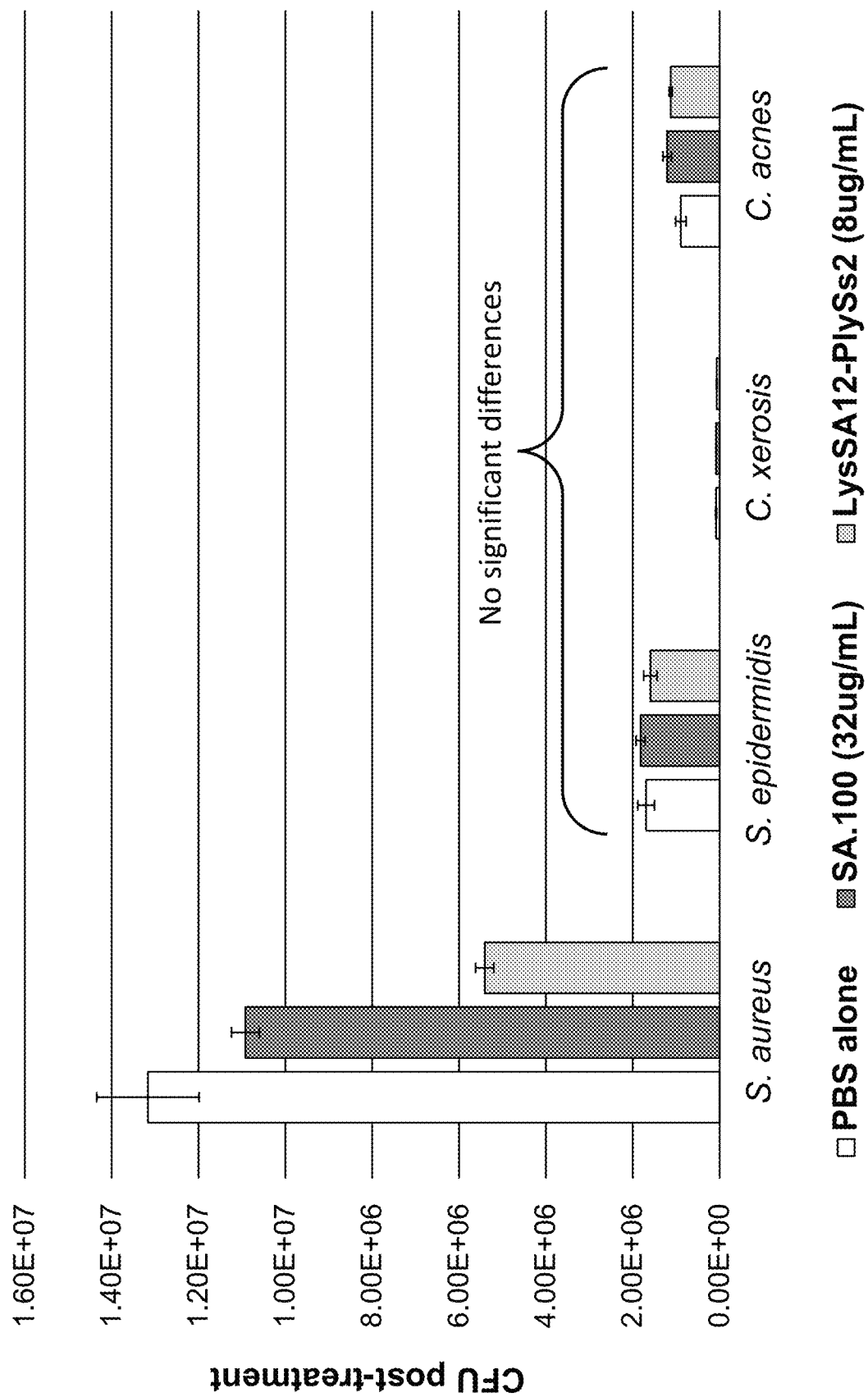
FIG. 10 shows the results of an assay testing the effect of the LysSA12 EAD+PlySs2 CBD chimera compared to SA.100 or PBS alone in a 3D skin model of the skin microbiome. Error bars represent the standard error of the mean of 3 biological replicates.

Results: Results are shown in FIG. 10. Treatment with LysSA12 EAD+PlySs2 CBD resulted in a 3-fold greater decrease in adherent *S. aureus* cells compared to SA.100. No significant differences were observed in the amount of *S. epidermidis, C. xerosis*, or *C. acnes* among the three treatment groups, showing that treatment with LysSA12 EAD+PlySs2 CBD results in a highly selective reduction in *S. aureus* consistent with the results of preceding examples.

Example 11: Prophetic Synergistic Anti-*Staphylococcus aureus* Effect from Combination of M23 EAD-Comprising Chimera and CHAP2 EAD-Comprising Chimera The LysSA12 EAD+PlySs2 CBD chimeric protein has a CHAP-family EAD. The inventors theorize that LysSA12 EAD+PlySs2 CBD could work synergistically with a selective enzyme that contains an EAD from a different class. To test this, a standard checkerboard assay is utilized to characterize the activity of combinations of M23S1 EAD+LysH5 CBD (SEQ ID NO: 36) and LysSA12 EAD+PlySs2 CBD (SEQ ID NO: 31) chimeric proteins. Combinations of the two proteins are tested to identify combinations that inhibit growth of *S. aureus* and are calculated to have an FIC index≤0.5 indicating synergistic activity between the two proteins.

Example 12: Prophetic Comparison of Illustrative Chimeras Against Native Cell Wall Hydrolases The LysSA12 EAD+PlySs2 CBD chimeric CWH is compared against native LysSA12 and PlySs2 cell wall hydrolases to compare their *Staphylococcus* species-specific activity.

Limited or no *S. aureus*-selectivity for either native protein would indicate that the remarkable selectivity of the LysSA12 EAD+PlySs2 CBD chimeric enzyme is a property that emerges from the combination of the two domains.

Example 13: LysSA12 EAD+PlySs2 CBD Chimeric CWH Exhibited Strong, Selective Activity Against *S. aureus* Across Multiple Topical Formulations Materials & Methods Formulation: The LysSA12 EAD+PlySs2 CBD chimeric CWH of preceding examples was prepared for topical formulation. Three topical formulations were created: a hydrogel comprising hyaluronic acid (formulation #1), a hydrogel comprising hydroxymethylcellulose (formulation #2), and a cream-based formula comprising cetereth-20/ceteryl alcohol (formulation #3). The two hydrogel formulations combine the hydrating effects of hyaluronic acid or the texture enhancing effects of hydroxymethylcellulose with the beneficial microbiome effects of the CWHs and can be used to treat *Staphylococcus* infection while improving skin quality, while the cream-based formulation allows for the addition of lipid soluble ingredients to the formulation. Each formulation comprised 4 µg/mL of the LysSA12 EAD+PlySs2 CBD chimeric CWH. The formulations were stored at room temperature for 7 days and were then tested for antimicrobial activity against *S. aureus* and *S. epidermidis* using a quantitative killing assay.

Quantitative killing assay: The antimicrobial activity of chimeric cell wall hydrolases was assayed via standard quantitative killing assays. Briefly, *Staphylococcus* sp. of interest were grown overnight in TBS at 37° C. with shaking. In the morning, cells were diluted back and allowed to grow to exponential phase to an OD600 of about 0.5 in TBS at 37° C. with shaking. Approximately 1×10$^6$ cells per reaction were then mixed with 100 µL of the formulation being tested and incubated at room temperature. At the selected time points, 20 µL of the reaction was removed and serial dilutions were plated on TSB agar plates and grown for about 16 hours at 37° C. CFUs were then counted to calculate the number of remaining viable cells.

Results

Figure 11A:
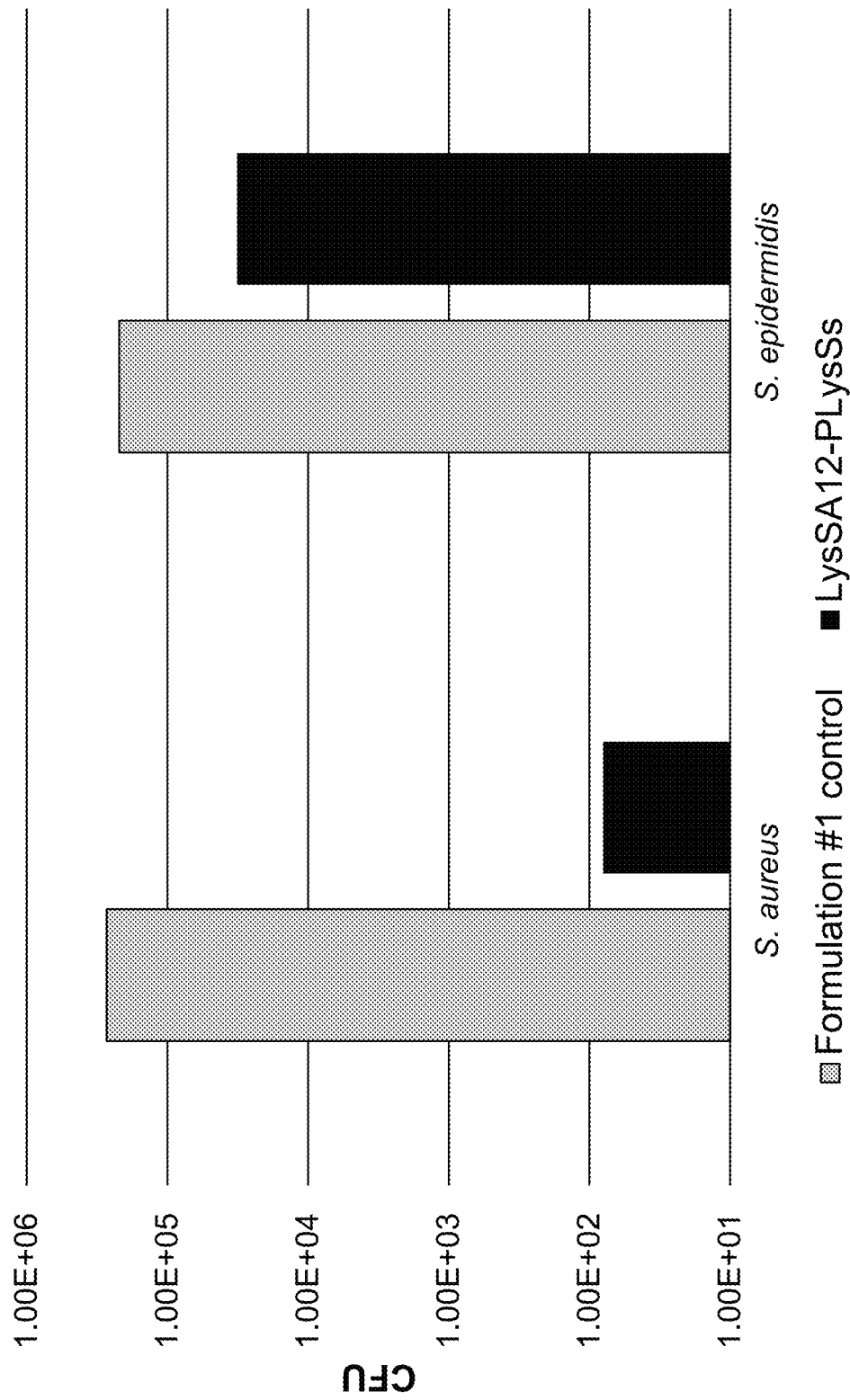
Figure 11B:
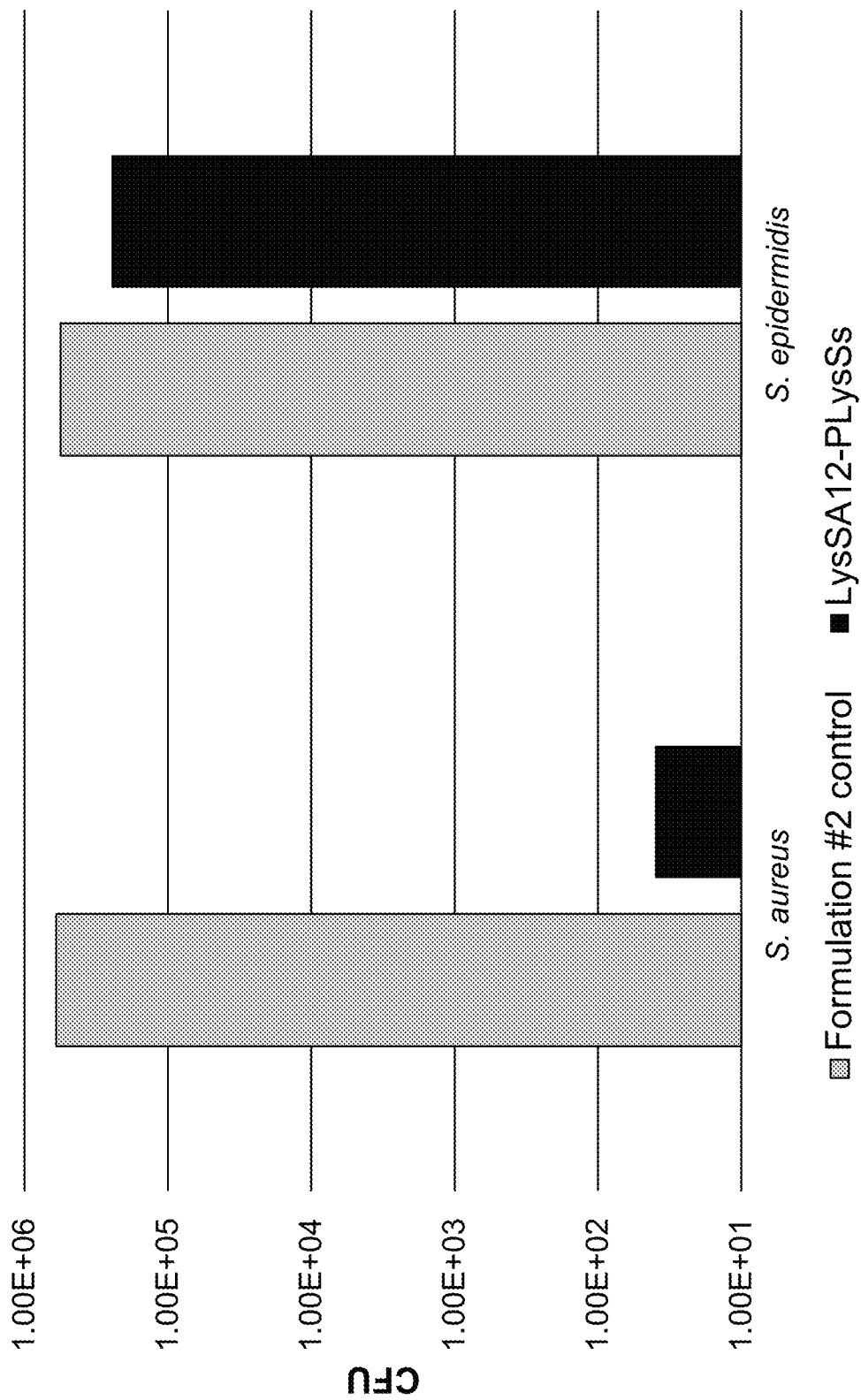

In all three cases, the number of viable CFU of *S. aureus* remaining after two-hour treatment with LysSA12-PlySs2 was reduced 3-4 orders of magnitude compared to less than 1 order of magnitude for *S. epidermidis* (FIG. 11A-11C). Thus, all three formulations exhibited strong, selective killing of *S. aureus* demonstrating the ability of the LysSA12 EAD+PlySs2 CBD chimeric CWH to retain enzymatic activity in a variety of formulation types relevant for topical skin applications.

Example 14: Long-Term Stability of LysSA12 EAD+PlySs2 CBD Chimeric CWH in Topical Formulations Long-term stability of enzyme activity in formulations at room temperature is an important property in the commercial viability of a topical skin care product. Accelerated life testing at elevated temperatures is a common method to determine room temperature shelf life. Four weeks of stability at 45° C. is approximately equivalent to 5-6 months of stability at room temperature based on the Arrhenius function.

An aliquot of Formulation #2 from Example 13 was selected as an exemplary formulation for stability testing. The formulation contained 4 µg/mL of the LysSA12 EAD+PlySs2 CBD chimeric CWH and was stored at 45° C. for 4 weeks. The formulation was tested for antimicrobial activity against *S. aureus* at 1-week, 2-week, and 4-week timepoints using the quantitative killing assay of Example 13.

Figure 12:
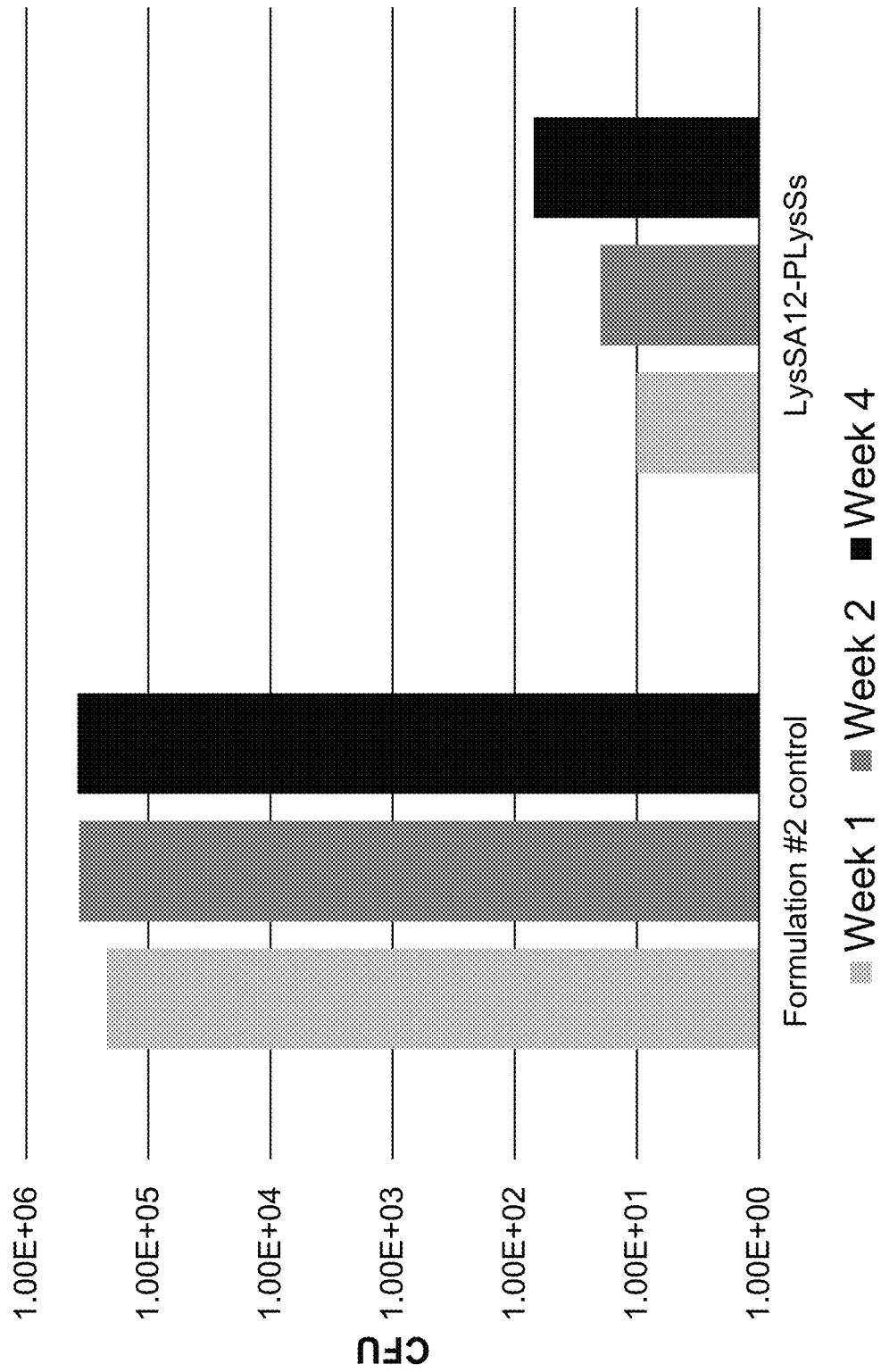
FIG. 12 shows the activity of LysSA12 EAD+PlySs2 CBD chimera comprising topical formulations compared to control at 1 week, 2 weeks, and 4 weeks. Control formulation is identical to the test formulation, but does not contain LysSA12 EAD+PlySs2 CBD protein.

Results are shown in FIG. 12. The enzyme retained significant activity at all timepoints tested, demonstrating the long-term stability of the LysSA12 EAD+PlySs2 CBD chimeric CWH in an illustrative topical skin care formulation.

Example 15: Clinical Trial of Topical Application of LysSA12 EAD+PlySs2 CBD Chimeric CWH Demonstrates Improvement in Nine Skin Parameters Materials & Methods 15.1. Participants A total of 15 male and female participants aged 18-65 were recruited for this study. One participant dropped out of the study. Statistical analysis was performed on the intention-to-treat (ITT) population. All participants satisfied the following inclusion and exclusion criteria.

Inclusion Criteria:
  Male or female aged 18-65.
  Anyone with moderate to severe red, dry, itchy skin in at least one of the following areas: Face, Neck, Ventral forearm(s), Inside elbow(s).
  Is not currently using and has not used oral/topical steroids, oral immunosuppressives, topical/oral antibiotics, antimicrobial baths, prescription creams, or other prescription drugs for treating eczema in the past month.
  Willing to avoid oral/topical steroids, oral immunosuppressives, topical/oral antibiotics, antimicrobial baths, or prescription creams for the two-week study duration.
  Willing and able to discontinue systemic medication or therapy (e.g., oral medications, phototherapy, herbal remedies, or acupuncture) to relieve dry, itchy skin or eczema.

Exclusion Criteria:
  Anyone not in good health.
  Anyone who has any chronic health conditions such as oncological or psychiatric disorders.
  Anyone who has severe allergic reactions that require the use of an Epi-Pen.
  Anyone pregnant, breastfeeding, or attempting to conceive over the next two weeks.
  Anyone who cannot/will not commit to the study protocol.
  Anyone with a history of substance abuse.
  Anyone who has undergone an invasive medical procedure in the three weeks before the study or has a procedure planned during the study duration.
  Anyone with psoriasis, infectious skin diseases, ichthyosis, autoimmune skin diseases like lupus erythematosus or dermatomyositis.

15.2. Study Design and Intervention Procedure

This virtual study required participants to complete questionnaires at home and take before and after photos of the skin. Consent forms describing the study process, instructions, evaluation methods, and bill of rights were provided to participants before study onboarding. Following the consent process, participants took photos of the affected skin, and completed the Baseline questionnaire, which included answering study-specific questions about their skin.

Participants were instructed to apply a LysSA12 EAD+PlySs2 CBD chimeric CWH topical formulation to the affected area(s) in the morning and at night (before bed).

Participants completed questionnaires at the end of Weeks 1 and 2 and took photos at the end of Week 2.

15.3. Data Analysis and Statistics

Data from questionnaires were collected using textual 5-, 9-, or 10-point Likert scales for each question. The textual Likert data was transformed into numerical values, and the score from each question was analyzed independently. Data were checked for normality using the Pearson test. Data were analyzed using a mixed-effects analysis or Kruskal-Wallis test based on the normality of the data, with Dunnett's or Dunn's tests for multiple comparisons, respectively. Statistical analyses were performed in GraphPad Prism 10.0, and the significance level was set at 0.05. For product-specific questions not evaluated at Baseline, results were presented as the percentage of subjects reporting each answer.

Results

The effects of LysSA12 EAD+PlySs2 CBD chimeric CWH application on red, dry, itchy skin and associated outcomes, including pain, sleep, and mood, was measured through questionnaires completed at Baseline, Day 7, and Day 14.

Statistical analysis of the Day 7 questionnaire results revealed that participants experienced improvements in all nine tested parameters, with statistically significant improvements in six parameters (Table 4 and FIG. 13A-13I). This included significant reductions in the number of days participants experienced skin itchiness; the severity and frequency of sleeplessness caused by skin issues; skin dryness; skin roughness; and pain resulting from dry, red, itchy skin.

Statistical analysis of the Day 14 questionnaire results revealed that, after 14 days of LysSA12 EAD+PlySs2 CBD chimeric CWH application, participants experienced statistically significant improvements in all nine tested skin-associated parameters (Table 4 and FIG. 13A-13I). This included significant reductions in the severity of skin itchiness (5.80 to 1.86); the severity (5.27 to 1.29) and frequency (2.60 to 0.57) of sleeplessness caused by skin issues; skin dryness (2.13 to 1.00); skin roughness (2.20 to 1.14); and pain resulting from dry, red, itchy skin (4.00 to 2.14).

TABLE 4

Statistical analysis of changes in skin parameters.

| | Baseline | | Day 7 | | | | Day 14 | | | |
|---|---|---|---|---|---|---|---|---|---|---|
| | Mean | SD | Mean | SD | % Change | P-value | Mean | SD | % Change | P-value |
| Skin Itchiness | 5.80 | 1.82 | 3.79 | 2.22 | −34.73% | 0.0627 | 1.86 | 1.88 | −67.98% | <0.0001* |
| Days of Skin Itchiness | 3.00 | 0.65 | 2.29 | 0.83 | −23.81% | 0.0437* | 1.64 | 1.08 | −45.24% | 0.0006* |
| Sleeplessness | 5.27 | 3.56 | 2.07 | 2.23 | −60.67% | 0.0018* | 1.29 | 1.86 | −75.59% | 0.0005* |
| Frequency of Sleep Disturbed by Skin | 2.60 | 0.91 | 1.00 | 1.04 | −61.54% | 0.0013* | 0.57 | 0.85 | −78.02% | <0.0001* |
| Skin Redness | 2.13 | 0.74 | 1.64 | 1.28 | −22.99% | 0.1443 | 1.00 | 0.78 | −53.12% | 0.0015* |
| Skin Dryness | 2.40 | 0.63 | 1.57 | 1.09 | −34.52% | 0.0291* | 1.14 | 1.03 | −52.38% | 0.0004* |
| Skin Flaking | 2.00 | 0.76 | 1.50 | 1.29 | −25.00% | 0.2944 | 0.71 | 0.83 | −64.29% | 0.0015* |
| Skin Roughness | 2.20 | 0.94 | 1.29 | 0.91 | −41.56% | <0.0001* | 1.14 | 0.77 | −48.05% | 0.0019* |
| Pain Resulting from Dry, Red, Itchy Skin | 4.00 | 2.04 | 2.29 | 1.77 | −42.86% | 0.0447* | 2.14 | 2.32 | −46.43% | 0.0089* |

*Indicates statistically significant outcomes.

On Day 14, participants were asked 18 product perception questions, with the majority responding positively to all 18, and over 70% of participants responding favorably to 14 (Table 5). Notably, 85.71% of participants agreed that the product effectively relieves dry, red, itchy skin and that their skin has been less red and flaky since using it. In terms of their overall satisfaction with the product, 71.43% of participants agreed that their skin was the best it had been in months, while 78.57% stated that they would like to add the product to their usual skin management regimen. A substantial 78.57% also agreed that they would recommend the product to friends and family.

TABLE 5

Participants' perceptions of the impact of the LysSA12 EAD + PlySs2 CBD chimeric CWH application on symptoms and overall satisfaction.

| Statement | % Agreement on Day 14 |
|---|---|
| This product gives effective relief to dry, red, itchy skin. | 85.71%* |
| My skin has been less itchy since using this product. | 78.57%* |
| My skin has been less red since using this product. | 85.71%* |
| My skin has been less dry since using this product. | 64.29% |
| My skin has been less flaky since using this product. | 85.71%* |
| This product is non-irritating. | 78.57%* |
| This product soothes my skin. | 78.57%* |
| This product gives instant relief to dry, itchy skin. | 64.29% |
| My skin health has improved since using this product. | 78.57%* |
| My skin has been less sensitive since using this product. | 64.29% |
| This product is more effective than previous emollient creams that I have used. | 71.43%* |
| This product feels nice on my skin. | 71.43%* |
| My skin is less rough since using this product. | 78.57%* |
| My skin is the best it has been in months. | 71.43%* |
| This product has reduced the size of my dry skin areas. | 71.43%* |
| I would like to continue using this product instead of my usual products to manage my dry and itchy skin. | 64.29% |
| I would like to add this product to my usual regimen that I use to manage my dry and itchy skin. | 78.57%* |
| I would recommend this product to my friends and family. | 78.57%* |

*Indicates over 70% positive response rate.

Figure 14A:
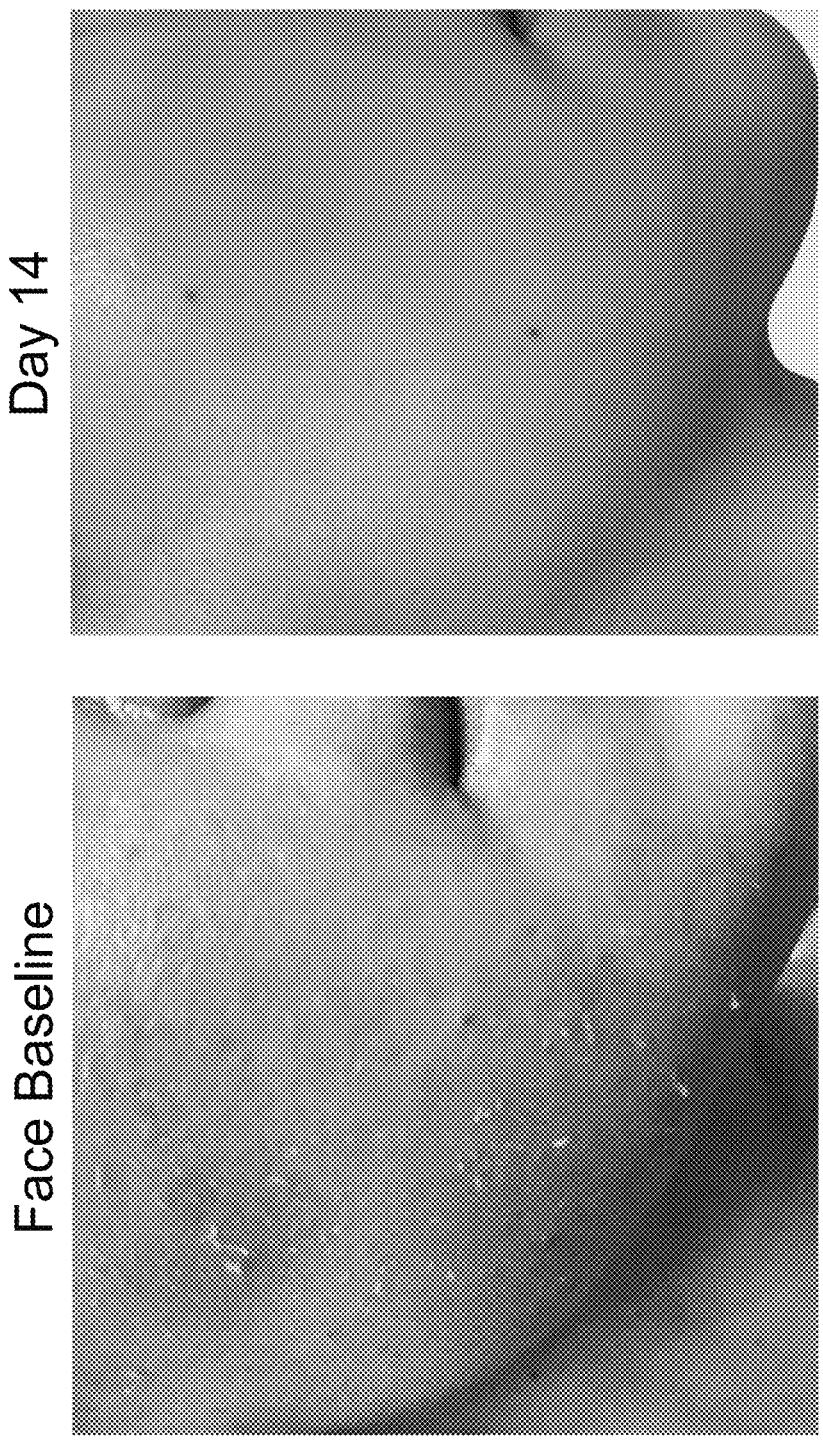

Photographs taken by participants at the beginning (Day 0) and end (Day 14) of the trial period also demonstrated exemplary improvement in skin condition in a variety of locations on the body, including the face (FIG. 14A), hands (FIG. 14B) and elbow (FIG. 14C).

REFERENCES

The following references are incorporated herein by reference in their entireties for all purposes.

1. Bonar E, Bukowski M, Chlebicka K, Madry A, Bereznicka A, Kosecka-Strojek M, Dubin G, Miedzobrodzki J, Mak P, Wladyka B. Human skin microbiota-friendly lysostaphin. International Journal of Biological Macromolecules. 2021; 183:852-60.
2. Chang Y, Ryu S. Characterization of a novel cell wall binding domain-containing *Staphylococcus aureus* endolysin LysSA97. Applied microbiology and biotechnology. 2017; 101:147-58.
3. Choi Y, Ha E, Kong M, Ryu S. A novel chimeric endolysin with enhanced lytic and binding activity against *Clostridium perfringens*. LWT. 2023 May 1; 181:114776.
4. Duyvejonck L, Gerstmans H, Stock M, Grimon D, Lavigne R, Briers Y. Rapid and high-throughput evaluation of diverse configurations of engineered lysins using the VersaTile technique. Antibiotics. 2021; 10(3):293.
5. Eichenseher F, Herpers B L, Badoux P, Leyva-Castillo J M, Geha R S, van der Zwart M, McKellar J, Janssen F, de Rooij B, Selvakumar L, Rohrig C. Linker-Improved Chimeric Endolysin Selectively Kills *Staphylococcus aureus* In Vitro, on Reconstituted Human Epidermis, and in a Murine Model of Skin Infection. Antimicrobial Agents and Chemotherapy. 2022; 66(5):e02273-21.
6. Gutiérrez D, Garrido V, Fernández L, Portilla S, Rodríguez A, Grilló M J, Garcia P. Phage lytic protein LysRODI prevents staphylococcal mastitis in mice. Frontiers in microbiology. 2020; 11:7.
7. Gutiérrez D, Rodríguez-Rubio L, Ruas-Madiedo P, Fernández L, Campelo A B, Briers Y, Nielsen M W, Pedersen K, Lavigne R, Garcia P, Rodríguez A. Design and selection of engineered lytic proteins with *Staphylococcus aureus* decolonizing activity. Frontiers in Microbiology. 2021; 12:723834.
8. Kost Y, Deutsch A, Mieczkowska K, Nazarian R, Muskat A, Hosgood H D, Lin J, Daily J P, Ohri N, Kabarriti R, Shinoda K. Bacterial Decolonization for Prevention of Radiation Dermatitis: A Randomized Clinical Trial. JAMA oncology. 2023 May 4.
9. Kost Y, Rzepecki A K, Deutsch A, Birnbaum M R, Ohri N, Hosgood H D, Lin J, Daily J P, Shinoda K, McLellan B N. Association of *Staphylococcus aureus* Colonization With Severity of Acute Radiation Dermatitis in Patients With Breast or Head and Neck Cancer. JAMA oncology. 2023 May 4.
10. Lee C, Kim J, Son B, Ryu S. Development of advanced chimeric endolysin to control multidrug-resistant *Staphylococcus aureus* through domain shuffling. ACS Infectious Diseases. 2021; 7(8):2081-92.
11. Matsuzaki S, Rashel M, Uchiyama J, Sakurai S, Ujihara T, Kuroda M, Ikeuchi M, Tani T, Fujieda M, Wakiguchi H, Imai S. Bacteriophage therapy: a revitalized therapy against bacterial infectious diseases. Journal of infection and chemotherapy. 2005; 11:211-9.
12. Obeso J M, Martinez B, Rodríguez A, Garcia P. Lytic activity of the recombinant staphylococcal bacteriophage ΦH5 endolysin active against *Staphylococcus aureus* in milk. International journal of food microbiology. 2008; 128(2):212-8.
13. Son B, Kong M, Lee Y, Ryu S. Development of a novel chimeric endolysin, Lys109 with enhanced lytic activity against *Staphylococcus aureus*. Frontiers in Microbiology. 2021; 11:615887.
14. Vermassen A, Leroy S, Talon R, Provot C, Popowska M, Desvaux M. Cell wall hydrolases in bacteria: insight on the diversity of cell wall amidases, glycosidases and peptidases toward peptidoglycan. Frontiers in microbiology. 2019; 10:331.
15. WO 2004/020635 A1
16. WO 2009/024327 A2
17. WO 2019/105936 A1
18. WO 2007/130655 A2

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as an acknowledgment or any form of suggestion that they constitute valid prior art or form part of the common general knowledge in any country in the world.

NUMBERED EMBODIMENTS OF THE DISCLOSURE

Notwithstanding the appended claims, the disclosure sets forth the following numbered embodiments:
1. A chimeric cell wall hydrolase (CWH) comprising:
   a) an enzymatically active domain (EAD) having at least 80, 81, 82, 83, 84, 85, 86, 87, 88, 89, 90, 91, 92, 93, 94, 95, 96, 97, 98, or 99% identity with sequence SEQ ID NO: 11; and
   b) a cell wall binding domain (CBD) having at least 80, 81, 82, 83, 84, 85, 86, 87, 88, 89, 90, 91, 92, 93, 94, 95, 96, 97, 98, or 99% identity with sequence:
      i) SEQ ID NO: 16;
      ii) SEQ ID NO: 17; or
      iii) SEQ ID NO: 18.
2. The chimeric CWH of embodiment 1, wherein the EAD comprises the sequence of SEQ ID NO: 11.
3. The chimeric CWH of embodiment 1 or embodiment 2, wherein the CBD comprises the sequence of SEQ ID NO: 16.
4. The chimeric CWH of embodiment 1 or embodiment 2, wherein the CBD comprises the sequence of SEQ ID NO: 17.
5. The chimeric CWH of embodiment 1 or embodiment 2, wherein the CBD comprises the sequence of SEQ ID NO: 18.
6. A chimeric cell wall hydrolase (CWH) comprising a sequence having at least 80, 81, 82, 83, 84, 85, 86, 87, 88, 89, 90, 91, 92, 93, 94, 95, 96, 97, 98, or 99% identity with SEQ ID NO: 21.
7. The chimeric CWH of embodiment 6, wherein the chimeric CWH comprises the sequence of SEQ ID NO: 21.
8. A chimeric cell wall hydrolase (CWH) comprising a sequence having at least 80, 81, 82, 83, 84, 85, 86, 87, 88, 89, 90, 91, 92, 93, 94, 95, 96, 97, 98, or 99% identity with SEQ ID NO: 22.
9. The chimeric CWH of embodiment 8, wherein the chimeric CWH comprises the sequence of SEQ ID NO: 22.
10. A chimeric cell wall hydrolase (CWH) comprising a sequence having at least 80, 81, 82, 83, 84, 85, 86, 87, 88, 89, 90, 91, 92, 93, 94, 95, 96, 97, 98, or 99% identity with SEQ ID NO: 24.
11. The chimeric CWH of embodiment 10, wherein the chimeric CWH comprises the sequence of SEQ ID NO: 24.

12. The chimeric CWH of any one of embodiments 1-11, wherein the chimeric CWH is active against a species of *Staphylococcus*.
13. The chimeric CWH of any one of embodiments 1-12, wherein the chimeric CWH is active against a species of *Staphylococcus*, and wherein the minimum inhibitory concentration (MIC) of that activity is determined via an MIC assay.
14. The chimeric CWH of any one of embodiments 1-13, wherein the chimeric CWH is active against a species of *Staphylococcus*, with an MIC less than or equal to 50 µg/mL.
15. The chimeric CWH of any one of embodiments 1-14, wherein the chimeric CWH is active against a species of *Staphylococcus*, with an MIC less than or equal to 10 µg/mL.
16. The chimeric CWH of any one of embodiments 1-15, wherein the chimeric CWH is active against a species of *Staphylococcus*, wherein the species is *S. agnetis, S. argensis, S. argenteus, S. arlettae, S. aureus, S. auricularis, S. capitis, S. caprae, S. carnosus, S. chromogenes, S. cohnii, S. condimenti, S. cornubiensis, S. delphini, S. devriesei, S. edaphicus, S. epidermidis, S. equi, S. equorum, S. felis, S. fleurettii, S. gallinarum, S. haemolyticus, S. hominis, S. hyicus, S. intermedius, S. kloosii, S. lentus, S. lugdunensis, S. lutrae, S. massiliensis, S. microti, S. muscae, S. nepalensis, S. pasteuri, S. petrasii, S. pettenkoferi, S. piscifermentans, S. pseudintermedius, S. pseudoxylosus, S. rostri, S. saccharolyticus, S. saprophyticus, S. schleiferi, S. schweitzeri, S. sciuri, S. simiae, S. simulans, S. stepanovicii, S. succinus, S. vitulinus, S. warneri,* or *S. xylosus*.
17. The chimeric CWH of any one of embodiments 1-16, wherein the chimeric CWH is active against *Staphylococcus aureus*.
18. The chimeric CWH of any one of embodiments 1-17, wherein the chimeric CWH is active against *Staphylococcus aureus*, with an MIC less than or equal to 50 µg/mL.
19. The chimeric CWH of any one of embodiments 1-18, wherein the chimeric CWH is active against *Staphylococcus aureus*, with an MIC less than or equal to 10 µg/mL.
20. The chimeric CWH of any one of embodiments 1-19, wherein the chimeric CWH demonstrates selective activity against one species of *Staphylococcus* in comparison to a second species of *Staphylococcus*.
21. The chimeric CWH of any one of embodiments 1-20, wherein the chimeric CWH demonstrates selective activity against a coagulase positive species (CoPS) of *Staphylococcus* over a coagulase negative species (CoNS) of *Staphylococcus*.
22. The chimeric CWH of any one of embodiments 1-21, wherein the chimeric CWH has at least 2-fold, at least 5-fold, or at least 10-fold selectivity against one species of *Staphylococcus* in comparison to a second species of *Staphylococcus*.
23. The chimeric CWH of any one of embodiments 1-22, wherein the chimeric CWH demonstrates selective activity against *Staphylococcus aureus* over *Staphylococcus epidermidis*.
24. The chimeric CWH of any one of embodiments 1-23, wherein the chimeric CWH has at least 2-fold selectivity for *Staphylococcus aureus* over *Staphylococcus epidermidis*.
25. The chimeric CWH of any one of embodiments 1-24, wherein the chimeric CWH has at least 10-fold selectivity for *Staphylococcus aureus* over *Staphylococcus epidermidis*.
26. The chimeric CWH of any one of embodiments 1-25, wherein the chimeric CWH is active against a species of *Staphylococcus*, and wherein the chimeric CWH retains activity after being exposed to a temperature up to 45° C.
27. The chimeric CWH of any one of embodiments 1-26, wherein the chimeric CWH is active against a species of *Staphylococcus*, and wherein the chimeric CWH retains activity after being exposed to a temperature of about 45° C.
28. The chimeric CWH of any one of embodiments 1-27, wherein the chimeric CWH is active against a species of *Staphylococcus*, and wherein the chimeric CWH retains activity after being exposed to a temperature of about 45° C. for about 4 weeks.
29. The chimeric CWH of any one of embodiments 1-28, wherein the chimeric CWH is active against a species of *Staphylococcus*, and wherein the chimeric CWH retains activity after being exposed to a temperature up to 50° C.
30. The chimeric CWH of any one of embodiments 1-29, wherein the chimeric CWH is active against a species of *Staphylococcus*, and wherein the chimeric CWH retains activity after being exposed to a temperature of about 50° C.
31. The chimeric CWH of any one of embodiments 26-30, wherein the chimeric CWH retains at least 5, 10, 15, 20, 25, 30, 35, 40, 45, 50, 55, 60, 65, 70, 75, 80, 85, 90, or 95% activity.
32. The chimeric CWH of any one of embodiments 1-31, wherein the chimeric CWH is active within a pH range of pH 6-8.
33. The chimeric CWH of any one of embodiments 1-32, wherein the chimeric CWH is active within a pH range of pH 5-8.
34. A topical formulation comprising a chimeric CWH according to any one of embodiments 1-33.
35. A topical formulation comprising a chimeric cell wall hydrolase (CWH) comprising a sequence having at least 80, 81, 82, 83, 84, 85, 86, 87, 88, 89, 90, 91, 92, 93, 94, 95, 96, 97, 98, or 99% identity with SEQ ID NO: 21.
36. The topical formulation of embodiment 35, wherein the chimeric CWH comprises the sequence of SEQ ID NO: 21.
37. The formulation of any one of embodiments 34-36, wherein the formulation is a hydrogel, lotion, cream, or gel-cream.
38. The formulation of any one of embodiments 34-37, wherein the formulation is a hydrogel.
39. The formulation of any one of embodiments 34-37, wherein the formulation is a cream.
40. The formulation of any one of embodiments 34-39, wherein the formulation comprises a humectant.
41. The formulation of any one of embodiments 34-40, wherein the formulation comprises a humectant selected from the list consisting of: aloe vera, betaine, butylene glycol, caprylyl glycol, dimethicone, fructose, glucomannan, glucose, glycerin, glyceryl glucoside, honey, hyaluronic acid, lactic acid, panthenol, polyethylene glycol, propylene glycol, propanediol, sodium hyaluronate, sodium lactate, sodium pyrrolidone carboxylic acid, sorbitol, and urea.

42. The formulation of any one of embodiments 34-41, wherein the formulation comprises 0.1-50% w/v humectant.
43. The formulation of any one of embodiments 34-42, wherein the formulation comprises 0.5-10% w/v humectant.
44. The formulation of any one of embodiments 34-43, wherein the formulation comprises a cellulose polymer.
45. The formulation of any one of embodiments 34-44, wherein the formulation comprises a cellulose polymer selected from the list consisting of: hydroxyethyl cellulose, methylcellulose, hydroxy methylcellulose, carboxymethyl cellulose, microcrystalline cellulose, ethyl cellulose, sodium carboxymethyl cellulose, hydroxypropyl cellulose, and cellulose acetate.
46. The formulation of any one of embodiments 34-45, wherein the formulation comprises a cellulose polymer, and wherein the cellulose polymer is hydroxy methylcellulose.
47. The formulation of any one of embodiments 34-46, wherein the formulation comprises 0.1-20% w/v of a cellulose polymer.
48. The formulation of any one of embodiments 34-47, wherein the formulation comprises 0.5-10% w/v of a cellulose polymer.
49. The formulation of any one of embodiments 34-48, wherein the formulation comprises 1-5% w/v of a cellulose polymer.
50. The formulation of any one of embodiments 34-49, wherein the formulation comprises a thickening agent, a gelling agent, and/or a polymer.
51. The formulation of any one of embodiments 34-50, wherein the formulation comprises a carbomer or acrylate polymer.
52. The formulation of any one of embodiments 34-51, wherein the formulation comprises 0.05-5.0% w/v carbomer or acrylate polymer.
53. The formulation of any one of embodiments 34-52, wherein the formulation comprises a salt.
54. The formulation of any one of embodiments 34-53, wherein the formulation comprises a salt selected from the list consisting of: calcium chloride, Dead Sea salt, Epsom salt, Himalayan pink salt, magnesium chloride, sea salt, and sodium chloride.
55. The formulation of any one of embodiments 34-54, wherein the formulation comprises 10-500 mM of a salt.
56. The formulation of any one of embodiments 34-55, wherein the formulation comprises 50-250 mM of a salt.
57. The formulation of any one of embodiments 34-56, wherein the formulation comprises a buffer.
58. The formulation of any one of embodiments 34-57, wherein the formulation comprises a buffer selected from the list consisting of: 4-(2-hydroxyethyl)-1-piperazineethanesulfonic acid, acetic acid, ammonium acetate, boric acid, citric acid, glycine, phosphoric acid, potassium hydroxide, potassium phosphate, sodium acetate, sodium bicarbonate, sodium borate, sodium carbonate, sodium citrate, sodium dihydrogen phosphate, sodium hydrogen phosphate, sodium hydroxide, sodium phosphate, sodium tetraborate, tris(hydroxymethyl)aminomethane, and trisodium phosphate.
59. The formulation of any one of embodiments 34-58, wherein the formulation comprises 1-150 mM of a buffer.
60. The formulation of any one of embodiments 34-59, wherein the formulation comprises 5-50 mM of a buffer.
61. The formulation of any one of embodiments 34-60, wherein the formulation comprises a surfactant.
62. The formulation of any one of embodiments 34-61, wherein the formulation comprises a surfactant selected from the list consisting of: ceteareth-20, cocamidopropyl betaine, coco-glucoside, decyl glucoside, decyl polyglucose, disodium laureth sulfosuccinate, glycereth-26, lauryl glucoside, lauryl polyglucose, sodium cocoyl glutamate, sodium cocoyl isethionate, sodium laureth sulfate, and sodium lauryl sulfate.
63. The formulation of any one of embodiments 34-62, wherein the formulation comprises 0.1-20% w/v of a surfactant.
64. The formulation of any one of embodiments 34-63, wherein the formulation comprises 1-10% w/v of a surfactant.
65. The formulation of any one of embodiments 34-64, wherein the formulation comprises a free amino acid.
66. The formulation of any one of embodiments 34-65, wherein the formulation comprises a free amino acid selected from the list consisting of: alanine, arginine, cysteine, glutamine, glycine, histidine, lysine, methionine, proline, serine, and threonine.
67. The formulation of any one of embodiments 34-66, wherein the formulation comprises 5-500 mM of a free amino acid.
68. The formulation of any one of embodiments 34-67, wherein the formulation comprises 10-250 mM of a free amino acid.
69. The formulation of any one of embodiments 34-68, wherein the formulation comprises an oil.
70. The formulation of any one of embodiments 34-69, wherein the formulation comprises an oil selected from the list consisting of: argan oil, avocado oil, baobab oil, camellia oil, carrot seed oil, coconut oil, evening primrose oil, grapeseed oil, hemp seed oil, jojoba oil, macadamia nut oil, marula oil, mineral oil, olive oil, pomegranate seed oil, raspberry seed oil, rosehip seed oil, squalane oil, sunflower seed oil, sweet almond oil, and tamanu oil.
71. The formulation of any one of embodiments 34-70, wherein the formulation comprises 0.1-20% w/v of an oil.
72. The formulation of any one of embodiments 34-71, wherein the formulation comprises 1-10% w/v of an oil.
73. The formulation of any one of embodiments 34-72, wherein the formulation comprises an alcohol.
74. The formulation of any one of embodiments 34-73, wherein the formulation comprises an alcohol selected from the list consisting of: cetyl alcohol, ethyl alcohol, isopropyl alcohol, and stearyl alcohol.
75. The formulation of any one of embodiments 34-74, wherein the formulation comprises 0.1-20% w/v of an alcohol.
76. The formulation of any one of embodiments 34-75, wherein the formulation comprises 1-10% w/v of an alcohol.
77. The formulation of any one of embodiments 34-76, wherein the formulation comprises glycerol.
78. The formulation of any one of embodiments 34-77, wherein the formulation comprises 0.5-50% w/v glycerol.

79. The formulation of any one of embodiments 34-78, wherein the formulation comprises 1-30% w/v glycerol.

80. The formulation of any one of embodiments 34-79, wherein the formulation comprises 1-5% w/v glycerol.

81. The formulation of any one of embodiments 34-80, wherein the formulation comprises petrolatum.

82. The formulation of any one of embodiments 34-81, wherein the formulation comprises 10-99% w/v petrolatum.

83. The formulation of any one of embodiments 34-81, wherein the formulation comprises 0.1-20% w/v petrolatum.

84. The formulation of any one of embodiments 34-83, wherein the formulation is thermostable at 45° C. for four weeks.

85. The formulation of any one of embodiments 34-84, wherein the formulation is thermostable at 45° C. for at least four weeks.

86. The formulation of any one of embodiments 34-85, wherein the formulation is thermostable at 45° C. for at least two months.

87. The formulation of any one of embodiments 34-86, wherein the formulation is thermostable at 50° C. for at least two months.

88. The formulation of any one of embodiments 34-87, wherein the formulation is active within a pH range of 6-8

89. The formulation of any one of embodiments 34-88, wherein the formulation is active within a pH range of 5-8.

90. A method of treating a condition associated with *Staphylococcus*, the method comprising the step of: administering a composition comprising a chimeric CWH according to any one of embodiments 1-33 or a formulation according to any one of embodiments 34-89.

91. The method of embodiment 90, wherein the composition or formulation is administered topically, enterally, or parenterally.

92. The method of embodiment 90 or 91, wherein the composition or formulation is administered topically.

93. The method of any one of embodiments 90-92, wherein the composition or formulation is administered 1-4 times every 1-7 days.

94. The method of any one of embodiments 90-93, wherein the composition or formulation is administered 1-4 times per day.

95. The method of any one of embodiments 90-94, wherein the composition or formulation is administered once or twice daily.

96. The method of any one of embodiments 90-95, wherein the composition or formulation is administered for a period of 1-14 days.

97. The method of any one of embodiments 90-96, wherein the composition or formulation is administered for a period of 1-12 weeks.

98. The method of any one of embodiments 90-97, wherein the composition or formulation is administered until resolution of symptoms.

99. The method of any one of embodiments 90-98, wherein the condition is associated with a species of *Staphylococcus* selected from: *S. agnetis, S. argensis, S. argenteus, S. arlettae, S. aureus, S. auricularis, S. capitis, S. caprae, S. carnosus, S. chromogenes, S. cohnii, S. condimenti, S. cornubiensis, S. delphini, S. devriesei, S. edaphicus, S. epidermidis, S. equi, S. equorum, S. felis, S. fleurettii, S. gallinarum, S. haemolyticus, S. hominis, S. hyicus, S. intermedius, S. kloosii, S. lentus, S. lugdunensis, S. lutrae, S. massiliensis, S. microti, S. muscae, S. nepalensis, S. pasteuri, S. petrasii, S. pettenkoferi, S. piscifermentans, S. pseudintermedius, S. pseudoxylosus, S. rostri, S. saccharolyticus, S. saprophyticus, S. schleiferi, S. schweitzeri, S. sciuri, S. simiae, S. simulans, S. stepanovicii, S. succinus, S. vitulinus, S. warneri*, and *S. xylosus*.

100. The method of any one of embodiments 90-99, wherein the condition is associated with *Staphylococcus aureus*.

101. The method of any one of embodiments 90-100, wherein the condition is an infection by a species of *Staphylococcus*.

102. The method of any one of embodiments 90-101, wherein the condition is overgrowth of a species of *Staphylococcus*.

103. The method of any one of embodiments 90-102, wherein the condition is dry skin, itchy skin, and/or red skin.

104. The method of any one of embodiments 90-102, wherein the condition is atopic dermatitis.

105. The method of any one of embodiments 90-102, wherein the condition is wound infection.

106. The method of any one of embodiments 90-102, wherein the condition is acute radiation dermatitis.

107. The method of any one of embodiments 90-102, wherein the condition is a chronic wound.

108. The method of any one of embodiments 90-107, wherein the method comprises a step of applying a second topical formulation after administration of the composition or formulation according to any one of embodiments 1-89.

109. The method of embodiment 108, wherein the second topical formulation is a hydrating formulation.

110. The method of embodiment 108 or 109, wherein the second topical formulation restores skin barrier.

111. The method of any one of embodiments 108-110, wherein the second topical formulation is a cream or lotion.

112. The method of any one of embodiments 108-111, wherein the second topical formulation is applied within 60 minutes of application of the composition or formulation according to any one of embodiments 1-89.

113. The method of any one of embodiments 108-112, wherein the second topical formulation is applied within 15 minutes of application of the composition or formulation according to any one of embodiments 1-75.

The invention claimed is:

1. A recombinant cell wall hydrolase (CWH) comprising:
   a) an enzymatically active domain (EAD) from LysSA12; and
   b) a cell wall binding domain (CBD) from PlySs2.

2. The recombinant CWH of claim 1, wherein the EAD has at least 90% sequence identity with the sequence of SEQ ID NO: 11.

3. The recombinant CWH of claim 1, wherein the CBD has at least 90% sequence identity with the sequence of SEQ ID NO: 17.

4. The recombinant CWH of claim 1, wherein the EAD comprises the sequence of SEQ ID NO: 11.

5. The recombinant CWH of claim 1, wherein the CBD comprises the sequence of SEQ ID NO: 17.

6. The recombinant CWH of claim 1, wherein the recombinant CWH has at least 80% sequence identity with the sequence of SEQ ID NO: 21.

7. The recombinant CWH of claim 1, wherein the recombinant CWH comprises the sequence of SEQ ID NO: 21.

8. The recombinant CWH of claim 1, wherein the recombinant CWH is active against a species of *Staphylococcus*.

9. The recombinant CWH of claim 8, wherein the recombinant CWH has a minimum inhibitory concentration (MIC) of less than or equal to 50 µg/mL against a species of *Staphylococcus*.

10. The recombinant CWH of claim 8, wherein the recombinant CWH has a minimum inhibitory concentration (MIC) of less than or equal to 10 µg/mL against a species of *Staphylococcus*.

11. The recombinant CWH of claim 8, wherein the species is *Staphylococcus aureus*.

12. The recombinant CWH of claim 8, wherein the recombinant CWH demonstrates selective activity against *Staphylococcus aureus* over *Staphylococcus epidermidis*.

13. The recombinant CWH of claim 12, wherein the recombinant CWH has at least 2-fold selectivity for *Staphylococcus aureus* over *Staphylococcus epidermidis*.

14. The recombinant CWH of claim 12, wherein the recombinant CWH has at least 10-fold selectivity for *Staphylococcus aureus* over *Staphylococcus epidermidis*.

15. The recombinant CWH of claim 8, wherein the recombinant CWH retains its anti-*Staphylococcus* activity after being exposed to a temperature up to 45° C.

16. The recombinant CWH of claim 8, wherein the recombinant CWH retains its anti-*Staphylococcus* activity after being exposed to a temperature up to 50° C.

17. The recombinant CWH of claim 8, wherein the recombinant CWH is active within a pH range of pH 6-8.

18. The recombinant CWH of claim 8, wherein the recombinant CWH is active within a pH range of pH 5-8.

19. A topical formulation comprising the recombinant CWH according to claim 1.

20. The formulation of claim 19, wherein the formulation is a hydrogel.

21. The formulation of claim 19, wherein the formulation comprises 1-10 µg/mL of the recombinant CWH.

22. The formulation of claim 19, wherein the formulation comprises 0.5-10% w/v of a humectant selected from the list consisting of: aloe vera, betaine, butylene glycol, caprylyl glycol, dimethicone, fructose, glucomannan, glucose, glycerin, glyceryl glucoside, honey, hyaluronic acid, lactic acid, panthenol, polyethylene glycol, propylene glycol, propanediol, sodium hyaluronate, sodium lactate, sodium pyrrolidone carboxylic acid, sorbitol, and urea.

23. The formulation of claim 19, wherein the formulation comprises 1-5% w/v of a cellulose polymer selected from the list consisting of: hydroxyethyl cellulose, methylcellulose, hydroxypropyl methyl cellulose, carboxymethyl cellulose, microcrystalline cellulose, ethyl cellulose, sodium carboxymethyl cellulose, hydroxypropyl cellulose, and cellulose acetate.

24. The formulation of claim 19, comprising a free amino acid selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine.

25. A method of treating a skin condition associated with *Staphylococcus*, the method comprising the step of applying the recombinant CWH of claim 1 to the skin.

26. The method of claim 25, wherein the skin condition is selected from the list consisting of: an infection by a species of *Staphylococcus*, an overgrowth of a species of *Staphylococcus*, dry skin, itchy skin, red skin, atopic dermatitis, wound infection, acute radiation dermatitis, and a chronic wound.

27. The method of claim 25, wherein the skin condition is atopic dermatitis.

28. The method of claim 25, wherein the skin condition is associated with *Staphylococcus aureus*.

29. The method of claim 25, wherein the recombinant CWH is applied to the skin 1-4 times per day until resolution of symptoms.

* * * * *

SEQUENCE LISTING

```
Sequence total quantity: 36
SEQ ID NO: 1                moltype = AA   length = 481
FEATURE                     Location/Qualifiers
source                      1..481
                            mol_type = protein
                            note = Staphylococcus phage SA12
                            organism = unidentified
SEQUENCE: 1
MQAKLTKKEF IEWLKTSEGK QYNADGWYGF QCFDYANAGW QVLFGYNLKG VGAKDIPSAN   60
DFNGLATVYQ NTPDFLAQPG DMVVFGSNYG AGYGHVAWVI EATLDYIIVY EQNWLGGGWT  120
DGVQQPGSGW EKVTRRQHAY DFPMWFIRPN FKSETAPRSV QSPTQASKKE TAKPQPKAVE  180
LKIIKDVVKG YDLPKRGSNP KFIVIHNDAG SKGATAEAYR NGLVNAPLSR LEAGIAHSYV  240
SGNTVWQALD ESQVGWHTAN QIGNKYGYGI EVCQSMGADN ATFLKNEQAT FQECARLLKK  300
WGLPANRNTI RLHNEFTSTS CPHRSSVLHT GFDPVTRGLL PEDKRLQLKD YFIKQIRAYM  360
DGKIPVATVS NESSASSNTV KPVASAWKRN KYGTYYMEES ARFTNGNQPI TVRKVGPFLS  420
CPVGYQFQPG GYCDYTEVML QDGHVWVGYT WEGQRYYLPI RTWNGSAPPN QILGDLWGEI  480
S                                                                 481

SEQ ID NO: 2                moltype = AA   length = 484
FEATURE                     Location/Qualifiers
source                      1..484
                            mol_type = protein
                            note = Staphylococcus phage phiIPLA35
                            organism = unidentified
SEQUENCE: 2
MLMTKNQAEK WFDNSLGKQF NPDLFFGFQC YDYANMFFML ATGERLQGLY AYNIPFDNKA   60
RIEKYGQIIK NYDSFLPQKL DIVVFPSKYG GGAGHVEIVE SANLNTFTSF GQNWNGKGWT  120
NGVAQPGWGP ETVTRHVYYY DDPMYFIRLN FPDKVSVGNR AKSVIKQATA KKQAVIKPKK  180
IMLVAGHGYN DPGAVGNGTN ERDFIRKYIT PNIAKYLRHA GHEVALYGGS SQSQDMYQDT  240
AYGVNVGNKK DYGLYWVKSQ GYDIVLEIHL DAAGESASGG HVIISSQFNA DTIDKSIQDV  300
IKNNLGQIRG VTPRNDLLNV NVSAEININY RLSELGFITN KKDMDWIKKN YDLYSKLIAG  360
AIHGKPIGGL VAGNVKTSAK NQKNPPVPAG YTLDKNNVPY KKEAGNYTVA NVKGNNVRDG  420
YSTNSRITGV LPNNATIKYD GAYCINGYRW ITYIANSGQR RYIATGEVDK AGNRISSFGK  480
FSTI                                                              484

SEQ ID NO: 3                moltype = AA   length = 245
FEATURE                     Location/Qualifiers
source                      1..245
                            mol_type = protein
                            note = Prophage in Streptococcus suis strain 89/1591
                            organism = unidentified
SEQUENCE: 3
MTTVNEALNN VRAQVGSGVS VGNGECYALA SWYERMISPD ATVGLGAGVG WVSGAIGDTI   60
SAKNIGSSYN WQANGWTVST SGPFKAGQIV TLGATPGNPY VPVIVEAVD GDRLTILEAQN  120
FGGKRYPVRN YYSAASYRQQ VVHYITPPGT VAQSAPNLAG SRSYRETGTM TVTVDALNVR  180
RAPNTSGEIV AVYKRGESFD YDTVIIDVNG YVWVSYIGGS GKRNYATGA TKDGKRFGNA  240
WGTFK                                                             245

SEQ ID NO: 4                moltype = AA   length = 467
FEATURE                     Location/Qualifiers
source                      1..467
                            mol_type = protein
                            note = Staphylococcus phage Twort
                            organism = unidentified
SEQUENCE: 4
MKTLKQAESY IKSKVNTGTD FDGLYGYQCM DLAVDYIYHV TDGKIRMWGN AKDAINNSFG   60
GTATVYKNYP AFRPKYGDVV VWTTGNFATY GHIAIVTNPD PYGDLQYVTV LEQNWNGNGI  120
YKTELATIRT HDYTGITHFI RPNFATESSV KKKDTKKKPK PSNRDGINKD KIVYDRTNIN  180
YNMVKRGYNP VGVILHNDAG SMTGLQYKNN LQNAGYNRWA QGIAHSYISE GQVWQALGES  240
RIAWHCANQW GNKNLYGIEI CQSMTASDEQ FLKNEQTAFY EASRMLKKWG LKPDKNTVRL  300
HMEYYQTACP HRSMKLHVGK DPTKTSITQA DIEKLKEYIP KQIKMYYEGK TPVPTVVNQK  360
AKTKPVKQSS TSGWNVNNYG TYYKSESATF KCTARQGIVT RYTGPFTTCP QAGVLYYGQS  420
VTYDTVCKQD GYVWISWTTN GGQDVWMPVR TWDKNTDIMG QLWGDIY                467

SEQ ID NO: 5                moltype = AA   length = 249
FEATURE                     Location/Qualifiers
source                      1..249
                            mol_type = protein
                            note = Staphylococcus phage CSA13
                            organism = unidentified
SEQUENCE: 5
MKSQKQAKQW IDVNTGKGVD FDGAYGFQCM DLAVAYVYYI TDGKVRMWGN AKDAINNDFK   60
GLATVYENTP RFKPQLGDVA VYTNSQYGHI QVVISGNLDY YTCLEQNWLN GGYDGWEKAT  120
IRTHYYDGVT HFIRPKFSDS NSQVLEQKIQ ETNSWNKNQY GTLYKSENGT FTCGSLPIFA  180
RVGSPKLSEP NGYWFQPNGY TPYDEVCLSD GLVWIGYNWQ GTRYYLPVRQ WNGKTGNAYS  240
VGVPWGVFS                                                         249

SEQ ID NO: 6                moltype = AA   length = 495
```

```
FEATURE                 Location/Qualifiers
source                  1..495
                        mol_type = protein
                        note = Staphylococcus phage CSA5
                        organism = unidentified
SEQUENCE: 6
MAKTQAEINK RLDAYAKGTV DSPYRIKKAT SYDPSFGVME AGAIDADGYY HAQCQDLITD    60
YVLWLTDNKV RTWGNAKDQI KQSYGTGFKI HENKPSTVPK KGWIAVFTSG SYQQWGHIGI   120
VYDGGNTSTF TILEQNWNGY ANKKPTKRVD NYYGLTHFIE IPVKAGTTVK KETAKKSASK   180
TPAPKKKATL KVSKNHINYT MDKRGKKPEG MVIHNDAGRS SGQQYENSLA NAGYARYANG   240
IAHYYGSEGY VWEAIDAKNQ IAWHTGDGTG ANSGNFRFAG IEVCQSMSAS DAQFLKNEQA   300
VFQFTAEKFK EWGLTPNRKT VRLHMEFVPT ACPHRSMVLH TGFNPVTQGR PSQAIMNKLK   360
DYFIKQIKNY MDKGTSSSTV VKDGKTSSAS TPATRPVTGS WKKNQYGTWY KPENATFVNG   420
NQPIVTRIGS PFLNAPVGGN LPAGATIVYD EVCIQAGHIW IGYNAYNGDR VYCPVRTCQG   480
VPPNHIPGVA WGVFK                                                    495

SEQ ID NO: 7            moltype = AA    length = 481
FEATURE                 Location/Qualifiers
source                  1..481
                        mol_type = protein
                        note = Staphylococcal phage phiH5
                        organism = unidentified
SEQUENCE: 7
MQAKLTKKEF IEWLKTSEGK QYNADGWYGF QCFDYANAGW KALFGLLLKG VGAKDIPFAN    60
NFDGLATVYQ NTPDFLAQPG DMVVFGSNYG AGYGHVAWVI EATLDYIIVY EQNWLGGGWT   120
DGVQQPGSGW EKVTRRQHAY DFPMWFIRPN FKSETAPRSV QSPTQASKKE TAKPQPKAVE   180
LKIIKDVVKG YDLPKRGSNP NFIVIHNDAG SKGATAEAYR NGLVNAPLSR LEAGIAHSYV   240
SGNTVWQALD ESQVGWHTAN QIGNKYGYGI EVCQSMGADN ATFLKNEQAT FQECARLLKK   300
WGLPANRNTI RLHNEFTSTS CPHRSSVLHT GFDPVTRGLL PEDKRLQLKD YFIKQIRAYM   360
DGKIPVATVS NDSSASSNTV KPVASAWKRN KYGTYYMEES ARFTNGNQPI TVRKVGPFLS   420
CPVGYQFQPG GYCDYTEVML QDGHVWVGYT WEGQRYYLPI RTWNGSAPPN QILGDLWGEI   480
S                                                                   481

SEQ ID NO: 8            moltype = AA    length = 362
FEATURE                 Location/Qualifiers
source                  1..362
                        mol_type = protein
                        organism = Staphylococcus capitis
SEQUENCE: 8
MDTNRKFTLV KSLSIGLGTF LVGSVFLTVN DEASASTKVD APKVEQEAPA KADAPKVEQE    60
APAKADAPKV EQEAPAKVDA PKVEQEAPAK VDAPKVEQEA PAKADAPKVE QKRTFVREAA   120
QSNHSASWLN NYKKGYGYGP YPLGINGGNH YGVDFFMNVG TPVRAISDGK IVEAGWTNYG   180
GGNEIGLVEN DGVHRQWYMH LSKFNVKVGD RVKAGQIIGW SGSTGYSTAP HLHFQRMTNS   240
FSNNTAQDPM PFLKSAGYGS NSTSSSNNNG YKTNKYGTLY KSESASFTAN TDIITRLTGP   300
FRSMPQSGVL RKGLTIKYDE VMKQDGHVWV GYNTNSGKRV YLPVRTWNES TGELGPLWGT   360
IK                                                                  362

SEQ ID NO: 9            moltype = AA    length = 470
FEATURE                 Location/Qualifiers
source                  1..470
                        mol_type = protein
                        note = Staphylococcal phage SA97
                        organism = unidentified
SEQUENCE: 9
MPSVRTYSQA ISYLKSLEGK AWNPDNAFGC QCFDTANQYW LYLFNHRLKG VGAADIPTWN    60
DFTNEATVYE NTVSFQALPG DVVIFNRNYG GGYGHVGIVI SATLDSITIL EQNWLGGAYW   120
SPPEVTTRRT HGYDFPMWFI RPFYAKETTA NKLRSAVKPV KQDLSKGKK IMLVAGHGIG   180
AYSNDPGAVA NGENERDFNR KNIIPRVKKY LESVGNTVLL YGGNSMNQDL YQDTLYGQRV   240
GNYKDYGMYW IKSEVKPDAI IEFHLDSASP QASGGHVIIS DRFPADDIDK ALSSSALDKTV   300
GKIRGVTPRG DLLNANVSAD LNLNYRLIEL GFITSTKDLN YIKNNLDSFT KRIAEAINGR   360
QIDAPSSKPS ADKITWNWKG VFYPNPEKAI RVRKTAGLTG TVVEEDSWLY TKDDWVKFDQ   420
VIKKDGYWWI RFKYQREGSS TNNFYCAVCR ITDKEQKIKN EKYWGTIEWA              470

SEQ ID NO: 10           moltype = AA    length = 209
FEATURE                 Location/Qualifiers
source                  1..209
                        mol_type = protein
                        organism = synthetic construct
SEQUENCE: 10
MSASDAQFLK NEQAVFQFTA EKFKEWGLTP NRKTVRLHME FVPTACPHRS MVLHTGFNPV    60
TQGRPSKAIM NKLKDYFIKQ IKNYMSKGTS SSTVVKKGKT SSASTPATRP VTGSWKKNQY   120
GTWYKPESAT FVNGNQPIVT RIGSPFLNAP VGGNLPAGAT IVYDEVCIQA GHIWIGYNAY   180
NGNRVYCPVR TCQGVPPSHV PGVAWGTFK                                    209

SEQ ID NO: 11           moltype = AA    length = 171
FEATURE                 Location/Qualifiers
source                  1..171
                        mol_type = protein
                        organism = synthetic construct
```

```
SEQUENCE: 11
MQAKLTKKEF IEWLKTSEGK QYNADGWYGF QCFDYANAGW QVLFGYNLKG VGAKDIPSAN    60
DFNGLATVYQ NTPDFLAQPG DMVVFGSNYG AGYGHVAWVI EATLDYIIVY EQNWLGGGWT   120
DGVQQPGSGW EKVTRRQHAY DFPMWFIRPN FKSETAPRSV QSPTQASKKE T           171

SEQ ID NO: 12          moltype = AA   length = 166
FEATURE                Location/Qualifiers
source                 1..166
                       mol_type = protein
                       organism = synthetic construct
SEQUENCE: 12
MKTLKQAESY IKSKVNTGTD FDGLYGYQCM DLAVDYIYHV TDGKIRMWGN AKDAINNSFG    60
GTATVYKNYP AFRPKYGDVV VWTTGNFATY GHIAIVTNPD PYGDLQYVTV LEQNWNGNGI   120
YKTELATIRT HDYTGITHFI RPNFATESSV KKKDTKKKPK PSNRDG                  166

SEQ ID NO: 13          moltype = AA   length = 144
FEATURE                Location/Qualifiers
source                 1..144
                       mol_type = protein
                       organism = synthetic construct
SEQUENCE: 13
MKSQKQAKQW IDVNTGKGVD FDGAYGFQCM DLAVAYVYYI TDGKVRMWGN AKDAINNDFK    60
GLATVYENTP RFKPQLGDVA VYTNSQYGHI QVVISGNLDY YTCLEQNWLN GGYDGWEKAT   120
IRTHYYDGVT HFIRPKFSDS NSQV                                         144

SEQ ID NO: 14          moltype = AA   length = 178
FEATURE                Location/Qualifiers
source                 1..178
                       mol_type = protein
                       organism = synthetic construct
SEQUENCE: 14
MAKTQAEINK RLDAYAKGTV DSPYRIKKAT SYDPSFGVME AGAIDADGYY HAQCQDLITD    60
YVLWLTDNKV RTWGNAKDQI KQSYGTGFKI HENKPSTVPK KGWIAVFTSG SYQQWGHIGI   120
VYDGGNTSTF TILEQNWNGY ANKKPTKRVD NYYGLTHFIE IPVKAGTTVK KETAKKSA    178

SEQ ID NO: 15          moltype = AA   length = 112
FEATURE                Location/Qualifiers
source                 1..112
                       mol_type = protein
                       organism = synthetic construct
SEQUENCE: 15
SNDSSASSNT VKPVASAWKR NKYGTYYMEE SARFTNGNQP ITVRKVGPFL SCPVGYQFQP    60
GGYCDYTEVM LQDGHVWVGY TWEGQRYYLP IRTWNGSAPP NQILGDLWGE IS          112

SEQ ID NO: 16          moltype = AA   length = 102
FEATURE                Location/Qualifiers
source                 1..102
                       mol_type = protein
                       organism = synthetic construct
SEQUENCE: 16
KNPPVPAGYT LDKNNVPYKK EAGNYTVANV KGNNVRDGYS TNSRITGVLP NNATIKYDGA    60
YCINGYRWIT YIANSGQRRY IATGEVDKAG NRISSFGKFS TI                     102

SEQ ID NO: 17          moltype = AA   length = 85
FEATURE                Location/Qualifiers
source                 1..85
                       mol_type = protein
                       organism = synthetic construct
SEQUENCE: 17
SRSYRETGTM TVTVDALNVR RAPNTSGEIV AVYKRGESFD YDTVIIDVNG YVWVSYIGGS    60
GKRNYVATGA TKDGKRFGNA WGTFK                                         85

SEQ ID NO: 18          moltype = AA   length = 113
FEATURE                Location/Qualifiers
source                 1..113
                       mol_type = protein
                       organism = synthetic construct
SEQUENCE: 18
MPFLKSAGYG SNSTSSSNNN GYKTNKYGTL YKSESASFTA NTDIITRLTG PFRSMPQSGV    60
LRKGLTIKYD EVMKQDGHVW VGYNTNSGKR VYLPVRTWNE STGELGPLWG TIK         113

SEQ ID NO: 19          moltype = AA   length = 106
FEATURE                Location/Qualifiers
source                 1..106
                       mol_type = protein
                       organism = synthetic construct
SEQUENCE: 19
PSSKPSADKI TWNWKGVFYP NPEKAIRVRK TAGLTGTVVE EDSWLYTKDD WVKFDQVIKK    60
DGYWWIRFKY QREGSSTNNF YCAVCRITDK EQKIKNEKYW GTIEWA                 106
```

```
SEQ ID NO: 20            moltype = AA  length = 108
FEATURE                  Location/Qualifiers
source                   1..108
                         mol_type = protein
                         organism = synthetic construct
SEQUENCE: 20
SASTPATRPV TGSWKKNQYG TWYKPESATF VNGNQPIVTR IGSPFLNAPV GGNLPAGATI    60
VYDEVCIQAG HIWIGYNAYN GNRVYCPVRT CQGVPPSHVP GVAWGTFK                108

SEQ ID NO: 21            moltype = AA  length = 260
FEATURE                  Location/Qualifiers
source                   1..260
                         mol_type = protein
                         organism = synthetic construct
SEQUENCE: 21
MQAKLTKKEF IEWLKTSEGK QYNADGWYGF QCFDYANAGW QVLFGYNLKG VGAKDIPSAN    60
DFNGLATVYQ NTPDFLAQPG DMVVFGSNYG AGYGHVAWVI EATLDYIIVY EQNWLGGGWT   120
DGVQQPGSGW EKVTRRQHAY DFPMWFIRPN FKSETAPRSV QSPTQASKKE TTSSRSYRET   180
GTMTVTVDAL NVRRAPNTSG EIVAVYKRGE SFDYDTVIID VNGYVWVSYI GGSGKRNYVA   240
TGATKDGKRF GNAWGTFKLE                                               260

SEQ ID NO: 22            moltype = AA  length = 282
FEATURE                  Location/Qualifiers
source                   1..282
                         mol_type = protein
                         organism = synthetic construct
SEQUENCE: 22
MQAKLTKKEF IEWLKTSEGK QYNADGWYGF QCFDYANAGW QVLFGYNLKG VGAKDIPSAN    60
DFNGLATVYQ NTPDFLAQPG DMVVFGSNYG AGYGHVAWVI EATLDYIIVY EQNWLGGGWT   120
DGVQQPGSGW EKVTRRQHAY DFPMWFIRPN FKSETAPRSV QSPTQASKKE TTSKNPPVPA   180
GYTLDKNNVP YKKEAGNYTV ANVKGNNVRD GYSTNSRITG VLPNNATIKY DGAYCINGYR   240
WITYIANSGQ RRYIATGEVD KAGNRISSFG KFSTIKLAAA LE                      282

SEQ ID NO: 23            moltype = AA  length = 292
FEATURE                  Location/Qualifiers
source                   1..292
                         mol_type = protein
                         organism = synthetic construct
SEQUENCE: 23
MQAKLTKKEF IEWLKTSEGK QYNADGWYGF QCFDYANAGW QVLFGYNLKG VGAKDIPSAN    60
DFNGLATVYQ NTPDFLAQPG DMVVFGSNYG AGYGHVAWVI EATLDYIIVY EQNWLGGGWT   120
DGVQQPGSGW EKVTRRQHAY DFPMWFIRPN FKSETAPRSV QSPTQASKKE TTSSNDSSAS   180
SNTVKPVASA WKRNKYGTYY MEESARFTNG NQPITVRKVG PFLSCPVGYQ FQPGGYCDYT   240
EVMLQDGHVW VGYTWEGQRY YLPIRTWNGS APPNQILGDL WGEISKLAAA LE           292

SEQ ID NO: 24            moltype = AA  length = 293
FEATURE                  Location/Qualifiers
source                   1..293
                         mol_type = protein
                         organism = synthetic construct
SEQUENCE: 24
MQAKLTKKEF IEWLKTSEGK QYNADGWYGF QCFDYANAGW QVLFGYNLKG VGAKDIPSAN    60
DFNGLATVYQ NTPDFLAQPG DMVVFGSNYG AGYGHVAWVI EATLDYIIVY EQNWLGGGWT   120
DGVQQPGSGW EKVTRRQHAY DFPMWFIRPN FKSETAPRSV QSPTQASKKE TTSMPFLKSA   180
GYGSNSTSSS NNNGYKTNKY GTLYKSESAS FTANTDIITR LTGPFRSMPQ SGVLRKGLTI   240
KYDEVMKQDG HVWVGYNTNS GKRVYLPVRT WNESTGELGP LWGTIKKLAA ALE          293

SEQ ID NO: 25            moltype = AA  length = 288
FEATURE                  Location/Qualifiers
source                   1..288
                         mol_type = protein
                         organism = synthetic construct
SEQUENCE: 25
MQAKLTKKEF IEWLKTSEGK QYNADGWYGF QCFDYANAGW QVLFGYNLKG VGAKDIPSAN    60
DFNGLATVYQ NTPDFLAQPG DMVVFGSNYG AGYGHVAWVI EATLDYIIVY EQNWLGGGWT   120
DGVQQPGSGW EKVTRRQHAY DFPMWFIRPN FKSETAPRSV QSPTQASKKE TTSSASTPAT   180
RPVTGSWKKN QYGTWYKPES ATFVNGNQPI VTRIGSPFLN APVGGNLPAG ATIVYDEVCI   240
QAGHIWIGYN AYNGNRVYCP VRTCQGVPPS HVPGVAWGTF KKLAAALE                288

SEQ ID NO: 26            moltype = AA  length = 286
FEATURE                  Location/Qualifiers
source                   1..286
                         mol_type = protein
                         organism = synthetic construct
SEQUENCE: 26
MQAKLTKKEF IEWLKTSEGK QYNADGWYGF QCFDYANAGW QVLFGYNLKG VGAKDIPSAN    60
DFNGLATVYQ NTPDFLAQPG DMVVFGSNYG AGYGHVAWVI EATLDYIIVY EQNWLGGGWT   120
DGVQQPGSGW EKVTRRQHAY DFPMWFIRPN FKSETAPRSV QSPTQASKKE TTSPSSKPSA   180
```

```
DKITWNWKGV FYPNPEKAIR VRKTAGLTGT VVEEDSWLYT KDDWVKFDQV IKKDGYWWIR    240
FKYQREGSST NNFYCAVCRI TDKEQKIKNE KYWGTIEWAK LAAALE                  286

SEQ ID NO: 27           moltype = AA  length = 277
FEATURE                 Location/Qualifiers
source                  1..277
                        mol_type = protein
                        organism = synthetic construct
SEQUENCE: 27
MKTLKQAESY IKSKVNTGTD FDGLYGYQCM DLAVDYIYHV TDGKIRMWGN AKDAINNSFG    60
GTATVYKNYP AFRPKYGDVV VWTTGNFATY GHIAIVTNPD PYGDLQYVTV LEQNWNGNGI   120
YKTELATIRT HDYTGITHFI RPNFATESSV KKKDTKKKPK PSNRDGTSKN PPVPAGYTLD   180
KNNVPYKKEA GNYTVANVKG NNVRDGYSTN SRITGVLPNN ATIKYDGAYC INGYRWITYI   240
ANSGQRRYIA TGEVDKAGNR ISSFGKFSTI KLAAALE                            277

SEQ ID NO: 28           moltype = AA  length = 255
FEATURE                 Location/Qualifiers
source                  1..255
                        mol_type = protein
                        organism = synthetic construct
SEQUENCE: 28
MKTLKQAESY IKSKVNTGTD FDGLYGYQCM DLAVDYIYHV TDGKIRMWGN AKDAINNSFG    60
GTATVYKNYP AFRPKYGDVV VWTTGNFATY GHIAIVTNPD PYGDLQYVTV LEQNWNGNGI   120
YKTELATIRT HDYTGITHFI RPNFATESSV KKKDTKKKPK PSNRDGTSSR SYRETGTMTV   180
TVDALNVRRA PNTSGEIVAV YKRGESFDYD TVIIDVNGYV WVSYIGGSGK RNYVATGATK   240
DGKRFGNAWG TFKLE                                                   255

SEQ ID NO: 29           moltype = AA  length = 288
FEATURE                 Location/Qualifiers
source                  1..288
                        mol_type = protein
                        organism = synthetic construct
SEQUENCE: 29
MKTLKQAESY IKSKVNTGTD FDGLYGYQCM DLAVDYIYHV TDGKIRMWGN AKDAINNSFG    60
GTATVYKNYP AFRPKYGDVV VWTTGNFATY GHIAIVTNPD PYGDLQYVTV LEQNWNGNGI   120
YKTELATIRT HDYTGITHFI RPNFATESSV KKKDTKKKPK PSNRDGTSMP FLKSAGYGSN   180
STSSSNNNGY KTNKYGTLYK SESASFTANT DIITRLTGPF RSMPQSGVLR KGLTIKYDEV   240
MKQDGHVWVG YNTNSGKRVY LPVRTWNEST GELGPLWGTI KKLAAALE                288

SEQ ID NO: 30           moltype = AA  length = 255
FEATURE                 Location/Qualifiers
source                  1..255
                        mol_type = protein
                        organism = synthetic construct
SEQUENCE: 30
MKSQKQAKQW IDVNTGKGVD FDGAYGFQCM DLAVAYVYYI TDGKVRMWGN AKDAINNDFK    60
GLATVYENTP RFKPQLGDVA VYTNSQYGHI QVVISGNLDY YTCLEQNWLN GGYDGWEKAT   120
IRTHYYDGVT HFIRPKFSDS NSQVTSKNPP VPAGYTLDKN NVPYKKEAGN YTVANVKGNN   180
VRDGYSTNSR ITGVLPNNAT IKYDGAYCIN GYRWITYIAN SGQRRYIATG EVDKAGNRIS   240
SFGKFSTIKL AAALE                                                   255

SEQ ID NO: 31           moltype = AA  length = 233
FEATURE                 Location/Qualifiers
source                  1..233
                        mol_type = protein
                        organism = synthetic construct
SEQUENCE: 31
MKSQKQAKQW IDVNTGKGVD FDGAYGFQCM DLAVAYVYYI TDGKVRMWGN AKDAINNDFK    60
GLATVYENTP RFKPQLGDVA VYTNSQYGHI QVVISGNLDY YTCLEQNWLN GGYDGWEKAT   120
IRTHYYDGVT HFIRPKFSDS NSQVTSSRSY RETGTMTVTV DALNVRRAPN TSGEIVAVYK   180
RGESFDYDTV IIDVNGYVWV SYIGGSGKRN YVATGATKDG KRFGNAWGTF KLE          233

SEQ ID NO: 32           moltype = AA  length = 266
FEATURE                 Location/Qualifiers
source                  1..266
                        mol_type = protein
                        organism = synthetic construct
SEQUENCE: 32
MKSQKQAKQW IDVNTGKGVD FDGAYGFQCM DLAVAYVYYI TDGKVRMWGN AKDAINNDFK    60
GLATVYENTP RFKPQLGDVA VYTNSQYGHI QVVISGNLDY YTCLEQNWLN GGYDGWEKAT   120
IRTHYYDGVT HFIRPKFSDS NSQVTSMPFL KSAGYGSNST SSSNNNGYKT NKYGTLYKSE   180
SASFTANTDI ITRLTGPFRS MPQSGVLRKG LTIKYDEVMK QDGHVWVGYN TNSGKRVYLP   240
VRTWNESTGE LGPLWGTIKK LAAALE                                       266

SEQ ID NO: 33           moltype = AA  length = 289
FEATURE                 Location/Qualifiers
source                  1..289
                        mol_type = protein
                        organism = synthetic construct
```

```
SEQUENCE: 33
MAKTQAEINK  RLDAYAKGTV  DSPYRIKKAT  SYDPSFGVME  AGAIDADGYY  HAQCQDLITD    60
YVLWLTDNKV  RTWGNAKDQI  KQSYGTGFKI  HENKPSTVPK  KGWIAVFTSG  SYQQWGHIGI   120
VYDGGNTSTF  TILEQNWNGY  ANKKPTKRVD  NYYGLTHFIE  IPVKAGTTVK  KETAKKSATS   180
KNPPVPAGYT  LDKNNVPYKK  EAGNYTVANV  KGNNVRDGYS  TNSRITGVLP  NNATIKYDGA   240
YCINGYRWIT  YIANSGQRRY  IATGEVDKAG  NRISSFGKFS  TIKLAAALE                289

SEQ ID NO: 34           moltype = AA  length = 267
FEATURE                 Location/Qualifiers
source                  1..267
                        mol_type = protein
                        organism = synthetic construct
SEQUENCE: 34
MAKTQAEINK  RLDAYAKGTV  DSPYRIKKAT  SYDPSFGVME  AGAIDADGYY  HAQCQDLITD    60
YVLWLTDNKV  RTWGNAKDQI  KQSYGTGFKI  HENKPSTVPK  KGWIAVFTSG  SYQQWGHIGI   120
VYDGGNTSTF  TILEQNWNGY  ANKKPTKRVD  NYYGLTHFIE  IPVKAGTTVK  KETAKKSATS   180
SRSYRETGTM  TVTVDALNVR  RAPNTSGEIV  AVYKRGESFD  YDTVIIDVNG  YVWVSYIGGS   240
GKRNYVATGA  TKDGKRFGNA  WGTFKLE                                          267

SEQ ID NO: 35           moltype = AA  length = 300
FEATURE                 Location/Qualifiers
source                  1..300
                        mol_type = protein
                        organism = synthetic construct
SEQUENCE: 35
MAKTQAEINK  RLDAYAKGTV  DSPYRIKKAT  SYDPSFGVME  AGAIDADGYY  HAQCQDLITD    60
YVLWLTDNKV  RTWGNAKDQI  KQSYGTGFKI  HENKPSTVPK  KGWIAVFTSG  SYQQWGHIGI   120
VYDGGNTSTF  TILEQNWNGY  ANKKPTKRVD  NYYGLTHFIE  IPVKAGTTVK  KETAKKSATS   180
MPFLKSAGYG  SNSTSSSNNN  GYKTNKYGTL  YKSESASFTA  NTDIITRLTG  PFRSMPQSGV   240
LRKGLTIKYD  EVMKQDGHVW  VGYNTNSGKR  VYLPVRTWNE  STGELGPLWG  TIKKLAAALE   300

SEQ ID NO: 36           moltype = AA  length = 259
FEATURE                 Location/Qualifiers
source                  1..259
                        mol_type = protein
                        organism = synthetic construct
SEQUENCE: 36
MDGSYLFEYP  IWQRFGRYTG  GLNFNGGRHY  GIDFGMPSGT  NVYAVKGGIA  DKVWTDYGGG    60
NSIQIKTGAN  EWNWYMHLSK  QLARQGQRIK  AGQLIGKSGA  TGNFVRGAHL  HFQLMQGSHP   120
GNDTAKDPEK  WLKSLKGSGV  RSGSGTSSND  SSASSNTVKP  VASAWKRNKY  GTYYMEESAR   180
FTNGNQPITV  RKVGPFLSCP  VGYQFQPGGY  CDYTEVMLQD  GHVWVGYTWE  GQRYYLPIRT   240
WNGSAPPNQI  LGDLWGEIS                                                    259
```